United States Patent [19]
Slightom et al.

[11] Patent Number: 5,824,866
[45] Date of Patent: *Oct. 20, 1998

[54] RI T-DNA PROMOTERS

[75] Inventors: Jerry L. Slightom, Kalamazoo, Mich.; David A. Tepfer, Paris, France

[73] Assignee: Mycogen Plant Science, Inc., San Diego, Calif.

[*] Notice: The term of this patent shall not extend beyond the expiration date of Pat. Nos. 5,182,200 and 5,366,887.

[21] Appl. No.: 458,831

[22] Filed: Jun. 2, 1995

Related U.S. Application Data

[62] Division of Ser. No. 336,346, Nov. 8, 1994, Pat. No. 5,466,792, which is a division of Ser. No. 8,216, Jan. 25, 1993, Pat. No. 5,366,887, which is a division of Ser. No. 725,368, Apr. 22, 1985, Pat. No. 5,182,200.

[51] Int. Cl.$^6$ .............................. A01H 5/00; C12N 5/04; C12N 15/31; C12N 15/84
[52] U.S. Cl. ........................ 800/205; 800/255; 536/23.7; 536/24.1; 435/172.3; 435/252.2; 435/419
[58] Field of Search ................................ 536/23.7, 24.1; 435/172.3, 240.4, 252.2, 419; 800/205, 250, 255

[56] References Cited

U.S. PATENT DOCUMENTS 5,182,200  1/1993  Slightom et al. .................... 435/172.3
5,366,887  11/1994  Slightom et al. .................... 435/240.4

OTHER PUBLICATIONS

Haffman et al. 1984, J. Bacteriol. 157: 269–276.
Barker et al. 1983, Plant Mol. Biol. 2:335–350.
Herrera–Estrella et al. 1983, Nature 303:209–213.
Zambryski et al. 1983, EMBO J 2(12):2143–2150.
Goodman et al. 1987. Science 236:48–54.

*Primary Examiner*—David T. Fox
*Attorney, Agent, or Firm*—Saliwanchik, Lloyd & Saliwanchik

[57] ABSTRACT

The sequence of the $T_L$-DNA of Ri plasmids found in *Agrobacterium rhizogenes* strains HRI and A4 is disclosed. Sixteen open reading frames bounded by eukaryotic promoters, ribosome binding sites, and polyadenylation sites were found, five of which were observed to be transcribed in a developmentally and phenotypically regulated manner. The use of promoters and polyadenylation sites from pRi $T_L$-DNA to control expression of heterologous foreign structural genes is taught, using as examples the structural genes for *Phaseolus vulgaris* storage protein (phaseolin), *P. vulgaris* lectin, a sweet protein (thaumatin), and *Bacillus thuringiensis* crystal protein. Vectors useful for manipulation of sequences of the structural genes and T-DNA are also provided.

4 Claims, 16 Drawing Sheets

```
GGCCGCAGGATTTCGTTCGTCGTGCGTGATGAGATCGATAAATGTTTATCGACGAGGACA   60
AGATCGACGATGCGGTTCTTGCGCTGTTGTAGTGACGCTCCACAACGAGTGTTGCGCCGT  120
GAAAGGCTTTGACTGGGCCGCGACGGACCGCCTTTGCAGGAAGGGTTCGGTCGGCGATCC  180
CGTCAATAAATCGAAGCTATTGATCCTGACGGATAAAGGTCTGCGTCGATCGGAGGAGCT  240
ATTCCGACAGCTGTTTACGCGCTAGCCATTGGCCGACGGTCTTTGCGCCCTCCATTCCCA  300
CGGCGTAGTTAATGCCGGCGGGGACGGGAGTGTCTACTATGTGCAAGCACGTCGGCGAAC  360
CATGCCTTCGGATTAATGTCGTTCAGACGGGCGGTCGTAAGTTGAATGAGTATGACTGCC  420
GCATGGTCAGCGCCGCGTTGGGAGCCGGCAGATGTCCAGTCGCGGCGCCTCAAGGCCATC  480
ACATGTTCACTCTGTGGCCAGAAGGCGTCGCTCCTTGGGTGGCAGGATATATTGTGATGT  540
AAACAGATTAGATATGGACATGCGAAGTCGTTTTAACGCATGCTTTATCGAATATAAAAT  600
GTAGATGGGCTAATGTGGTTTTACGTCATGTGAATAAAAGTTCAGCATTCGTTTAATAAT  660
ATTTCAATATCGGTGTCTAGAGACCCGTGGATTTGTATAGTCAGCACCATGATATGAATC  720
TATAAAATATTGTATCTCCAATTGCAATTCAATCGATATAAGAAATTAATACAAGCCGTT  780
CATATAGTAAGGTTGCCAATGGCATTCAATAACGACCGTACAGTTGCCGCTATATTAATC  840
TACGTGCCATTTCTTAAATAAAGATAGGCGAATGACTATCGAAAATAAAACAATTATTAA  900
TGAGTGAAAACGTATTGCACAAATAAAGATTCATTATGGTTGGCTCAAATTTTGGCTCTG  960
GTGCTCGATGACGTCGAGATGAGGACAGTAGTGATCAACTTGGCGGTCGATACCTTGGTT 1020
ACGCCACTCCCAGAGTGCCATGTCGTCCTCCGAGCGGTCTGAGATAACCCAGTCGGCAAT 1080
TGCTGCTGCATTGCCGGGCGTTCCCCAACCACGACGAATATGCTTTCGTTCATCTAACTC 1140
GCGTCGCACTGCCCTCCCAGTCATGAAGTCAAAGCCAAATTCTACCCTCTCTCCATTTCC 1200
CAGCTCAGTCGAGAAATCGTAACACCTCGTGGCAGCTGACAGTTTCAGAAAGGGCGTAT 1260
CCCTCGAACTCCAGGGTCCTCTTTCACATAGTTAGCAAGGCGTACTGCTGCATAATCTGC 1320
GTTGAAGGCTCTGATGACTACAGGATCCTCGGACAAGCCCAATTGATCAGGGCGAACCCT 1380
CGCGCTCATAATATGAATTGCGACGACCCTTGCTTCCTGTCGGAGCATCGAATCAATCCA 1440
AGCCTTCCCTGCGGCATAGAGGTCATCGACTGCGATGTCATCAAGATCGAGTAGCTTTGC 1500
CAACCTAGGAAGTTCTTGAGGAAAAATCACCGGCATGACAGCAACCGTCTCTCGCCAGTC 1560
```

Figure 2A

```
AGTTGCCGGACTGGCTTCCCTAACGCCATCCACGAATGCCTCACCGCTTGCGTATTTGAA 1620
TGTGTAAAAGAGAAGGACCACTCTTTGGCGGTACTTCGGACGCCGGCTTAGCCACGCGGC 1680
AATAATGTGGGCCTCAAACTCACGACCATCCAAAAATATAGTCGCGCCTGGATTGACCTC 1740
GCTGGCCTTGTCGAGAAGAGGTTCCAAAAAGGGAACGGTGTCTTTCGTAATAGTACTTAA 1800
ATCTGTGAGTTCGCCATGCGAAACCTCTCGAACGATTATCGGCGTATCCCTGACATCAGC 1860
TGAATGAAATTCTCGGACGAGTTTGTCGGGCAAAGTGGAGACCCGCCACGTGTTGAAGTC 1920
GTGGGAAACGATGGGCACATCGTCGCCGGTGAGTGCGGCATCGAGCTCAGAGAGGTTCCG 1980
CCTGCCAACCTCACCGAGAGCAGCTAACAACGAAGTTTCGGTGCATTCCTGTATCCCTTT 2040
ACCCAGATTATACATGCCCCGGTGTTCGATAACTTGAAGAGGCAGTGGCTCCTCAAGATG 2100
TTCAAGGAGGTGGGGTACAGAGTGCCGGGCGAGGACCTCATCCACCGTGACACCAACCGG 2160
GAGATCCCATTCGAGTTTCCACTGGGGCCAGCATGTGCCCGCGACGGCGAAAGGTTTGCG 2220
CTGGCAAAGAACCCGGCTGCTGCAGGTGGACCTATCCTTACCCATGGCAATGGGGTTTTG 2280
CTAAAAAGTCAGGCACTTTACTGGGCAATTGATAGGTGGGATTGCGTTATTAACTGTTC 2340
TCCAGCGGGAATCTTTATCTTTATTGAAATGCTAAAGCACTTAGATAAAATACAGCTGTA 2400
CCGCAATATAAAATAGTAGGATAATGTAATATGTGTATCGAGAATACGACAAGCTAATAT 2460
AATCTAGCGTCAAATTGCAATAATTTAAATCAAAACTACTGATGAAATAATAAAAGATGG 2520
TCAATTTTTATTGGTAGGAGTTGTCGAAAGATTCGACGGACGGCCATTACAATACATAGG 2580
TGCAAGAAGTAAAACAGGAAGGGAAACGGAAAACAGTGCTATAAAAAAGCGACAGATCGC 2640
GGCGATCACTGACTGCGATCGGGAAGAAGCTCGCCAAGTTCACCGAGAATAGCAGAGAGC 2700
GCATCCTCATCGGGTACTACGAACACATTCGTCCCAGAGGGCTTTGTTTCAGCTGCGCCA 2760
ACCCAGAAAGCAAGGCCATTTTCCAAGTTGCCGATGGCGGTCAGCATGTTTTGATTGTTG 2820
CTGCCGTTTCCACAAGCGATGTGAAGGCCGATCCCGTGAGAGAGGCCCTTGACGAAGGTG 2880
AAATAGCCTTTGGATTTTCCAACTGTTTCAACGGGCACTAGATATTGACCCTCTGGCGCG 2940
GCAACCACCTTGAATTTGCGAGATGACTGGTTGCCGATGAGCGAAGAAAGCATTTCTCCG 3000
GCTTCTTTGTAAGATTTGTGAGATTCCCACATTTGACAGCCGTAGAAATGCCCCATCGGA 3060
ATGTTGCGGATTCCCGGGATGCCACCAAATTTGTTCTCCATAGCCGCGTGAACGGCTTGC 3120
```

Figure 2B

```
CAGTTGGGCAGGGAGAAAGAATCGAAGCGATCATCTTTGTAGATCGTGACCATTCCATCA 3180
TTTCCCTGGAATCCGATATTTTCAATGGCGCTGAAAACTGACCTTGCGATTTCTTCGCAT 3240
TCCCGTGCGGATGTGAGCAATTGATAATGGCCCTTGCAGGGGATCCTGGTCAAATTGGCG 3300
ATGATGTTGATGGCAGGATTAATATCCCAACACTGGTGATTTCGATCTTGCTTAAAGGTG 3360
GTACCATCGCCGTCGAAGGCGAGCAGGGCCCGGAGAGATGAATCGGCAAGACTGCGTCGG 3420
ACCCGCTCCGCGGCGTCGGGAATGAGGCTGATAAGAGACATATCCAAAGGTGTTTGTGGG 3480
TAACGGGCTGCTCAATGAAGCCTTAAATGCAACGCAACATATGTAAGGATGAGTTGACTT 3540
ATTGGAGAGAGAAATAGGAATGAGCTGGCCAGCCATTATCAACGTGGGGCCATGCTGACA 3600
ATGTTTACGTGAAAGGCTCAACTACCTCGAAGCAGACCTCTATATTCGTTGACTTTATTA 3660
CTGAACAAGAAGTTGCTTGCCACTCATTTTCTTAAATCTTGCCCTTTCTGCGCCTCGCTA 3720
TCATGCCCGCCAACGACGCGACATGCGCTGCCGCGATTGCCTTCCCCGAGGGCAACTGGA 3780
AGGAAGAACTTGATGCGCTCCGCACCTTGTGTGACCCCGTCGAGGTGGTTAAGGTCGCAG 3840
TCGGCAGAGGTCTTAGCGGCATATGTAATGTTGTTGCAGCAATGAATCCCACAAAGGTGA 3900
GGGGCCTCGGCGATGTCATCGGGCAGATGCCGGCTCTTAATCACCGTATTGCTGCCGCCG 3960
CCGGCGAAACTCCGGTGCGAGACCTTGGAATAGGTTACCAGTGCGCAATCTGCCACCCCG 4020
ACATAGCCAGTGCGATGTTAGCCACTTCTGAGGGGATCAGCCACGTTCTCCGTGAAAGGA 4080
TTGAGAAAGAAGTTGACCGGGACATTGGAGAAGGCGCCACCGTCTGCATTTTCGTTCAGC 4140
CGAGAATGAGCTCCAAGGGCTCTCCAGTTTCTGTCCATTTCACCCTCCAGTTTGCGAGAT 4200
CTGGAACTCTTGTCGATGCCAGAATGATGGAGAGTTACAATTTCATGAAAGGCAATGGCA 4260
CAGTGACCGCACCGGATTTGAAAAGTCATTGGAAGAAGCACGGTATTGACAGGCCAGGCC 4320
CACGTCCGCCCACGTCCAAGTTTGAACTCCTCTTCGCCGCTGTCCCCGACAACAGTAAAC 4380
TTGCCGCCACCGATTTTACCCATCTCGGCCCTGTCGAGCGTGATAAGGAACTACTCGGCA 4440
GCACGGTATTCGGGATTGCCGCTAAGAAACCTGGTACGATCGTTTATCCGTGCGAAAAGG 4500
TTCTCTGTTTGGAGGTCGACGTACACGCGCATCGCGCCCTAGAAGTACTTCACCGCCTTG 4560
GGGAACAGGCTTATAGCAATGGCCGTGGCACTAGCTTCGGTCTTCACACCGGTCCGTCTT 4620
CTTGCCTTAATCTTTCCGCCGCCGCGCTCGCTACATTTTTCAAACGCTCGGATCTCTGTT 4680
```

Figure 2C

```
CCCTTCCATTGAGTGATGCTTTTGTCCTTTTCTGCGACCCGCCACCGCCTACAGCGCCAA 4740
GAAAGATGGCCTTCCGATCACTGCCTTCTCCCCACGAGCACCAATCAGTTCGAACTCGT 4800
AGAGCCTCAGGTCGTCAAGGCATATGTTCTCGGACTTTTCGACGCGCCGACGATGGTTAC 4860
GCCCCGCGACAAAACGCGAGCCAGCTTCTGCAGCCAATATGTACGTTTCCGTGAACCGCA 4920
TCCCTGTGAAGAGTTCAATGAAATTGGAGTTTTGATCCTCGATGCTGCTGCTAAAATGCT 4980
CGAACGTTATGCAAAATTTCTAGAAGATGGTGGAAGAGATGATGATGAAATGGCGAACAT 5040
AATAGATGTATTTGGGTTTTGTCTTAACTAGTGGATTGATTGAAACAAAGGAGTCCGAGT 5100
TGGGATTCCCTTTCGGTCTTCGTCGTGCAACGATATCGTATGCGTACAGGTATCACATTT 5160
AACGTTGCTGCGGCGGACCGAGCCCGCTTGGAAGCGATTGTTGCAGCTCCAACTTCTGCT 5220
CAGAAGCACGTGTGGCGAGCGAAGATCATCTTGATGAGCAGTGATGGCTCGGGAACGGTC 5280
GCGATCATGGAGGCAACCGGTAAATCCAAAACCTGTGTCTGGCGCTGGCAGGAGCGCTTC 5340
ATGACTGAGGGCGTCGATGGCCTTTTGCACGACAAGAGCAGACCGCCCGGCATTGCGCCG 5400
CTTGATGGCGAACTCGTTGAGCGTGTCGTCGCACTGACGCTTGAGACGCCTCAACAGGAA 5460
GCAACGCACTGGACTGTTCGTGCGATGGCCAAGGCCGTTGGGATTGCAGCCTCTTCGGTT 5520
GTGAAGATCTGGCACGAGCATGGTCTTGCGCCGCATCGCTGGCGCTCTTTCAAACTGTCG 5580
AACGACAAGGCCTTTGCCGAGAAGCTTCACGACGTCGTTGGCCTCTACGTCTCGCCACCG 5640
GCCCATGCCATTGTCCTGTCCGTCGATGAGAAGAGCCAGATCCAGGCACTCGATCGGACG 5700
CAACCGGGACTCCCCTTGAAGAAAGGGCGCGCCGGCACAATGACCCACGATTACAAGCGC 5760
CACGGCACCACCACCCTATTTGCCGCCCTCAACATCCTCGACGGCTCGGTGATCGGCCGA 5820
AACATGCAGCGTCACCGGCATCAGGAGTTCATCCGTTTTCTCAACGCCATCGAGGCGGAA 5880
CTGCCAAAGGACAAGGCCGTCCACGTCATTCTCGACAATTACGCGACCCATAAGCAGCCG 5940
AAGGTCCGCGCCTGGCTGGCAAGGCATCCGCGCTGGACCTTCCACTTCGTCCCAACATCA 6000
TGTTCATGGCTGAACGCCGTCGAGGGATTCTTCGCTAAATTGACACGTCGACGTCTGAAG 6060
CACGGTGTCTTTCATTCCGTCGTTGACCTCCAGGCCACCATCAACCGCTTCGTCAGAGAG 6120
CATAATCAGGAACCAAAGCCGTTCATCTGGAGAGCAGATCCAGACGAGATCATTGCAGCC 6180
GTCAAACGTGGGCACCAAGCGTTGGAATCAATCCACTAGCGTATGAACAGTAATAAGAAA 6240
```

Figure 2D

```
ATCCCGATTGTGAATAGTCCCAATTTCAAATGTGTCCGTGTGTAATTTGCGTGTCTTCAG 6300
TTGAATTTCCTTTAATAATATCAAATATTCAATTGTGAAAAGTTGTATTGGTTCAGGTTC 6360
AAGCTTTCCGAATTTGTTGAATTTTATTCCCTGTTTTCAATTTGTTGACTTGTTTGGGAG 6420
ACACCTTTTTGTGTTTCGTGAACATGTCACCCCTTCGGTATACATTAGCCTACAAAGTA 6480
AATAACGTTGATAAATGTCACTCATGTTGTAATAAAATTGAGCTTATTATGTATAACCAG 6540
ACCCTGTGTTAATCTAATTACAAAGAAATTCATCATTCTCCCAAGCAATCCTGAGTAGCT 6600
GCGTGATGGATCTTCCATATCAGCGCCCACGTTTCACCCCGTTTGCCGTCACCCATCCAC 6660
GTAGTGGAGTCAACCTGAACCGTGCAATTTCTCAGGCCTTTGTCTGCTATGATCAGTTCT 6720
GCGAACGGCTCTTGCGATATCAGCAAAGCTGGACGGATTGGGTGTTCGACCACGGATTTG 6780
CAGAAGCCATTGAAGACGTGGCGCTGGTGTTCCAGGTTGCACCTTGCCTTCATGGCCCCC 6840
GAATAGGCGCGCTCGAAGTGTTGATACCTCGTCGCACCCAGGTCTTCATTTATATGTCGA 6900
ACAACCAATTGCAGCGCTTTGTTGCACACCAGTGCATTGCTCAACTTGGCGACGCCGTGC 6960
TTGCTTGCATGATCCCGCCCTACGCGAGTGACCTCTCGCTGCAGGAAATGGCTCGGGCGC 7020
ACAACAGATTTTGCCCAGGCAGTTACACGAGGTCCGCAGACGTACAGTGCTTTATCGCCA 7080
TCCAACTCAGCAGCCGATTCGTTGAGGAGGGCACATGTAACGTGCACGGGCGAAATGGCT 7140
TAAAAAGAACCTGCCGCTTCTTTCGTCGCCCTGCTGAGTTCTTCAGCCGTTATGACATCG 7200
TTGCCATTGGGCCGGTGCTCTTCCATGATGAACTGGATTGCCCAGCAAACTGCAATGAGC 7260
CTCTTTCCTGCTTTGACCTGCGGTACGACTATCAGGTTTTCCTCCAGGAGTGCGATGCCC 7320
ATGATGGTGTGGGGCATTATCCGGAAGGCGCACCACTACCTAGTGTTGCCATCGTAGGAG 7380
GCGGGCTGTCTGGCCTTGTTGCTGCCACAGAACTACTTGGCGCTGGCGTCAAGGAAATCA 7440
CTCTTTTCGATACCGTTGATGAGATCCGTAGTTTTGGGGCATCGCCGATGCCAAACGGCG 7500
ACGCTCACCAGGCCTTGACGTCGTTCGGTGTCATGCCTTTCTCCGCCAACCAACTTTGCC 7560
TGTCATACTATCTGGATAAGTTTAGAATTCCGTCCAGCCTTCGTTTTCCTTGTGCCGGCA 7620
ACGACCACACAGCACTATATTTCCGCCAGAAACGCTACGCATGGCACGCGGGCAAGCTC 7680
CGCCGGGGATATTTCAGCGGGTACATGTCGGATGGAAGACACTACTCTACCAAGGGTGTG 7740
AACGGAATGGCAGGAGACTGATGGCTCCGATGGATATCTCTTTCATGTTGAAAGAGCGTC 7800
```

Figure 2E

```
GTCGTGATGAAGCCTCAGAAGCACGGCAGCTTTGGCTCCGAGAGTTCGGAAAATTCACTT 7860
TCCATGCCGTTTTGGTCGAGATCTTCAGCTGTGGTAATTCGAGTCCTGGTGGCAAGGCAT 7920
GGCAAACACCCCATGATTTCGAGGCTTTCGGGATACTGAGGTTGGGATACGGCCGAGTTT 7980
CGTCCTATTACAACGTGTTGTTTTCAACGATCCTGGACTGGATTATCAATGGCTACGAGG 8040
AGGACCAGCATCTTTCTATTGGTGGGGTTCAACTTTTGCAGGCTCTGATGCGCATTGAAA 8100
TATTCCAGAAAAGCCATGCGAAAGCACGACTCTGTTTTGATCCCGTGCGTGGAATAGCCA 8160
AGGAGGGCGGGAGATTGAAGGTATGCTTGAAACACGGTCATTCGCGTGTTTTTGACCAGG 8220
TCATCATTGGCGGCAGTGCTGAGGCCGCTACAGTTGATAACAGACTGGCCGGGGATGAGA 8280
CTTCCTTCAGCTACAATATCGAACCCGCCGTCGGAAACTCGTCTGCCGCTGTCAATTCAG 8340
CACTCTTCATGGTCACGAAGCAAAAGTTTTGGGTTAACTCCGGCATCCCAGCAGTGATAT 8400
GGACCGATGGGCTTGTCCGTGAGCTGTGTTGCATTGACATCGAATCGCCAGCTGGAGAGG 8460
GCCTTGTCGTTTTTCACTATGCTTTGGATGACTATCTATCCCGGCCGATCGAGCATCATG 8520
ACAAGAAGGGACGGTGCTTGGAATTGGTCAGGGAGCTTGCTGCTGCCTTTCCTGAACTGG 8580
CTTGTCACCTGGTCCCAGTCAACGAAGACTACGAACGATATGTCTTCGACGACCACCTAA 8640
CGGATGGTTTTAAGGGAGCTTTGTGGAGGGAAAATTCTCTGGAAAAAGGTCAGTATATCC 8700
AGGATCTGCCTGGGAATAATTTTCCTATTGGGGATCACGGGGGAGCCTATCTGATTGACC 8760
GTGACGACTGCGTCACCGGAGCCTCGTTCGAGGAGCAGGTGAAGGCGGGCATCAAAGCGG 8820
CCTGCGCCGTCATCCGCAGCACCGGCGGGACGCTCTCTTCACTCCAACCGGTGGACTGGA 8880
ATAAAAAATAGAAATTTCCTGATTAAGTTATAGTCAATGTACTATTGCGTGTTAATCCCG 8940
TAGGTATGCAAGCTGCACCGGCAGCATCATAATTTGATGTTCCATCAATAAATTAAGGTG 9000
CCCGTTCATTGTGTATTACATTATGTATGTTTATCAAAAATATAATCGAAGTCCATTTTA 9060
AGTCTGATATTAATTGGAATTCCAAACGATTCCTTGATGCCTATCTTCGCTATGATTGTA 9120
TGGTAATAAAGTCTCCACATCTCCCGAAAAATGCTTTCGTGATTTACTTGTCTCTCACGT 9180
GCTTTCGCATCTTGACAGCCAAAAGTGGGCAACTTGAGAAGAGTATTAACTGGCCACGCA 9240
ACTCGAGATATTCCCACTAACCCCAATGACGTCATTGCACTCGTCACGGGTAGCAGCCCC 9300
ACTTGCCTTTGCCACTTTATTAATTCTTTGGCCCACTGGCCATTAATTGGCACCTACATA 9360
```

Figure 2F

```
TATTAGTGGAGAAGATAAAGTGTCACTATCGTTTCCTGTTCAATTTTGAATTTTGCAAGG 9420
ATTTCATGTTGTCAACTACACAGCTTGAAAGGAAATCCGCAATCAACGGAGAAACGTCAA 9480
CATCTCGACAAAAAAGAATGCTTCATCATTGCGTAGACTGCATATTGACCGCTCCTTTC 9540
GGCGCTGGGCCTGCTTTTACTGTTGCCTAGCGTTCGGACAGCCACCAGAGAATGGGCTAT 9600
ATAGATCCTTTCATCAAACCAAAACATTACTAAGATCATGCTGTAACGCTTCAATACGGT 9660
GAGTGTGGTTGTAGGTTCAATTATTACTATTTTTGAAGCTGTGTATTTCCCTTTTTCTAA 9720
TATGCACCTATTTCATGTTTCAGAATGGAATTAGCCGGACTAAACGTCGCCGGCATGGCC 9780
CAGACCTTCGGAGTATTATCGCTCGTCTGTTCTAAGCTTGTTAGGCGTGCAAAGGCCAAG 9840
AGGAAGGCCAAACGGGTATCCCCGGGCGAACGCGACCATCTTGCTGAGCCAGCCAATCTG 9900
AGCACCACTCCTTTGGCCATGACTTCCCAAGCCCGACCGGGACGTTCAACGACCCGCGAG 9960
TTGCTGCGAAGGGACCCTTTGTCGCCGGACGTGAAAATTCAGACCTACGGGATTAATACG 10020
CATTTCGAAACAAACCTACGGGATTAATACGCACGTGGCTGGCGGTCTTCGATTCATTTC 10080
CACGCCGGAGATGATATCGAATATGTTCTGTTAAGTTAAAATAAGCTGCGAGCCATGGCG 10140
CGATTGTCCTGTTTTATTAATATAGTACTTTAACGTCTCTTTAGAGCGTTTGTGTAATGT 10200
CGTGAAAATGTTTTATGTCAAATGTACTGTTGAACTATAATATTATAAGTCCAGGTGTGT 10260
CGTTGTTGTTGATACTGCAATATATGTGTAGTAGATTAGATAGTCATATGAGCATGTGCT 10320
GTTTTTGGCAAAATTCAGCAGCAGGATCAACACAGAAGAAAATATTTAGTACAAGAAAAT 10380
AGGTCAACACATTACAACGTACGCTACAACTCCCAAGGTTCTGTGTCACAGACTGCGGGA 10440
GGGTACATAGAACTTATGACAAACTCATAGATAAAGGTTGCCTGCAGGGGGAGTTCAAGT 10500
CGGCTTTAGGCTTCTTTCTTCAGGTTTACTGCAGCAGGCTTCATGACGCCCTCCTCGCCT 10560
TCCTGATCAGGCCCCGAGAGTCGCAGGGTTAGGTCTGGCTCCGGTGAGGAGGCGGCCGGA 10620
CGTGATATCCCGAGGGCATTTTTGGTGAATTGTGTGGTGCCGCAAGCTACAACATCATAG 10680
GGGCGGTTTTCAGTCCCTCGCCGCAGAAAGAAGGTGCAAGCTACCTCTCTCCCGTAAACG 10740
TTGGTCACTTTTAACTCCAGCAAGTGAATGAACAAGGAACTTGCGAAAATGGCGATGAAG 10800
CATTCTAAATCAGGTTCCTCCGTGCGGCTGTGCGGCCAAGCAAGGTTGTGAACACGGAGC 10860
ATCTCCTGGAGGGCGAGCTCGCTCCGATATGGTTGAATCGTTGTCGCCAGCACGGCCTCC 10920
```

Figure 2G

```
ATTCCAAATGTAATGGATTGTTCCTTCAGCACTTTCTGCATCTTCTCGCGAGAAAGATAG 10980
ACAAATACATGTTGGTCGTTTTCTCGAGCCAGATCCGGCTGACTAACAAACATAGGAGGA 11040
TGATAGCAGACTTTGTTCTTCAAGAGCTCAGCTAGTTGTTTAAGTATATATATCGGTGGA 11100
GAGTTTTCCTTCAAATCTAGCACTGCAAGAGCCCATCGTTTCTGGAAATGCAGGAGGGT 11160
TTGCTATAGTCACGGCTATAGATTGCAAAAGCAAATCGGATCCCCTCGAATAGGTTTATC 11220
TGGCTCCATGCTGGAGTGAGATCTACTGGTTGAAATCGTGGAAGGAATAGCAATTTGGGA 11280
TCCATTGTGATGTGAGTTGGATAGTTACGAAAAGGCAAGTGCCAGGGCCATTTAAAATA 11340
CGGCGTCGGAAACTGGCGCCAATCAGACACAGTCTCTGGTCGGGAAAGCCAGAGGTAGTT 11400
TGGCAACAATCACATCAAGATCGATGCGCAAGACACGGGAGGCCTTAAAATCTGGATCAA 11460
GCGAAAATACTGCATGCGTGATCGTTCATGGTTCATAGTACTGGGTTTGCTTTTTCTTG 11520
TCGTGTTGTTTGGCCTTAGCGAAAGGATGTCAAAAAGGATGCCCATAATTGGGAGGAGT 11580
GGGGTAAAGCTTAAAGTTGGCCCGCTATTGGATTTCGCGAAAGCGGCATTGGCAAACGTG 11640
AAGATTGCTGCATTCAAGATACTTTTTCTATTTTCTGGTTAAGATGTAAAGTATTGCCAC 11700
AATCATATTAATTACTAACATTGTATATGTAATATAGTGCGGAATTATCTATGCCAAAA 11760
TGATGTATTAATAATAGCAATAATAATATGTGTTAATCTTTTTCAATCGGGAATACGTTT 11820
AAGCGATTATCGTGTTGAATAAATTATTCCAAAAGGAAATACATGGTTTTGGAGAACCTG 11880
CTATAGATATATGCCAAATTTACACTAGTTTAGTGGGTGCAAAACTATTATCTCTGTTTC 11940
TGAGTTTAATAAAAAATAAATAAGCAGGGCGAATAGCAGTTAGCCTAAGAAGGAATGGTG 12000
GCCATGTACGTGCTTTTAAGAGACCCTATAATAAATTGCCAGCTGTGTTGCTTTGGTGCC 12060
GACAGGCCTAACGTGGGGTTTAGCTTGACAAAGTAGCGCCTTTCCGCAGCATAAATAAAG 12120
GTAGGCGGGTGCGTCCCATTATTAAAGGAAAAGCAAAGCTGAGATTCCATAGACCACA 12180
AACCACCATTATTGGAGGACAGAACCTATTCCCTCACGTGGGTCGCTAGCTTTAAACCTA 12240
ATAAGTAAAAACAATTAAAAGCAGGCAGGTGTCCCTTCTATATTCGCACAACGAGGCGAC 12300
GTGGAGCATCGACAGCCGCATCCATTAATTAATAAATTTGTGGACCTATACCTAACTCAA 12360
ATATTTTATTATTTGCTCCAATACGCTAAGAGCTCTGGATTATAAATAGTTTGGATGCT 12420
TCGAGTTATGGGTACAAGCAACCTGTTTCCTACTTTGTTAACATGGCTGAAGACGACCTG 12480
```

Figure 2H

```
TGTTCTCTCTTTTTCAAGCTCAAAGTGGAGGATGTGACAAGCAGCGATGAGCTAGCTAGA 12540
CACATGAAGAACGCCTCAAATGAGCGTAAACCCTTGATCGAGCCGGGTGAGAATCAATCG 12600
ATGGATATTGACGAAGAAGGAGGGTCGGTGGGCCACGGGCTGCTGTACCTCTACGTCGAC 12660
TGCCCGACGATGATGCTCTGCTTCTATGGAGGGTCCTTGCCTTACAATTGGATGCAAGGC 12720
GCACTCCTCACCAACCTTCCCCGTACCAGCATGATGTGACTCTCGATGAGGTCAATAGA 12780
GGGCTCAGGCAAGCATCAGGTTTTTTCGGTTACGCGGATCCTATGCGGAGCGCCTACTTC 12840
GCTGCATTTTCTTTCCCTGGGCGTGTCATCAAGCTGAATGAGCAGATGGAGCTAACTTCG 12900
ACAAAGGGAAAGTGTCTGACATTCGACCTCTATGCCAGCACCCAGCTTAGGTTCGAACCT 12960
GGTGAGTTGGTGAGGCATGGCGAGTGCAAGTTTGCAATCGGCTAATGGTTAGTCGATGGG 13020
CTGACGAGTTTGATGTCAGGAGAAGCTGAGTGTGTCACTTGTTTCCCTTTAAGAAGTATT 13080
AATGTAATAAAAATCAAGATCTGGTTTAATAACTGGATACTTGATTTCATCGCGCTTTTT 13140
TTGAATAAATGTTTGTTGTCTTGACTTTAAGATATCCTTTGAAATTTGCGTTATTCGTAT 13200
TTCGCTTTTGGTTATTTCCAAAAGACTTTGCTCAGTAAGATCAAACGTTTGTATTTCTCC 13260
GGGCCACAATATTTGACCTATATGCACTGGCCCACGCGCCGCAATAGATGAAAATTGCCA 13320
AAATTAGCTATCGGTCTTCTGAAAAGAAGGGCCGACATGTTTTCATAGACCATGCAAAGT 13380
CATACTACCTGAAACTGATAAATAACGACAAAGAAAGTAGCCTATTTAAAAGTCGCTATA 13440
GCATGAATTCAACACAAGGAAACCAAAAGTCGGAAGGAAGACTTTAATCCCGGATTATTT 13500
GGACATGATAGGAGCTATGGGGCAACGTGTCATTTTCATGAGTGTTGAATGATTTTCTGT 13560
AGCAAATAGAAAACGTTTTTTAAAACGATGTGGCCTTGGAGTAATCAGCGGAAGAAATGG 13620
TCATGCTCAGATAATTTCCGTTGCTGACCTCGCAACCAACCCCTTTAAATACCTCTGCTG 13680
CCCATGCATTTTGCCAAGTTAACCTAAAGTGGCAGCTGAATGGCTCGTTATTGCAGTGGT 13740
GGCTCTCAACGGCTTCATGTCGATGATTTTCGTTGGATCAAGGAGCCCACTCGACTGAAG 13800
GCTCAGCTTATTAATGTGGTGGAGACCTACAAGGCTGCACAAACAGAGACGTTAAAGTAC 13860
TATATATCATCTGCAACTGAGCGTGTGGCTCATGTGGAGGCAGCCGAGGTCAACAATGCG 13920
GAAATGGAGCTGCATCCTGCTGGGTTGAAGTACCCTCTGTCCTTCGTCTTTACCTCCCTG 13980
GCCGTGGCTACAGCCTGCAAGGAGAACAAGCATCTCTTGTGCGAGGAGCATTTGGAGGGG 14040
```

Figure 2I

```
GACTTGATATCGTGCGTCGTTCCTCCCTATCAGACAAATGTCTCACTCGCTGCTTTAAGG 14100
GAGCTCCACAATTCCATTTCGGGAGGAGGGTACCAGGAACAAGCAGACATGGATTATTTT 14160
GTGGCGATCATCCCAAATGATAATTTCGACTATCAGAGCTGCGAAATCGACACACGAAGT 14220
TGCGGTAAAGGACTTTGCAAGATTTATAGTAGGGAACTGGGAGGGCAGCCTCTAGCTTAT 14280
GACGCCATACTGGCAATCGGCAAGGTGCTGCTGCTGGAATAGATAGTGGGCCGCTGATCC 14340
GAGTTTGATTTTGTCGTATTATGTTACGTGAACTTTTATCATGCATGTTTCGCTTATGC 14400
TCCCGAGTGTCGGCCATGTTGTTGTGTTAAAATAAAAGGCTGATGTTAAGTCCTATTGTA 14460
AAATACCTTTATAGATTAAATATATATAGTATAACTTCTGTATGCCGTCGATGAGCGGTT 14520
ATATGATTGTAATCTATACGTTGTTGCAATCAATCGTATTACAGTGAGCCGTGCTTAATG 14580
GGGGAAACGTAATAACATTGCGGTGGATACAGCGTTTATTGGGAGGTCCGCGGGCCGATA 14640
CACTTAAATAACATAGACAGAATTTGAGAGAGCACGCAGGTTGTAGCCAAGTTGAGCGAC 14700
TTGCCGGTAGCACGGAAGCTAAGCTCAGGTGTTACAAATAGACAGGCGTCGAGGCGACGA 14760
TTGCCGGTAGCACGGAAGCTAAGCTCAGGTGTTACAAATAGACAGGCGTCGAGGCGACGA 14820
GCACGACGACCTTGCCGGACATTGCGGTCGCAGGGGCTCAAAGCGGTTGGCTTGTAACG 14880
GACCTTGTGTTTCTTGTTGTAGCTTTCATCGAGCATAACCATTGGGACGGTTGCTGAACA 14940
ACGGTAACGCACTTTTTTCACGGGAGCGAGGTAGAAGAACATATTTCCCCGTCGGCAGCC 15000
GGCGGTGAGCATGCCAATTCCTAAGGGATCAATGGACTCGTGCGAACGGTGAGCATGCCG 15060
TTCTGACCGTCGGTGCCCAATCAGCAGGCCACTCCCAACATGTTTTCCAAGTCCTTAAAA 15120
CCAGTCTTTATAGCATTGATCTCCCAGCAATCTTTATTGAAGTCGATTTTAATATTCAAA 15180
AGAAGATTTTAGTGGAAAGGGAATATAATCGCGTGGCCGAAGAAGAGCCTTCAAAAATCA 15240
GAATCCACTAGGATAAACAATAATATCTGAAAAGCATTGAATTTGGGTTAGGCACGAGAG 15300
GCTGACGCGGATGCCACTCGATTGCTAGTGGAAGGATTCCCTTTTTTCTAGCGTATCGAA 15360
TTCACCGTTTCACTATATGTTTTCCTGATTGGTTGATCTGCGGGACCACCATTGACTGCC 15420
ACTAATATCGAAAGTGGGTCTGCTTCGATTATGATGCTTTGTGAGAGGTTCTCTTCCCAA 15480
TGCATGCAAGCTGGCAGATTCGGATACTCAATAGAGATCTTATTTCGCGTCTCAAAAA 15540
GTTCCCAGAAATCAACAAAGGGGAGGGCAGGTCCTTTAAATACGTTGCAGCTGTCCTTTA 15600
```

Figure 2J

```
AAATAGAAGAGAATTTACAGCTGGAGGCACAGACCACTAAACTGCGAAAGTAAGCATGGC 15660
AGATGAGTTGGAGCGTCAATTGGAAGCCATTTCTCTCATTACAGTCCTGGGTCCGGATGT 15720
GAAGGCTGAGCTTGAGGCGGAGCTACGAGACTACTGCGAAGATCTCGACTTCTGGAAAAG 15780
CCACGGTTTACCGGTGGCGGATCTCGATCAGACTGTGACTGTCGACAAGCTTCTATACAT 15840
GTATATGGATCGGGCAACAGCAGACCTGTGTGTGAAGAATCGCTGCCTCGTTTGCAACAG 15900
TGGCAATTCAGCCGCAAAAGTAACCTCGCTTCCACCATACCTTGCAGGCGTGACAAGCGC 15960
CGAGGCCTATGAGAAACTCAACTCCATTGTTGATGGGAGTGTCGCCCCCAATCTCGTGG 16020
GCCTCCCTGCTATTTTGTGGCGTTCCTGCCCAGCAGCTGTTTCGAGAAACCAGTGAGAT 16080
ATCGGTGCGCACAGTGGACGGCGAGTGTGGCCCCTTCGATGTCTTTACCCGGCAGCGTCA 16140
GCCACAGGATCAGAGTGATATGTTTTTTAAATATGAAGGAGTTGTATGTGCTGGAAAGAG 16200
TGTATTTATGTAAGAATTATCTTTTATAGCCTGTGTTACGTTTGAACCCGGTCCGCGCGG 16260
TATTGTTTTCAATAAATGGTATGTGCGGAGGATATAATTGGTCTTTCATTGGTGTGATTT 16320
ACGTGTAACGCGGATAATAATAAAGTAAATTACAAAAGAGAAACGCATAATTTTATTCCA 16380
GAATGATTGCGAGAAACGATGAAAATACATGAAAATGCATATTGTCGCCAGGGAAGGATG 16440
GCGCCGAAATAAACGAAACTGAGCCAATACAGTGACTTGCCAAGCGAGTTTGATCCTACC 16500
AAATTCGCGCAAATTAATGCCCGTGTTCCATCGGGCCAGCGAGTTTATTCAAAAGAGTTT 16560
CGTACACGTGGGCGGCGACGGCAACGTCAATGCTTGCTAGCCCTACCGGCGAGAAGTTGG 16620
CCGGCCCCTTCCATGCCTTGAGGTCATTCATCAAGGCCTCGTCATCGAGAATTTCGGTGT 16680
AGTTCTTGATCCCATCGCGCTTGCCGTGTTGGGTCAGTTTCATACCGCGCCTAGAATAGT 16740
AGAGGGCAACGGCATCAACGTTGCGGGCTTCCATCGCAACAAGGTCATCGGCGACAATTA 16800
GACCATCCGCAGATAGGACATGCTCAATGTAATCCGGCGGCATGTCATCAATACCGAGTG 16860
ACAAAGTGACTGCGTTGGGGGCGATTTCAGCGGCTTCGAATACCGGTTTTCCGTAGTTGG 16920
TCGCCATGATGACGAATTGAGAATATGGCAAAAGGCTACGATCGCCGACAGCTTCAAGGC 16980
TAAAGGTTACGCAATCACGTAACTTTTCGACGAGCTCGAAATTGGATTTCTTACCGCGGC 17040
TGAGCACTGCTACCTTACGAATTCTCTTAGCGGCACCATAGTTAAGTGAGAGAATTACAG 17100
CTTCGGCAACTTTTCCAGCCCCAAACAAGAAACGTCGATGTCCTCTCTGCCTTGCAACA 17160
```

Figure 2K

```
GCAGGTTTACGCATGCTAGCGAGAACCAACCCGTTCTTCCATTAGAAATTGCCACGCCCT 17220
CTACCGACATAAGGAGCGTCCCGGACACCTTGTCGCGCAGGAAAATATCGGAGTGCTGGA 17280
GCGGCTTTCCGGTAGCGGCGTTGGTTGGCGCGAAGTGGATGTCTTTGGTGCCGGAATATC 17340
TTCCGAAATAGCCAATGAGTGCTCCTTCAGTCCATCCAGGAACATTCTTGTTGAACGTTA 17400
GGTAAGCTTTGACATGTCCGGCTTTTCCTGCGGCAAACACCTCCCAATAGGACTTGAGAG 17460
CTTCGTCAACAAATGCTGGTGTGATCTGGATATCGAGGTTTGATAGTGCAGATTCAGTCC 17520
AGTGTACCTCGCAAAGTTGTTTGGCCATCTGCCTTGTAGGTGCGAATTTTCTCTGCTCAA 17580
ATTGTTGAGGTTAGCGGATTTGTAAACGCGTTTATATGGCTGCTTGGAGGGTACTTTTG 17640
GATTAATTTTTTTCTGCCAGCGCATTCTGACGCGGCACCGCTTTGGAAAGTGCGCTGTGG 17700
GTCCGCGTTTTCTACAATAATGTGCCGATCCGGTCAGAAAGTATATGGATGAGTTGTGCC 17760
AGCCTCACCAACGTGCTGCAGGCCCATCATGACTACTTCAATGTTAATGGGGGTAATGAA 17820
TAAATAGGCGAAATTGGGTTCACGGTGGGCCCAGGGAATATAATATTGCCGCAGAGGTAG 17880
TCGGATGCCAAGGCCCGCAACTAATAGTTCACGAACAAATTCATTGTAGTGGGCGGCCAA 17940
CTCCAAAACCAATTGCCAGTTATTGTATTGCAATACATATGAGTATTCGGATACAACT 18000
AATTTCATTAAATAATATTTTAAGTGTGGACAGAATAGCGCCTAATAAATTTGCGAATGT 18060
TGTCCAATTGACGTTTTTATAGGTAACTCGATAAATCGTGCTTTTGTGATATTCTGATGC 18120
GGACAATATACATTTAAACATAAGATATAAGTTATTGAGGCATTTATGTATATTACAAT 18180
AGTGGGGTACATTTTTCACAGATGCTGTCACCCATGAAATATTGGCAAAATACTCTTAAA 18240
ATATGCAAGAAACTAAAGAGGATGCATGGGTTGGGCTGTAGGTACATGGATGCAAATGCT 18300
GTTTTGCAATAAGTCATATAGTCTCGTCTGTTGAGTGAGGCCCATTCAATCAGCAAGTAG 18360
GACTGAGGTGCATGATCGACATATTTTGAACCACAGTTTTGGCAAGTTTTCATACAAA 18420
TGCACGGCTACGGCCAAATCGTAGCTTGCAAGTCCAACTGCTGAAAAGTTAGCCGGCCCG 18480
TTCCAAGAAATTAGCCTTTGCATAAGGACTGGATCGCGGAGAACTTCAGAGTAGTTCCTG 18540
ATCCCATTGTCCCTGCCGTGTTTTGTTAGCTTTAAATGGCGTCTTGAATAGTGCAGCGCC 18600
AACGAGTCGATATTACGTGTTTCCATCGCATCCATATCATCTGCCACCACGATGCCACTC 18660
AGCTTCAACACGTGATCAAAATAGTCAGCTGGCAATTCGTCAATTCCAAGCGTCAATGTA 18720
```

Figure 2L

```
ACGGCATTGTCTGTGATCTCCTTCATCTCAAAGACGGGCTTGTTTGAATTCGTCGCCGTA 18780
ATTATGAACTTGGATTTGCTGAGATATGCTCGATTGTTAACAGCCTTGAGTGAAATCTTG 18840
ACTTCCGGCTGAAGCCTTTGCACCAACTCATGGTTTGACTGGTTGCAGCGGCTGAGAATC 18900
GCGATTCGTTGAATTCTTCCAGATGCTCCCGAATTGAGGGCGAGGATGATGGCCTCGGCA 18960
ACTTTACCTGCTCCGAATAGGAAGACATTGATCTGGCTTCGGCCCTGCAATAGGAGATTC 19020
AGGCATGCTAGTGCCAGCCAACCAGTTCTCCTCTCCGATATAGCCACCCCATCAACAGAG 19080
AAGAGACGTCTACCTGTGAAACGATTGCGAAGCCAACGTCGATGTGAGAAGTCGGTTCTT 19140
TGTATCTCGCGTTTGACGGATTAGAATGGATGCTTTTCACACCCGAATAGTCGCCGACGA 19200
AACCCACCAGAGCTCCCTCCGTACAGCCCTCTCGATCAAGTGGAACGAAGACCTTGTTGT 19260
GGCCGAGCCGCCCTTCAGCAAAGAGGTGCCAATAATCTTTCAAGGCATCCGCGACGAGTT 19320
CCGGTGTAATGTATATTCCAAAAGCCGATAGAGATTCCTCTGTCCAACATTGCTCGTGTA 19380
TTTGATCGGCCATGTTTGTGTTTGATCAGCCTCCTTTCGAAAATTTCTTGAGTTTCGAAT 19440
AATTCTAAAATCGAAGGACGATTAATAGTGCCATACCAAGACAAGAAGGGTAGGTGGGCC 19500
ATCAATCCACAAGCCTAGCACATTTTGCTGTCTGCTCATGCAAGGTATCCAATGGAAGCC 19560
TGGATTGGTTAGCCGAACTTGGTGGGTTCAATTGGAGCGGGCAGGTCACTTTTTGTCTCT 19620
CAAATAACTGAAACTAAGTTTTGTTATTTGGTATGTGTTTGTCTGTTCTGCCGAAGGTGC 19680
CCGAATTTGCGCAAATTCCTTTCTAAAAAGGCTTACATCTAGCAAAAGGTGAGCCCTGTG 19740
CATCCCAGCATTTGGACAAAGCGCGCCAATTCGGACAGCGACTGGCTGCGTTGGAGGCTC 19800
GGATCTCAAAGAATAGAAAAGAGTTATGATCATGTTCAGAACCGCCAATTTTGTGCGGTA 19860
TGAGCTCTTTGATGAAAGTAATGGTTTCAAAAAAGCAACATCGTGGGTGAAAGGTACCTA 19920
CATATCTTCACAGACAATAACTACTGTTGCTGTTTGCTGATTGACTGACAGGATATATGT 19980
TCCTGTCATGTTTGTTCAATTGTTCAATTGTTCAATTGTTCAATTGTTCAATTGTTAATG 20040
TATAAGTTCGTGATGAAGGATGGTTGTTTTAAAAATAGTATGTTTGACTGAGGTTAAGTC 20100
ACTCACGTTTTGCACATCGACGGACCGTAAGCATTCTTTCGGTAAGACCGAAGCTCGTCC 20160
CAGATAATAGGCCCCGTGGAGGGAGGCCTTGTATGGGCCGACCGATGGGCGTGCTGAGCC 20220
GAGTACGGCGACGCCTGCGGCGATTGCGCGGCGGCACTGCGCGCAGGGGCACGGGTTCA 20280
```

Figure 2M

```
TACGAGGACGAGCGTAAGGGGCATAGAGCTTTCCGCCCGTCGGGTTTCAGCCATATTGCT 20340
TGATTGCGGCCGACTGGAATGCAGCCAGGTCGTGCTCGCCGGCGGCGCCTGGTCGAGCGG 20400
CATGCTGCGCACCTCAGTGTTCGGCTTCCTCAGCTCACGGTTACTGTGTCGGCGCTAAGA 20460
ACCGAGGCCTTTGATGGCGGACCTGGCCTTTTCAATCAAGGGATGCTGATTTTCCATCCG 20520
TAAGCGTCTCGACGGTGGTTACACCGTCGGCTTCGGCGCGACGATGAGAACCGAAATCGT 20580
CAGCGATAGCTTTCGTTTTCTGTCGGATTATTTCCTCCTGATGCGAGAGGAATGGCTTTC 20640
TATCCGGCTGCCGGCGGGTGCGCGCGTCCGGATTGACCCTCCCGTTCGTTGCTACTTGGC 20700
TCGAGTGACGAAATAGCACGCCTGTGCCGCTGTATCATGTCCATCGGGCTCACAGGAGAT 20760
TCGCTCGTAGCGCGTTGGTGTCACTCACCAACACGCGTCGTCGCACCAAATTGGGGAGGA 20820
TGGTAGCGGAATCCTAAAATCCTAAAACCATACCGACGCGTCACGGCGCTCGTGACCCCT 20880
GCGAGCGACGCGGCACTCTCTCACCTGATCCGTGCTGCGGTTGCTCAATACGCAATGAGC 20940
ATTGTCACGGTTCTCAGGGTAAACGGCAATCTCTTCGTCATGCGGGCGTGGATGCTATCA 21000
CCGTTAGAAAGGGCCTGCCCCCATGGTGGGTCTCTAAGGTTCAGTCTGAGAAGGGGCAGC 21060
CAGAGCGGCACTGTTTGAAGAGCAGTCTGAACCGCTCAGATCGCTCGCATCGATGCTTGG 21120
GCGGCG 21126
```

Figure 2N

RI T-DNA PROMOTERS

CROSS-REFERENCE TO A RELATED APPLICATION

This is a division of application Ser. No. 08/336,346, filed Nov. 8, 1994, now U.S. Pat. No. 5,466,792, which is a division of application Ser. No. 08/008,216, filed Jan. 25, 1993, now U.S. Pat. No. 5,366,887, which is a division of application Ser. No. 06/725,368, filed Apr. 22, 1985, now U.S. Pat. No. 5,182,200.

FIELD OF THE INVENTION

The present invention is in the fields of genetic engineering and plant husbandry, and especially provides means for promotion of transcription in plant.

BACKGROUND OF THE INVENTION

Following are publications which disclose background information related to the present invention. These publications are discussed in greater depth in the Background sections indicated. Restriction maps of Ri plasmids are disclosed by G. A. Huffman et al. (1984) J. Bacteriol. 157:269–276; L. Jouanin (1984) Plasmid 12:91–102; and M. Pomponi et al. (1983) Plasmid 10:119–129 (see TIP Plasmid DNA). L. Herrera-Estrella et al. (1983) Nature 303:209–213, provides examples of use of the nos promoter to drive expression in plants of heterologous foreign structural genes. N. Murai et al. (1983) Science 222:476–482, reported the ocs promoter could drive expression of an intron-containing fusion gene having foreign coding sequences. (Manipulations of the TIP Plasmids). R. F. Barker et al. (1983) Plant Molec. Biol. 2:335–350, and R. F. Barker and J. D. Kemp, U.S. patent application Ser. No. 553,786 disclose the complete sequence of the T-DNA from the octopine-type plasmid pTi15955; homologous published sequences of other Ti plasmid genes are referenced therein. Barker and Kemp also taught use of various octopine T-DNA promoters to drive expression in plants of various structural genes (Genes on the TIP Plasmids).

Shuttle Vectors

Shuttle vectors, developed by G. B. Ruvkun and F. M. Ausubel (1981) Nature 289:85–88, which provide means for inserting foreign genetic material into large DNA molecules, include copies of recipient genome DNA sequences into which the foreign genetic material is inserted. Shuttle vectors can be introduced a recipient cell, by well known methods, including the tri-parental mating technique (Ruvkin and Ausubel, supra), direct transfer of a self-mobilizable vector in a bi-parental mating, direct uptake of exogenous DNA by Agrobacterium cells ("transformation"), sphero-plast fusion of Agrobacterium with another bacterial cell, uptake of liposome-encapuslated DNA. After a shuttle vector is introduced into a recipient cell, possible events include a double cross-over with one recombinational event on either side of the marker (homogenotization). Phenotypically dominant traits may be introduced by single cross-over events (cointegration) (A. Caplan et al. (1983) Science 222:815–821; R. B. Horsch et al. (1984) Science 223:496–498); one must guard against deletion of the resulting tandem duplication. Shuttle vectors have proved useful in manipulation of Agrobacterium plasmids.

"Suicide Vectors" (e.g. R. Simon et al. (1983) Biotechnol. 1:784–791), are shuttle vectors having replicons not independently maintainable within the recipient cell. Use of suicide vectors to transfer DNA sequences into a Ti plasmid has been reported (e.g. E. Van Haute et al. (1983) EMBO J. 2:411–417; L. Comai et al. (1983) Plasmid 10:21–30; P. Zambryski et al. (1983) EMBO J. 2:2143–2150; P. Zambryski et al. (1984) in Genetic Engineering, Principles, and Methods, 6, eds: A. Hollaender and J. Setlow; P. Zahm et al. (1984) Mol. Gen. Genet. 194:188–194; and Caplan et al., supra; and C. H. Shaw et al. (1983) Gene 28:315–330.

Overview of Agrobacterium

Included within the gram-negative genus Agrobacterium are the species A. tumefaciens and A. rhizogenes, respectively the causal agents of crown gall disease and hairy root disease of gymnosperm and dicotyledonous angiosperm plants. In both diseases, the inappropriately growing plant tisssue usually produces one or more amino acid derivatives known as opines which may be classified into families whose type members include octopine, nopaline, mannopine, and agropine.

Virulent strains of Agrobacterium harbor large plasmids known as Ti (tumor-inducing) plasmids (pTi) in A. tumefaciens and Ri (root-inducing) plasmids in A. rhizogenes (pRi), often classified by the opine which they caused to be synthesized. Ti and Ri plasmids both contain DNA sequences, referred to as T-DNA (transferred-DNA), which in tumors are found to be integrated into the genome of the host plant. Several T-DNA genes are under control of T-DNA promoters which resembles the canonical eukaryotic promoter in structure. The Ti plasmid also carries genes outside the T-DNA region. The set of genes and DNA sequences responsible for transforming the plant cell are hereinafter collectively referred to as the transformation-inducing principle (TIP). The term TIP therefore includes, but is not limited to, both Ti and Ri plasmids.

General reviews of Agrobacterium-caused disease include those by D. J. Merlo (1982), Adv. Plant Pathol. 1:139–178; L. W. Ream and M. P. Gordon (1982), Science 218:854–859; M. W. Bevan and M.-D. Chilton (1982), Ann. Rev. Genet. 16:357–384; G. Kahl and J. Schell (1982) Molecular Biology of Plant Tumors; K. A. Barton and M.-D. Chilton (1983) Meth. Enzymol. 101:527–539; A. Depicker et al. (1983) in Genetic Engineering of Plants: an Agricultural Perspective, eds: T. Kosuge et al., pp. 143–176; A. Caplan et al. (1983) Science 222:815–821; T. C. Hall et al., European Patent application 126,546; and A. N. Binns (1984) Oxford Surveys Plant Mol. Cell Biol. 1:130–160. A number of more specialized reviews can be found in A. Pohler, ed. (1983) Molecular Genetics of the Bacteria-Plant Interaction, including a treatment by D. Tepfer of A. rhizogenes-mediated transformation (pp. 248–258). R. A. Schilperoort (1984) in Efficiency in Plant Breeding (Proc. 10th Congr. Eur. Assoc. Res. Plant Breeding), eds: W. Lange et al., pp. 251–285, discusses the Agrobacterium-based plant transformation in the context of the art of plant genetic engineering and plant improvement.

Infection of Plant Tissues

Plant cells can be transformed by Agrobacterium by several methods known to the art. For a review of recent work, see K. Syono (1984) Oxford Surveys Plant Mol. Cell Biol. 1:217–219. In the present invention, any method will suffice as long as the gene is stably transmitted through mitosis and meiosis.

The infection of plant tissue by Agrobacterium is a simple technique well known to those skilled in the art. Typically after being wounded, a plant is inoculated with a suspension of tumor-inducing bacteria. Alternatively, tissue pieces are inoculated, e.g. leaf disks (R. B. Horsch et al. (1985) Science 227:1229–1231) or inverted stem segments (K. A. Barton et al. (1983) Cell 32:1033–1043). After induction, the tumors can be placed in tissue culture on media lacking phytohormones usually included for culture of untransformed plant tissue. Traditional inoculation and culture techniques may be modified for use of disarmed T-DNA vectors incapable of inducing hormone independent growth (e.g. see P. Zambryski et al. (1984) in *Genetic Engineering, Principles, and Methods*, 6, eds.: A. Hollaender and J. Setlow).

Agrobacterium is also capable of infecting isolated cells, cells grown in culture, callus cells, and isolated protoplasts (e.g. R. B. Horsch and R. T. Fraley (1983) in *Advances in Gene Technology: Molecular Genetics of Plants and Animals* (Miami Winter Symposium 20), eds.: K. Downey et al., p. 576; R. T. Fraley et al. (1984) Plant Mol. Biol. 3:371–378; R. T. Fraley and R. B. Horsch (1983) in *Genetic Engineering of Plants: an Agricultural Perspective*, eds.: T. Kosuge et al., pp. 177–194; A. Muller et al. (1983) Biochem. Biophys. Res. Comm. 123:458–462). The transformation frequency of inoculated callus pieces can be increased by addition of an opine or opine precursors (L. M. Cello and W. L. Olsen, U.S. Pat. No. 4,459,355).

Plant protoplasts can be transformed by the direct uptake of TIP DNA in the presence of a polycation, polyethelene glycol, or both (e.g. F. A. Krens et al. (1982) Nature 296:72–74), though integrated Ti plasmid may include non-T-DNA sequences.

An alternative method involves uptake of DNA surrounded by membranes. pTi-DNA may be introduced via liposomes or by fusion of plant and bacterial cells after removal of their respective cell walls (e.g. R. Hain et al. (1984) Plant Cell Rept. 3:60–64). Plant protoplasts can take up cell wall delimited Agrobacterium cells. T-DNA can be transmitted to tissue regenerated from fused protoplasts.

The host-range of crown gall pathogenesis may be influenced by T-DNA-encoded functions such as onc genes (A. Hoekema et al. (1984) J. Bacteriol. 158:383–385; A. Hoekema et al. (1984) EMBO J. 3:3043–3047; W. C. Buchholz and M. F. Thomasshow (1984) 160:327–332). R. L. Ausich, European Patent Application 108,580, reports transfer of T-DNA from *A. tumefaciens* to green algal cells, and expression therein of octopine synthase and Tn5 kanamycin resistance genes. G. M. S. Hooykaas-van Slogteren et al. (1984) Nature 311:763–764, and J.-P. Hernalsteens et al. (1984) EMBO J. 3:3039–3041, have demonstrated transformation of monocot cells by Agrobacterium without the customary tumorigenesis.

Regeneration of Plants

Differentiated plant tissues with normal morphology have been obtained from crown gall tumors. For example, L. Otten et al. (1981) Molec Gen. Genet. 183:209–213, used tms (shoot-inducing, root-suppressing) Ti plasmid mutants to create tumors which proliferated shoots that formed self-fertile flowers. The resultant seeds germinated into plants which contained T-DNA and made opines. The tms phenotype can be partly overcome by washing of the rooting area and can be bypassed by grafting onto a normal stock (A. Wostemeyer et al. (1984) Mol. Gen. Genet. 194:500–507). Similar experiments with a tmr (root-inducing, shoot-suppressing) mutant showed that full-length T-DNA could be transmitted through meiosis to progeny and that in those progeny nopaline genes could be expressed, though at variable levels (K. A. Barton et al. (1983) Cell 32:1033–1043).

Genes involved in opine anabolism were capable of passing through meiosis, though the plants were male sterile if the T-DNA was not disarmed. Seemingly unaltered T-DNA and functional foreign genes can be inherited in a dominant, closely linked, Mendelian fashion. Genetically, T-DNA genes are closely linked in regenerated plants (A. Wöstemeyer et al. (1984) Mol. Gen. Genet. 194:500–507; R. B. Horsch et al. (1984) Science. 223:496–498; D. Tepfer (1984) Cell 37:959–967).

The epigenetic state of the plant cells initially transformed can affect regeneration potential (G. M. S. van Slogteren et al. (1983) Plant Mol. Biol. 2:321–333).

Roots resulting from transformation from *A. rhizogenes* have proven relatively easy to regenerate directly into plantlets (M.-D. Chilton et al. (1982) Nature 295:432–434; D. Tepfer (1984) Cell 37:959–967; Tepfer (1983) in Puhler, supra), and are easily cloned. Regenerability from transformed roots may be dependent on T-DNA copy-number (C. David et al. (1984) Biotechnol. 2:73–76). Hairy root regenerants have a rhizogenic potential and isozyme pattern not found in untransformed plants (P. Costantino et al. (1984) J. Mol. Appl. Genet. 2:465–470). The phenotype of these plants is generally altered, although not necessarily deleteriously.

Genes on the TIP Plasmids

The complete sequence of the T-DNA of an octopine-type plasmid found in ATCC 15955, pTi15955, has been reported (R. F. Barker et al. (1983) Plant Molec. Biol. 2:335–350), as has that of the $T_L$ region of pTiAch5 (J. Gielen et al. (1984) EMBO J. 3:835–846). Published T-DNA genes do not contain introns and do have sequences that resemble canonical eukaryotic promoter elements and polyadenylation sites.

Ti plasmids having mutations in the genes tms, tmr, tml, and ocs respectively incite tumorous calli of *Nicotiana tabacum* which generate shoots, proliferate roots, are larger than normal, and do not synthesize octopine; all but ocs are onc (oncogenicity) genes. In other hosts, mutants of these genes can induce different phenotypes (see M. W. Bevan and M.-D. Chilton (1982) Ann. Rev. Genet. 16:357–384). Mutations in T-DNA genes do not seem to affect the insertion of T-DNA into the plant genome (J. Leemans et al. (1982) EMBO J. 1:147–152; L. W. Ream et al. (1983) Proc. Natl. Acad. Sci. USA 80:1660–1664).

Octopine Ti plasmids carry an ocs gene which encodes octopine synthase (lysopine dehydrogenase). All upstream signals necessary for expression of the ocs gene are found within 295 bp of the ocs transcriptional start site (C. Koncz et al. (1983) EMBO J. 2:1597–1603). P. Dhaese et al. (1983) EMBO J. 2:419–426, reported the utilization of various polyadenylation sites by "transcript 7" (ORF3 of Barker et al., supra) and ocs. The presence of the enzyme octopine synthase within a tissue can protect that tissue from the toxic effect of various amino acid analogs (G. A. Dahl and J. Tempe (1983) Theor. Appl. Genet. 66:233–239; M. G. Koziel et al. (1984) J. Mol. Appl. Genet. 2:549–562).

Nopaline Ti plasmids encode the nopaline synthase gene (nos) (sequenced by A. Depicker et al. (1982) J. Mol. Appl. Genet. 1:561–573). The "CAAT" box, but not upstream sequences therefrom, is required for wild-type levels of nos expression; a partial or complete "TATA" box supports very low level nos activity (C. H. Shaw et al. (1984) Nucl. Acids Res. 12:7831–7846). Genes equivalent to tms and tmr have been identified on a nopaline-type plasmid and a number of transcripts have been mapped (L. Willmitzer et al. (1983) Cell 32:1045–1056).

Transcription from hairy root T-DNA has also been detected (L. Willmitzer et al. (1982) Mol. Gen. Genet. 186:16–22). Ri plasmids and tms Ti plasmids can complement each other when inoculated onto plants, resulting in calli capable of hormone-independent growth (G. M. S. van Slogteren (1983) Ph.D. thesis, Rijksuniversiteit te Leiden, Netherlands).

TIP plasmid genes outside of the T-DNA region include the vir genes, which when mutated result in an avirulent Ti plasmid. Several vir genes have been accurately mapped and have been found to be located in regions conserved among various Ti plasmids (V. N. Iyer et al. (1982) Mol. Gen. Genet. 188:418–424). The vir genes function in trans, being capable of causing the transformation of plant cells with T-DNA of a different plasmid type and physically located on another plasmid (e.g. A. J. de Framond et al. (1983) Biotechnol. 1:262–269; A. Hoekema et al. (1983) Nature 303:179–180; J. Hille et al. (1984) J. Bacteriol. 158:754–756; A. Hoekema et al. (1984) J. Bacteriol. 158:383–385); such arrangements are known as binary systems. Chilton et al. (18 Jan. 1983) 15th Miami Winter Symp., described a "micro-Ti" plasmid made by resectioning the "mini-Ti" of de Framond et al., supra (see European Patent application 126,546 for a description). G. A. Dahl et al., U.S. patent application Ser. No. 532,280, and A. Hoekema (1985) Ph.D. Thesis, Rijksuniversiteit te Leiden, The Netherlands, disclose micro-Ti plasmids carrying ocs genes constructed from pTi15955. M. Bevan (1984) Nucl. Acids Res. 12:8711–8721, discloses a kanamycin-resistant micro-Ti. T-DNA need not be on a plasmid to transform a plant cell; chromosomally located T-DNA is functional (A. Hoekema et al. (1984) EMBO J. 3:2485–2490). Ti plasmid-determined characteristics have been reviewed by Merlo, supra (see especially Table II therein), and Ream and Gordon, supra.
TIP Plasmid DNA Ri plasmids have been shown to have extensive homology among themselves (P. Costantino et al. (1981) Plasmid 5:170–182), and to both octopine (F. F. White and E. W. Nester (1980) J. Bacteriol. 144:710–720) and nopaline (G. Risuleo et al. (1982) Plasmid 7:45–51) Ti plasmids, primarily in regions encoding vir genes, replication functions, and opine metabolism functions (L. Jouanin (1984) Plasmid 12:91–102; K. Lahners et al. (1984) Plasmid 11:130–140; E. E. Hood et al. (1984) Biotechnol. 2:702–709; F. Leach (1983) Ph.D. Thesis, Universite de Paris-Sud, Centre d'Orsay, France); none of the homologies are in pRi $T_L$-DNA. pRi T-DNA contains extensive though weak homologies to T-DNA from both types of Ti plasmid (L. Willmitzer et al. (1982) Mol. Gen. Genet. 186:16–22). DNA from several plant species contains sequences, referred to as cT-DNA (cellular T-DNA), having homology with the Ri plasmid (F. F. White et al. (1983) Nature 301:348–350, L. Spano et al. (1982) Plant Molec. Biol. 1:291–300; D. Tepfer (1982) in 2e *Colloque sur les Recherches Fruitieres Bordeaux*, pp. 47–59). G. A. Huffman et al. (1984) J. Bacteriol. 157:269–276 and Jouanin, supra, and Leach, supra, have shown that, in the region of cross-hybridization, the Ri plasmid pRiA4$_b$ is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA (see below). The restriction maps of pRiA4$_b$, pRi1855, and pRiHRI were respectively disclosed by Huffman et al., supra, M. Pomponi et al. (1983) Plasmid 10:119–129, and L. Jouanin supra. Ri plasmids are often characterizable as being agropine-type or mannopine-type (A. Petit et al. (1983) Mol. Gen. Genet. 190:204–214).

A portion of the Ti or Ri plasmid is found in the DNA of tumorous plant cells. T-DNA may be integrated (i.e. inserted) into host DNA at multiple sites in the nucleus. Flanking plant DNA may be either repeated or low copy number sequences. Integrated T-DNA can be found in either direct or inverted tandem arrays and can be separated by spacers. Much non-T-DNA Ti plasmid DNA appears to be transferred into the plant cell prior to T-DNA integration (H. Joos et al. (1983) EMBO J. 2:2151–2160). T-DNA has direct repeats of about 25 base pairs associated with the borders, i.e. with the T-DNA/plant DNA junctions, which may be involved in either transfer from Agrobacterium or integration into the host genome.

Ri plasmids integrate two separate T-DNAs, $T_L$-DNA and $T_R$-DNA, left and right T-DNAs, respectively. $T_L$ (about 15–20 kbp) and $T_R$ (about 8–10 kbp) are separated by about 15–20 kbp (Huffman et al., supra, Jouanin, supra). The region of agropine-type pRi $T_L$ and $T_R$ integrated can vary between individual plants or species inoculated (F. F. White et al. (1983) Nature 301:348–350; D. A. Tepfer (1984) Cell 37:959–967). Though T-DNA is occasionally deleted after integration in the plant genome, it is generally stable. Tumors containing a mixture of cells which differ in T-DNA organization or copy number are the result of multiple transformation events.

The exact location relative to the border repeats of T-DNA/flanking plant DNA junctions varies and need not be within a border repeat. Virulence is not always eliminated after deletion of one of either of the usual nopaline T-DNA border sequences (compare H. Joos et al. (1983) Cell 32:1057–1067 with K. Wang et al. (1984) Cell 38:455–462 and C. H Shaw et al. (1984) Nucl. Acids Res. 12:6031–6041, concerning the right border). The orientation of the right nopaline border can be reversed without total loss of functionality, and a single border sequence is capable of transforming closely-linked sequences (M. De Block et al. (1984) EMBO J. 3:1681–1689). A synthetic 25 bp nopaline right border repeat is functional (Wang et al., supra). Circular intermediates associated with T-DNA transfer appear to be spliced precisely within the 25 bp direct repeats (Z. Koukolikova-Nicola et al. (1985) Nature 313:191–196).
Manipulations of the TIP Plasmids Altered DNA sequences, including deletions, may be inserted into TIP plasmids (see Shuttle Vectors). Some pTi derivatives can be transferred to *E. coli* and mutagenized therein (J. Hille et al. (1983) J. Bacteriol. 154:693–701). P. Zambryski et al. (1983) EMBO J. 2:2143–2150, report use of a vector, deleted for most T-DNA genes to transform tobacco and regenerate morphologically normal plants.

The nopaline synthase promoter can drive expression of drug resistance structural genes useful for selection of transformed plant cells. M. W. Bevan et al. (1983) Nature 304:184–187; R. T. Fraley et al. (1983) Proc. Natl. Acad. Sci. USA 80:4803–4807; and L. Herrera-Estrella et al. (1983) EMBO J. 2:987–995, have inserted the bacterial kanamycin resistance structural gene (neomycin phosphotransferase II, NPT2), or kan, from Tn5 downstream from (i.e. behind or under control of) the nopaline synthase promoter. The constructions were used to transform plant cells which in culture were resistant to kanamycin and its analogs such as neomycin and G418. Promoters for octopine $T_L$ genes ORF24 and ORF25 can also drive kan structural gene expression (J. Velten et al. (1984) EMBO J. 3:2723–2730). Herrera-Estrella et al., supra, reported a similar construction, in which a methotrexate resistance gene (dihydrofolate reductase, DHFR) from Tn7 was placed behind the nos promoter; transformed plant cells were resistant to methotrexate. Furthermore, L. Herrera-Estrella et al. (1983) Nature 303:209–213, have obtained expression in plant cells of enzymatic activity of octopine synthase and chloramphenicol acetyltransferase by placing their structural genes under control of nos promoters. G. Helmer et al. (1984) Biotechnol. 2:520–527, have created a fusion gene useful as a screenable marker having the promoter and 5'-end of the nos structural gene fused to *E. coli* β-galactosidase (lacZ) sequences.

N. Murai et al. (1983) Science 222:476–482, reported fusion of the promoter and the 5'-end of the octopine synthase structural gene to a phaseolin structural gene. The encoded fusion protein was produced under control of the T-DNA promoter. Phaseolin-derived introns underwent proper post-transcriptional processing.

SUMMARY OF THE INVENTION

One object of this invention is to provide means for promoting the expression of structural genes within plant cells wherein said genes are foreign to said cells. In pursuance of this goal, other objects are to provide pRi T-DNA promoters and transcript terminators, and especially pRi $T_L$-DNA-derived promoters and pRi $T_L$-DNA-derived polyadenylation sites, which are DNA sequences capable of controlling structural gene transcription and translation within plant cells, and to provide developmental and phenotypic regulation of said foreign structural genes. Another object is to provide specialized plant tissues and plants having within them proteins encoded by foreign structural genes and, in cases where the protein is an enzyme, having or lacking metabolites or chemicals which respectively are not or are otherwise found in the cells in which the genes is inserted. Other objects and advantages will become evident from the following description.

The invention disclosed herein provides a plant comprising a genetically modified plant cell having a foreign structural gene introduced and expressed therein under control of pRi $T_L$-DNA-derived plant expressible transcription controlling sequences (TxCS). Further, the invention provides plant tissue comprising a plant cell whose genome includes T-DNA comprising a foreign structural gene inserted in such orientation and spacing with respect to pRi $T_L$-DNA-derived plant-expressible TxCS as to be expressible in the plant cell under control of those sequences. Also provided are novel strains of bacteria containing and replicating T-DNA, the T-DNA being modified to contain an inserted foreign structural gene in such orientation and spacing with respect to a T-DNA-derived, plant-expressible TxCS as to be expressible in a plant cell under control of said TxCS. Additionally, the invention provides novel vectors having the ability to replicate in *E. coli* and comprising T-DNA, and further comprising a foreign structural gene inserted within T-DNA contained within the vector, in such manner as to be expressible in a plant cell under control of a pRi $T_L$-DNA TxCS. Furthermore, strains of bacteria harboring said vectors are disclosed.

Much is known about the location, size, and function of many transcripts activated when *A. tumefaciens* T-DNA regions are transferred into the genome of plants (see Background). Most pTi T-DNA $T_L$-DNA open reading frames (ORFs) correlate with known gene products. However, until the disclosure of the present invention, the art knew little about the number, size, and function of genes activated when the $T_L$-DNA regions from *A. rhizogenes* plasmids, such as pRiA4, are transferred into a plant genome. Agropine synthase, tms-1 and tms-2 genes have been identified by homology with pTi T-DNA in Ri plasmids, but these loci are located in pRi $T_R$-DNA (G. A. Huffman et al. (1984) J. Bacteriol. 157:269–276; L. Jouanin (1984) Plasmid 12:91–102). The experimental work presented herein is believed to be the first disclosure of a pRi $T_L$-DNA sequence or of any sequence homologous thereto. The availability of this sequence will enable and otherwise facilitate work in the art of plant transformation to express foreign structual genes and to engage in other manipulations of pRi $T_L$-DNA and pRi $T_L$-DNA-derived sequences. Without the newly disclosed pRi $T_L$-DNA sequence, those of ordinary skill in the art would be unable to use promoters and polyadenylation sites contained therein to promote transcription and translation in plant cells of foreign structural genes. The disclosed sequence reveals the existence of previously unknown T-DNA ORFs and associated transcription controlling sequences, and makes possible construction of recombinant DNA molecules using promoters and polyadenylation sites from pRi $T_L$-DNA genes whose sequences were hitherto unknown and unavailable to the public. The work presented herein is also believed to be the first disclosure of developmental and phenotypic regulation of T-DNA genes. Results newly disclosed herein will allow those of ordinary skill in the art to use T-DNA transcription controlling sequences which are so regulated to express heterologous foreign structural genes in transformed plants. T-DNA genes known to the art before the present disclosure are not known to be so regulated. Furthermore, knowledge of pRi $T_L$-DNA sequence enables one to bring to utility promoters and polyadenylation sites that are presently unrecognized; in the future, should a new pRi $T_L$-DNA transcript be discovered and mapped, the sequence disclosed herein will permit associated TxCSs to be combined with heterologous foreign structural genes.

The present invention comprises foreign structural genes under control of pRi $T_L$-DNA promoters expressible in plant cells, the promoter/gene combination being inserted into a plant cell by any means known to the art. More specifically, in its preferred embodiment the invention disclosed herein comprises expression in plant cells of foreign structural genes under control of certain pRi $T_L$-DNA-derived plant expressible TxCSs, after introduction via T-DNA, that is to say, by inserting the foreign structural gene into T-DNA under control of a pRi $T_L$-DNA promoter and/or ahead of a pRi $T_L$-DNA polyadenylation site and introducing the T-DNA containing the TxCS/structural gene combination into a plant cell using known means. Once plant cells transformed to contain a foreign structural gene expressible under control of a pRi $T_L$-DNA TxCS are obtained, plant tissues and whole plants can be regenerated therefrom using methods and techniques well known in the art. The regenerated plants are then reproduced by conventional means and the introduced genes can be transferred to other strains and cultivars by conventional plant breeding techniques. The invention in principle applies to any introduction of a foreign structural gene combined with a pRi $T_L$-DNA promoter or polyadenylation site into any plant species into which foreign DNA (in the preferred embodiment pTi T-DNA) can be introduced and maintained by any means. In other words, the invention provides a means for expressing a structural gene in a plant cell and is not restricted to any particular means for introducing foreign DNA into a plant cell and maintaining the DNA therein. Such means include, but are not limited to, T-DNA-based vectors (including pTi-based vectors), viral vectors, minichromosomes, non-T-DNA integrating vectors, and the like.

The invention is useful for genetically modifying plant cells, plant tissues, and whole plants by inserting useful structural genes from other species, organisms, or strains that change phenotypes of plants or plant cells when expressed therein. Such useful structural genes include, but are not limited to, genes conveying phenotypes such as improved tolerance to extremes of heat or cold; improved tolerance to drought or osmotic stress; improved resistance or tolerance to insect (e.g. insecticidal toxins), arachnid, nematode, or epiphyte pests and fungal, bacterial, or viral diseases, or the like; the production of enzymes or secondary metabolites not normally found in said tissues or plants; improved nutritional (e.g. storage proteins or lectins), flavor (e.g. sweet proteins), or processing properties when used for fiber or human or animal food; changed morphological traits or developmental patterns (e.g. leaf hairs which protect the plant from insects, aesthetically pleasing coloring or form, changed plant growth habits, dwarf plants, reduced time needed for the plants to reach maturity, expression of a gene in a tissue or at a time that gene is not usually expressed, and the like); male sterility; improved photosynthetic efficiency (including lowered photorespiration); improved nitrogen fixation; improved uptake of nutrients; improved tolerance to herbicides; increased crop yield; improved competition with other plants; and improved germplasm identification by the presence of one or more characteristic nucleic acid sequences, proteins, or gene products, or phenotypes however identified (to distinguish a genetically modified plant of the present invention from plants which are not so modified, to facilitate transfer of a linked artificially introduced phenotype by other (e.g. sexual) means to other genotypes or to facilitate identification of plants protected by patents or by plant variety protection certificates); selectable markers (i.e. genes conveying resistance in cell or tissue culture to selective agents); screenable markers; and the like.

The invention is exemplified by introduction and expression of a structural gene for phaseolin, the major seed storage protein of the bean *Phaseolus vulgaris* L., into plant cells. The introduction and expression of the structural gene for phaseolin, for example, can be used to enhance the protein content and nutritional value of forage or other crops. The invention is also exemplified by the introduction and expression of a lectin structural gene, in this case also obtained from *P. vulgaris*, into plant cells. The introduction and expression of a novel lectin may be used to change the nutritional or symbiotic properties of a plant tissue. The invention is exemplified in yet other embodiments by the introduction and expression of DNA sequences encoding thaumatin, and its precursors prothaumatin, prethaumatin, and preprothaumatin. Mature thaumatin is a heat-labile, sweet-tasting protein found naturally in katemfe (*Thaumatococcus daniellii*) which can be used to enhance the flavor of vegetables which are eaten uncooked without significantly increasing the caloric content of the vegetables. The invention is further exemplified by introduction and expression of a structural gene for a crystal protein from *B. thuringiensis* var. kurstaki HD-73 into plant cells. The introduction and expression of the structural gene for an insecticidal protein can be used to protect a crop from infestation with insect larvae of species which include, but are not limited to, hornworm (*Manduca sp.*), pink boll-worm (*Pectionophora gossypiella*), European corn borer (*Ostrinia nubilalis*), tobacco budworm (*Heliothis virescens*), and cabbage looper (*Trichoplusia ni*). Applications of insecticidal protein prepared from sporulating *B. thuringiensis* do not control insects such as the pink bollworm in the field because of their particular life cycles and feeding habits. A plant containing in its tissues insecticidal protein will control this recalcitrant type of insect, thus providing advantage over prior insecticidal uses of *B. thuringiensis*. By incorporation of the insecticidal protein into the tissues of a plant, the present invention additionally provides advantage over such prior uses by eliminating instances of nonuniform application and the costs of buying and applying insecticidal preparations to a field. Also, the present invention eliminates the need for careful timing of application of such preparations since small larvae are most sensitive to insecticidal protein and the protein is always present, minimizing crop damage that would otherwise result from preapplication larval foraging. Other uses of the invention, exploiting the properties of other structural genes introduced into various plant species, will be readily apparent to those skilled in the art.

BRIEF DESCRIPTION OF THE DRAWINGS

FIGS. 2A–2N. Present nucleotide sequence of $T_L$-DNA region from *A. rhizogenes* agropine-type plasmid pRiHRI. The sequence starts 520 base pairs (bp) to the left of the left $T_L$-DNA/plant junction sequence identified in *C. arvensis* clone 7 and extends 1135 bp to the right of the clone 7 right $T_L$-DNA/plant junction, a total of 21,126 bp.

DETAILED DESCRIPTION OF THE INVENTION

Figure 1:
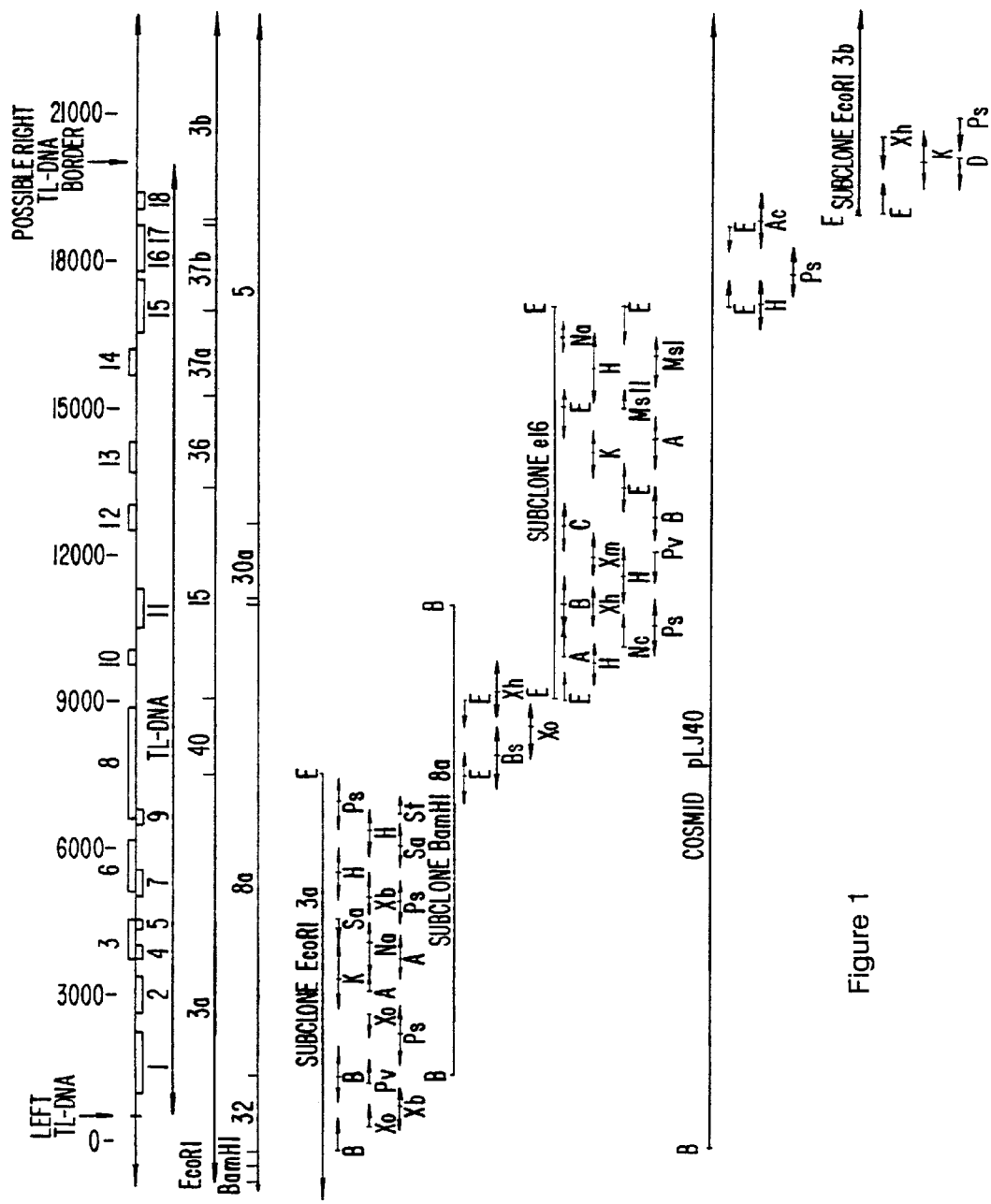
FIG. 1. presents maps of the $T_L$-DNA of agropine Ri plasmid pRiHRI and strategy used for sequencing. The top line represents the $T_L$-DNA region from pRiHRI and the filled boxes indicate locations of ORFs 1 to 18. The left and right $T_L$-DNA borders are those identified from analysis of $T_L$-DNA integrated into *Convolvulus arvensis* clone 7 tissue. ORF polarities are indicated by the position of enclosed boxes on the continuous line; above indicates transcription from left to right and below indicates transcription right to left, i.e. having an mRNA sequence complementary to that disclosed in FIG. 2. EcoRI and BamHI restriction maps are below the ORF map. The complete nucleotide sequence of the $T_L$-DNA was determined from five subclones mapped below the restriction maps: EcoRI 3a, BamHI 8a; Number 16, pLJO ("cosmid 40"); and EcoRI 3b (see Example 2.2). Comparison of restriction enzyme site patterns (L. Jouanin (1984) Plasmid 12:91–102) and overlapping nucleotide sequenced region (Number 16 and cosmid 40) indicate that pRiHRI and pRiA4 $T_L$-DNAs are essentially identical. Cleavage sites and direction of sequence analysis are shown below each subclone, and horizontal arrows indicate direction and distance of sequencing runs. Enzymes are abbreviated as follows: A, AvaI; Ac, AccI; B, BamHI; Bg, BglII; C, ClaI; D, DraI; E, EcoRI; H, HindIII; K, KpnI; MsI, MstI; MsII, MstII; Na, NarI; Nc, NcoI; Ps, PstI; Pv, PvuII; Sa, SalI; St, StuI; Xb, XbaI; Xh, XhoI; Xm, XmnI; and Xo, XorII.

The following terms are defined in order to remove ambiguities to the intent or scope of their usage in the specification and claims.

TxCS: Transcription controlling sequences refers to a promoter/transcript terminator combination flanking a particular structural gene or open reading frame (ORF). The promoter and transcript terminator DNA sequences flanking a particular inserted foreign structural gene need not be derived from the same source genes (e.g. pairing two different pRi $T_L$-DNA) genes or the same taxonomic source (e.g. pairing sequences from pRi $T_L$-DNA with sequences from non-pRi-$T_L$-DNA sources such as other types of T-DNA, plants, animals, fungi, yeasts, and eukaryotic viruses). Therefore the term TxCS refers to either combination of a claimed promoter with an unclaimed transcript terminator, or combination of a unclaimed promoter with a claimed polyadenylation site, or combination of a promoter and a polyadenylation site which are both claimed. Examples of non-pRi-$T_L$-DNA plant-expressible promoters which can be used in conjunction with a pRi $T_L$-DNA polyadenylation site include, but are not limited to, those from genes for nos, ocs, phaseolin, RuBP-Case small subunit and the 19S and 35S transcripts of cauliflower mosaic virus (CaMV).

Promoter: Refers to sequences at the 5'-end of a structural gene involved in initiation of translation or transcription. Expression under control of a pRi T-DNA promoter may take the form of direct expression in which the structural gene normally controlled by the promoter is removed in part or in whole and replaced by the inserted foreign structural gene, a start codon being provided either as a remnant of the pRi T-DNA structural gene or as part of the inserted structural gene, or by fusion protein expression in which part or all of the structural gene is inserted in correct reading frame phase within the existing pRi T-DNA structural gene. In the latter case, the expression product is referred to as a fusion protein. The promoter segment may itself be a composite of segments derived from a plurality of sources, naturally occurring or synthetic. Eukaryotic promoters are commonly recognized by the presence of DNA sequences homologous to the canonical form 5' . . . TATAA . . . 3' about 10–30 bp 5' to the location of the 5'-end of the mRNA (cap site). About 30 bp 5' to the TATAA another promoter sequence is often found which is recognized by the presence of DNA sequences homologous to the canonical form 5' . . . CCAAT . . . 3'. Translational initiation often begins at the first 5' . . . AUG . . . 3'3'-from the cap site (see Example 1.5).

Transcript terminator: Refers to any nucleic acid sequence capable of determining the 3'-end of a eukaryotic messenger RNA (mRNA). The transcript terminator DNA segment may itself be a composite of segments derived from a plurality of sources, naturally occurring or synthetic, and may be from a genomic DNA or an RNA-derived cDNA. Some eukaryotic RNAs, e.g. histone mRNA (P. A. Krieg and D. A. Melton (1984) Nature 308:203–206), ribosomal RNA, and transfer RNA, are not 3'-terminated by polyadenylic acid or by polyadenylation sites; it is intended that the term transcript terminator include, but not be limited to, both nucleic acid sequences determining the 3'-ends of such transcripts and polyadenylation site sequences (see below).

Polyadenylation site: Refers to any nucleic acid sequence capable of determining the 3'-end of a eukaryotic polyadenylated mRNA. After transcriptional termination polyadenylic acid "tails" are added to the 3'-end of most mRNA precursors. The polyadenylation site DNA segment may itself be a composite of segments derived from a plurality of sources, naturally occurring or synthetic, and may be from a genomic DNA or an mRNA-derived cDNA. Polyadenylation sites are commonly recognized by the presence of homology to the canonical form 5' . . . AATAAA . . . 3', although variation of distance, partial "read-thru", and multiple tandem canonical sequences are not uncommon. It should be recognized that a canonical "polyadenylation site" may in fact not actually cause polyadenylation per se (N. Proudfoot (1984) Nature 307:412–413) and that sequences 3' to the "AATAAA" and the 3'-end of the transcript may be needed (A. Gil and N. J. Proudfoot (1984) Nature 312:473–474).

Foreign structural gene: As used herein includes that portion of a gene comprising a DNA segment coding for a foreign RNA, protein, polypeptide or portion thereof, possibly including a translational start codon, but lacking at least one other functional element of a TxCS that regulates initiation or termination of transcription and inititation of translation, commonly referred to as the promoter region and transcript terminator. As used herein, the term foreign structural gene does not include pRi $T_L$-DNA structural genes unless the structural gene and pRi $T_L$-DNA transcription controlling sequences combined with the structural gene are derived from different pRi $T_L$-DNA genes; i.e. unless the structural gene and either a pRi promoter or a pRi polyadenylation site combined with the structural gene are heterologous. (Note that such foreign functional elements may be present after combination of the foreign structural gene with a pRi $T_L$-DNA TxCS, though, in embodiments of the present invention, such elements may not be functional in plant cells). A foreign structural gene may encode a protein not normally found in the plant cell in which the gene is introduced. Additionally, the term refers to copies of a structural gene naturally found within the cell but artificially introduced. A foreign structural gene may be derived in whole or in part from sources including but not limited to eukaryotic DNA, prokaryotic DNA, episomal DNA, plasmid DNA, plastid DNA, genomic DNA, cDNA, viral DNA, viral cDNA, or chemically synthesized DNA. It is further contemplated that a foreign structural gene may contain one or more modifications in either the coding segments or untranslated regions which could affect the biological activity or chemical structure of the expression product, the rate of expression or the manner of expression control. Such modifications include, but are not limited to, mutations, insertions, deletions, and substitutions of one or more nucleotides, and "silent" modifications that do not alter the chemical structure of the expression product but which affect intercellular localization, transport, excretion or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being foreign to the cell into which the gene is introduced and expressed or being derived in part from a foreign protein. The foreign structural gene may be a fusion protein, and in particular, may be fused to all or part of a structural gene derived from the same ORF as was the TxCS.

Plant tissue: Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant cell: As used herein includes plant cells in planta and plant cells and protoplasts in culture.

Production of a genetically modified plant, plant seed, plant tissue, or plant cell expressing a foreign structual gene under control of a pRi T-DNA TxCS, and especially a pRi $T_L$-DNA-derived TxCS, combines the specific teachings of the present disclosure with a variety of techniques and expedients known in the art. In most instances, alternative expedients exist for each stage of the overall process. The choice of expedients depends on variables such as the choice of the basic vector system for the introduction and stable maintenance of the pRi $T_L$-DNA TxCS/structural gene combination, the plant species to be modified and the desired regeneration strategy, and the particular foreign structural gene to be used, all of which present alternative process steps which those of ordinary skill are able to select and use to achieve a desired result. For instance, although the starting point for obtaining pRi $T_L$-DNA TxCSs is exemplified in the present application by pRi $T_L$-DNA isolated from pRiA4 and pRiHRI, DNA sequences of other homologous agropine-type Ri Ti plasmids might be substituted as long as appropriate modifications are made to the TxCS isolation and manipulation procedures. Additionally, T-DNA genes from other types of pRi $T_L$-DNA homologous to the agropine-type pRi $T_L$-DNA genes having TxCSs disclosed herein may be substituted, again with appropriate modifications of procedural details. Homologous genes may be identified by those of ordinary skill in the art by the ability of their nucleic acids to cross-hybridize under conditions of stringency appropriate to detect 70% homology; such conditions are well understood in the art. It will be understood that there may be minor sequence variations within gene sequences utilized or disclosed in the present application. These variations may be determined by standard techniques to enable those of ordinary skill in the art to manipulate and bring into utility the T-DNA promoters and transcript terminators of such homologous genes. (Homologs of foreign structural genes may be identified, isolated, sequenced, and manipulated as is in a similar manner as homologs of the pRi genes of the present invention.) As novel means are developed for the stable insertion of foreign genes in plant cells, those of ordinary skill in the art will be able to select among those alternate process steps to achieve a desired result. The fundamental aspects of the invention are the nature and structure of pRi T-DNA genes and their use as a means for expression of a foreign structural gene in a plant genome. The remaining steps of the preferred embodiment for obtaining a genetically modified plant include inserting the pRi $T_L$-DNA TxCS/structural gene combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

An advantage, which will be readily understood by those skilled in the art, of use of transcription controlling sequences disclosed herein for controlling structural gene expression over previously published T-DNA TxCSs is that transcription of many pRi T-DNA ORFs is phenotypically and developmentally regulated (see Example 1.9). pTi T-DNA genes are not known to be so regulated. Transcripts of ORFs 8, 11, 13, and 15are more prevalent in roots than leaves, with the case of ORF 15being particularly striking, while ORF 12expression is specific to leaves and to a particular phenotype (T', see Example 1.9). Therefore, choice of a particular pRi $T_L$-DNA TxCS allows modulation of expression of a structural gene with which the TxCS is combined. For example, should one want expression of a structural gene to be much higher in roots than leaves; ORF15 provides the TxCS of choice.

A principal feature of the present invention in its preferred embodiment is the construction of T-DNA having an inserted foreign structural gene under control of a pRi $T_L$-DNA TxCS, i.e., between a promoter and a polyadenylation site, as these terms have been defined, supra, at least one of which is derived from pRi $T_L$-DNA. The structural gene must be inserted in correct position and orientation with respect to the desired pRi $T_L$-DNA promoter. Position has two aspects. The first relates to which side of the promoter the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of foreign structural gene insertion must by "downstream" from the promoter. The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted foreign structural gene is similar to the distance between the promoter and the T-DNA gene it normally controls. Orientation refers to the directionality of the structural gene. That portion of a structural gene which ultimately codes for the amino terminus of the foreign protein is termed the 5'-end of the structural gene, while that end which codes for amino acids near the carboxyl end of the protein is termed the 3'-end of the structural gene. Correct orientation of the foreign structural gene is with the 5'-end thereof proximal to the promoter. An additional requirement in the case of constructions leading to fusion protein expression is that the insertion of the foreign structural gene into the pRi $T_L$-DNA promoter-donated structural gene sequence must be such that the coding sequences of the two genes are in the same reading frame phase, a structural requirement which is well understood in the art. An exception to this requirement exists in the case where an intron separates coding sequences derived from a foreign structural gene from the coding sequences of the pRi $T_L$-DNA structural gene. In that case, both structural genes must be provided with compatible splice sites, and the intron splice sites must be so positioned that the correct reading frame for the pRi $T_L$-DNA promoter-donated structural gene and the foreign structural gene are restored in phase after the intron is removed by post-transcriptional processing. Differences in rates of expression or developmental control may be observed when a given foreign structural gene is inserted under control of different pRi $T_L$-DNA TxCSs. Rates of expression may also be greatly influenced by the details of the resultant mRNA's secondary structure, especially stem-loop structures. Stability, ability to be excreted, intercellular localization, intracellular localization, solubility, target specificity, and other functional properties of the expressed protein itself may be observed in the case of fusion proteins depending upon the insertion site, the length and properties of the segment of pRi $T_L$-DNA protein included within the fusion protein and mutual interactions between the components of the fusion protein that effect folded configuration thereof, all of which present numerous opportunities to manipulate and control the functional properties of the foreign protein product, depending upon the desired physiological properties within the plant cell, plant tissue, and whole plant. Similarly to the promoter, the polyadenylation site must be located in correct position and orientation relative to the 3'-end of the coding sequence. Fusion proteins are also possible between the 3'-end of the foreign structural gene protein and a polypeptide encoded by the DNA which serves as a source of the polyadenylation site.

A TxCS is comprised by two major functionalities: a promoter, which is absolutely necessary for gene expression, and a transcript terminator, being In the preferred embodiment a polyadenylation site, positioned respectively 5' and 3' to the structural gene. Although as exemplified herein these two portions of the TxCS are obtained from the same gene, this is not a requirement of the present invention. These 5' and 3' sequences may be obtained from diverse pRi T-DNA genes, especially pRi $T_L$-DNA genes, or one of these sequences may even be obtained from a non-pRi T-DNA gene. For instance, a promoter may be taken from a pRi $T_L$-DNA gene while the polyadenylation site may come from a plant gene.

In the Examples, a foreign structural gene is nested within a pRi $T_L$-DNA TxCS, suturing the structural gene into the TxCS at NdeI sites and placing the entire TxCS/structural gene combination between a pair of BamHI sites. As will be apparent to those of ordinary skill in the art, the TxCS/gene combination may be placed between any restriction sites convenient for removing the combination from the plasmid it is carried on and convenient for insertion into the plant transformation or shuttle vector of choice. Alternatives to the use of paired NdeI sites (5' . . . CATATG . . . 3') at the ATG translational start include, but are not limited to, use of ClaI (5' . . . (not G)ATCGAT(G) . . . 3') or NcoI (5' . . . CCATGG . . . 3') sites. As will be understood by persons skilled in the art, other sites may be used for the promoter/structural gene suture as long as the sequence at the junction remains compatible with translational and transcriptional functions. An alternative to the suture of the promoter to the foreign structural gene at the ATG translational start is suturing at the transcriptional start or cap site. An advantage, especially for eukaryotic structural genes, of the use of this location is the secondary (stem-loop) structure of the foreign structural gene mRNA will not be disrupted thereby leading to an mRNA having translational activity more nearly resembling the activity observed in the organism which was the source of the gene. The restriction sites at the 5'- and 3'-ends of the structural gene need not be compatible. Use of cut sites cut by two different restriction enzymes at the two TxCS/structural gene junctions will automatically correctly orient the structural gene when it is inserted between the TxCS elements, though use of an extra restriction enzyme may necessitate removal of an additional set of inconvenient restriction sites within the TxCS and the structural gene. The use of a single restriction enzyme to link both a promoter and a polyadenylation site to a particular structural gene is not required. Convenient sites within the pRi $T_L$-DNA structural gene and 3' to the translational stop of the foreign structural gene may be used. When these sites have incompatible ends, they may be converted to blunt-ends by methods well known in the art and blunt-end ligated together.

Location of the TxCS/foreign structural gene combination insertion site within T-DNA or a T-DNA-derived vector is not critical as long as the transfer function of the T-DNA borders and any other necessary vector elements (e.g. a selectable or screenable marker) are not disrupted. The T-DNA into which the TxCS/structural gene combination is inserted may be obtained from any of the TIP plasmids, including both Ti and Ri plasmids. The TxCS/structural gene combination is inserted by standard techniques well known to those skilled in the art. The orientation of the inserted plant gene, with respect to the direction of transcription and translation of endogenous T-DNA or vector genes is not critical, either of the two possible orientations is functional. Differences in rates of expression might be observed when a given gene is inserted at different locations within T-DNA.

A convenient means for inserting a TxCS/foreign structural gene combination into T-DNA involves the use of a shuttle vector, as described in the Background. An Agrobacterium strain transformed by a shuttle vector is preferably grown under conditions which permit selection of a double-homologous recombination event which results in replacement of a pre-existing segment of a Ti or Ri plasmid with a segment of T-DNA of the shuttle vector. However, it should be noted that the present invention is not limited to the introduction of the TxCS/structural gene combination into T-DNA by a double homologous recombination mechanism; a homologous recombination event with a shuttle vector (perhaps have only a single continuous region of homology with the T-DNA) at a single site will also prove an effective means for inserting that combination into T-DNA as will insertion of a combination-carrying bacterial transposon.

An alternative to the shuttle vector strategy involves the use of plasmids comprising T-DNA or modified T-DNA, into which an TxCS/foreign structural gene is inserted, said plasmids lacking vir genes and being capable of independent replication in an Agrobacterium strain. As reviewed in the Background, the T-DNA of such plasmids can be transferred from an Agrobacterium strain (e.g. *A. rhizogenes, A. tumefaciens*, or derivatives thereof) to a plant cell provided the Agrobacterium strain contains certain trans-acting vir genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids, which may be derived from Ri or Ti plasmids, differ in the amount of T-DNA contained. A "mini-TIP" plasmid retains all of the T-DNA from a TIP. "Micro-TIP" plasmids are deleted for all T-DNA but that surrounding the T-DNA borders, the remaining portions being the minimum necessary for the sub-TIP plasmid to be transferrable and integratable in the host cell. Sub-TIP plasmids are advantageous in that they are relatively small and relatively easy to manipulate directly, eliminating the need to transfer the gene to T-DNA from a shuttle vector by homologous recombination. After the desired structural gene has been inserted, they can easily be introduced directly into a Agrobacterium cell containing the trans-acting genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill.

pRi T-DNA TxCS/structural gene combinations may be combined with pTi-derived Ti plasmids or sub-TIP vectors.

Modified T-DNA carrying a pRi $T_L$-DNA TxCS/structural gene combination can be transferred to plant cells by any technique known in the art (see Background). The resultant transformed cells must be selected or screened to distinguish them from untransformed cells. Selection is most readily accomplished by providing a selectable marker known to the art incorporated into the T-DNA in addition to the TxCS/foreign structural gene combination. Indeed, a pRi $T_L$-DNA TxCS can be a component of such a marker. In addition, the T-DNA provides endogenous markers such as the gene or genes controlling hormone-independent growth of Ti-induced tumors in culture the gene or genes controlling abnormal morphology of Ri-induced tumor roots, and genes that control resistance to toxic compounds such as amino acid analogs, such resistance being provided by an opine synthase (e.g. ocs). Screening methods well known to those skilled in the art include assays for opine production, specific hybridization to characteristic RNA or T-DNA sequences, or immunological assays. Additionally the phenotype of expressed foreign gene can be used to identify transformed plant tissue (e.g. insecticidal properties of the crystal protein).

Although the preferred embodiment of this invention uses a T-DNA-based Agrobacterium-mediated system for incorporation of the TxCS/foreign structural gene combination into the genome of the plant which is to be transformed, other means for transferring and incorporating the gene are also included within the scope of this invention. Other means for the stable incorporation of the combination into a plant genome additionally include, but are not limited to, use of vectors based upon viral genomes (e.g. see N. Brisson et al. (1984) Nature 310:511–514), minichromosomes, transposons, and homologous or nonhomologous recombination into plant chromosomes. Alternate forms of delivery of these vectors into a plant cell additionally include, but are not limited to, direct uptake of nucleic acid (e.g. see J. Paszkowski et al. (1984) EMBO J. 3:2717–2722), fusion with vector-containing liposomes or bacterial spheroplasts, microinjection, and encapsidation in viral coat protein followed by an infection-like process. After introduction into a plant cell of a pRi $T_L$-DNA TxCS/structural gene combination, the combination will be contained by a plant cell. Furthermore, the combination will be flanked by plant DNA, unless utilizing a nonintegrating vector, e.g. a virus or minichromosome.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. In many plant species, cells transformed by pRi-type T-DNA are readily regenerated, using techniques well known to those of ordinary skill, without undue experimentation. Plant cells transformed by pTi-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. It is important to note that if the mutations in tmr and tms are introduced into T-DNA by double homologous recombination with a shuttle vector, the incorporation of the mutation must be selected in a different manner than the incorporation of the TxCS/structural gene combination; e.g. one might select for tmr and tms inactivation by chloramphenicol resistance while one might select for TxCS/foreign gene integration by kanamycin resistance. The inactivation of the tms and tmr loci may be accomplished by an insertion, deletion, or substitution of one or more nucleotides within the coding regions or promoters of these genes, the mutation being designed to inactivate the promoter or disrupt the structure of the encoded proteins (e.g. the T-DNA of NRRL B-15821, or the pTi of A3004, L. W. Ream et al. (1983) Proc. Natl. Acad. Sci. U.S.A. 80:1660–1664). Resultant transformed cells are able to regenerate plants which carry integrated T-DNA and express T-DNA genes, such as an opine synthase, and also express an inserted pRi $T_L$-DNA TxCS/structural gene combination. These serve as parental plant material for normal progeny plants carrying and expressing the pRi $T_L$-DNA TxCS/heterologous foreign structural gene combination, and for seeds containing the combination, in the preferred embodiments the combination being integrated into a plant chromosome and flanked by plant DNA.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced TxCS/foreign structural gene combination is readily transferred to the desired agronomic cultivar by techniques well known to those skilled in the arts of plant breeding and plant genetics. Sexual crosses of transformed plants with the agronomic cultivars yielded initial hybrid. These hybrids can then be back-crossed with plants of the desired genetic background. Progeny are continuously screened and selected for the continued presence of integrated T-DNA or for the new phenotype resulting from expression of the inserted foreign gene. In this manner, after a number of rounds of back-crossing and selection, plants can be produced having a genotype essentially identical to the agronomically desired parents with the addition of a inserted pRi T-DNA promoter/foreign structural gene combination or of a foreign structural gene/polyadenylation site combination.

EXAMPLES

The following Examples are presented for the purpose of illustrating specific embodiments within the scope of the present invention without limiting the scope; the scope being defined by the claims. Numerous variations will be readily apparent to those of ordinary skill in the art.

These Examples utilize many techniques well known and accessible to those skilled in the arts of molecular biology and manipulation of TIPs and Agrobacterium; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68, R. Wu et al., eds. (1983) Meth. Enzymol. 100 and 101, L. Grossman and K. Moldave, eds. (1980) Meth. Enzymol. 65, J. H. Miller (1972) *Experiments in Molecular Genetics*, R. Davis et al. (1980) *Advanced Bacterial Genetics*, R. F. Schleif and P. C. Wensink (1982) *Practical Methods in Molecular Biology*, and T. Maniatis et al. (1982) *Molecular Cloning*. Additionally, R. F. Lathe et al. (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "sticky" (i.e. having a single-stranded protrusion capable of base-pairing with a complementary single-stranded oligonucleotide) or "blunt" and that the sequence of a sticky-end will be determined by the specificity of the enzyme which produces it.

In the Examples and Tables, the underlining of a particular nucleotide in a primer or other sequence indicates the nucleotide which differs from the naturally found sequence, being an insertion or substitution of one or more nucleotides. The use of lower case for two adjacent nucleotides brackets one or more nucleotides that have been deleted from the native sequence. Unless otherwise noted, all oligonucleotide primers are phosphorylated at their 5'-ends, are represented 5'-to-3', and are synthesized and used as referenced in Example 5.

Plasmids are usually prefaced with a "p", e.g., pRiA4 or p8.8, and strain parenthetically indicate a plasmid harbored within, e.g., *A. rhizogenes* (pRiA4) or *E. coli* HB101 (p8.8). Self-replicating DNA molecules derived from the bacteriophage M13 are prefaced by an "m", e.g. mWB2341, and may be in either single-stranded or double-strand form. *A. tumefaciens* (pTi15955) is on deposit in ATCC 15955, *E. coli* C600 (pRK-203-Kan-103-Lec) as NRRL B-15821, *E. coli* HB101 (pLJ40) as NRRL B-15957, and *E. coli* HB101 (EcoRI e36) as NRRL B-15958 (as deposited EcoRI e36 was designated EcoRI 3a); other deposited strains are listed in column 3 of Table 7.

The DNA constructions described in these Examples have been designed to enable any one of the eukaryotic TxCSs of pRi $T_L$-DNA to be combined with any of four foreign structural genes. Towards that end, the structural genes, the TxCSs, and the TxCS/structural gene combinations have been placed on DNA "cassettes", having the properties that, after initial modifications have been made, any structural gene may be readily inserted into any TxCS without further modification, and any TxCS/structural gene combination may be isolated by a simple procedure applicable to all such combinations. All combinations are thereby equivalent when being inserted into the plant transformation vector of choice. The initial modifications of the TxCSs are all analogous to each other and the initial modifications of the structural genes are also all analogous to each other. These Examples often involve the use of a common strategy for multiple constructions that differ only in items such as choice of restriction enzymes, DNA fragment size, ORFs encoded, plasmids generated or used as starting material, specific numbers and sequences of oligonucleotides used for mutagenesis, sources of plasmids, and enzyme reactions utilized. For the sake of brevity, the DNA manipulations and constructions are generally described once, the differing items being detailed by reference to a particular column in a particular Table, a particular series of manipulations used in a particular construction occupying horizontal lines within that Table. One combination, the ORF 11TxCS with the crystal protein structural gene, is also detailed in the text.

Figure 3:
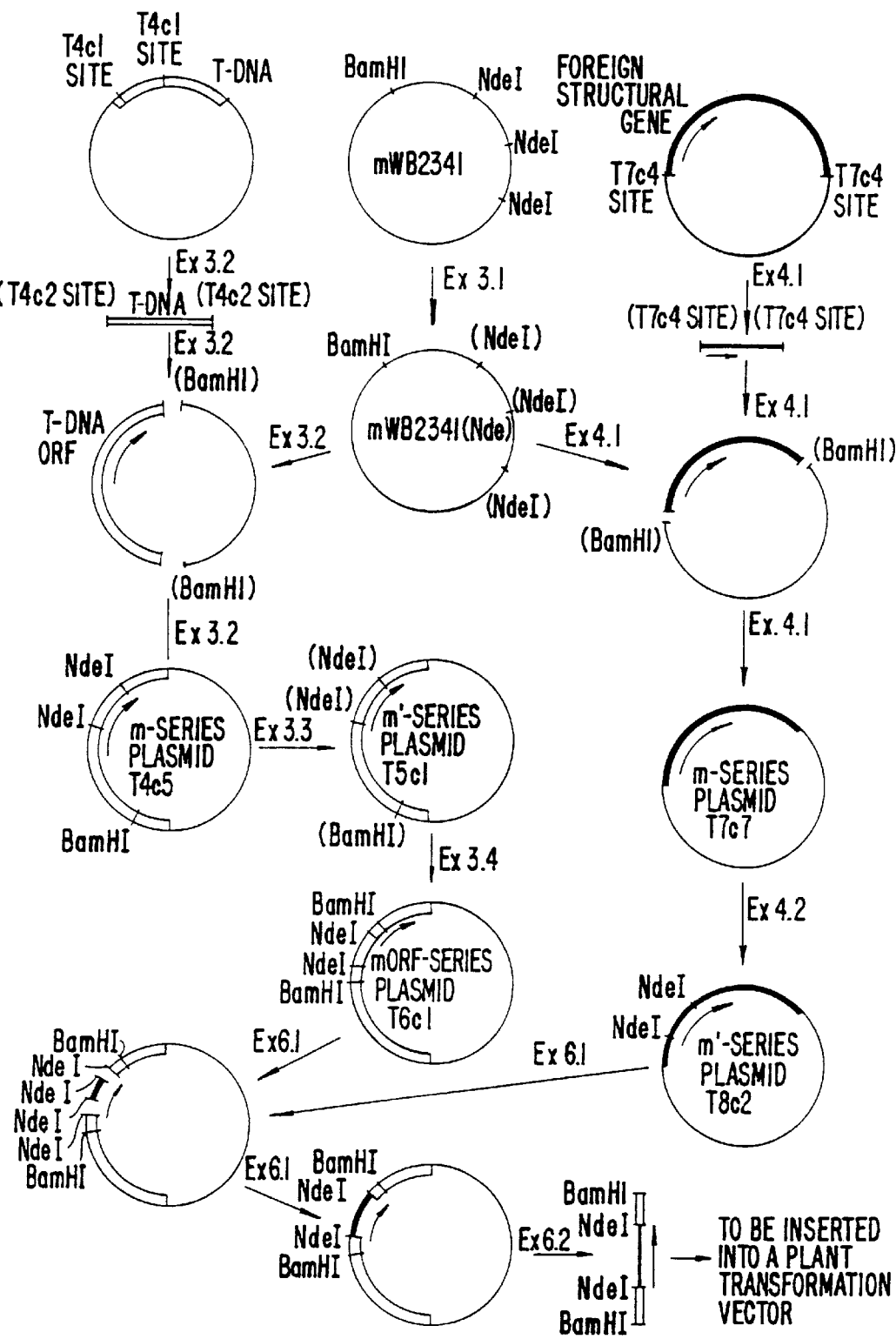
FIG. 3. is a schematic diagram, not drawn to scale, of the DNA manipulation strategy utilized in the Examples. Sites susceptable to the action of a restriction enzyme are indicated by that enzyme's name or place of listing in a Table. For example, "T4c2" refers to an enzyme listed in Table 4, column 2. A site that is no longer susceptable to the enzyme is indicated by the presence of parenthesis around the name of the enzyme. The extent and polarity of an ORF is indicated by an arrow. Names of plasmids, again sometimes designated by place of listing in a Table (e.g. "T5cl" refers to a vector listed in Table 5, column 1), are within the circular representations of the plasmids. Names of vectors, again sometimes designated by a listing in a Table, are within the circular representations of the plasmids. "Ex" refers to the Example which describes a particular manipulation.

The following is an outline, diagrammed schematically in FIG. 3, of a preferred strategy used to make the exemplified DNA constructions detailed in Examples 3 through 6. Endogenous NdeI sites are removed from the M13-based vector mWB2341, resulting in a vector designated mWB2341(Nde) (Example 3.1). Large fragments of T-DNA are introduced into mWB2341(Ne) in a manner that also eliminates the vector's BamHI site (Example 3.2). Endogenous T-DNA NdeI and BamHI sites are then removed (Example 3.3) and novel sites are introduced. NdeI sites are introduced at and near the translational start and stop sites, respectively, so that a foreign structural gene on a NdeI fragment may replace the endogenous ORF structural gene. BamHI sites are introduced approximately 0.3 kbp 5' to and 3' from the transcriptional start and stop signals, respectively, so that the TxCS/structural gene combination eventually constructed may be removed on a BamHI fragment (Example 3.4). The structural genes, which fortuitously have no internal NdeI or BamHI sites, are introduced into mWB2341 (Nde) (Example 4.1) and NdeI sites are introduced at and after the translational start and stop sites (Examples 4.2 and 4.3). The structural genes are removed from their vectors on "DNA cassettes" by digestion with NdeI and are-inserted into any desired TxCS which has had its endogenous structural gene removed by NdeI digestion (Example 6.1). The TxCS/foreign structural gene combinations are then removed from their vector by digestion with BamHI and inserted into the plant transformation vectors of choice (Example 6.2). It is recognized that construction strategies utilizing fortuitously located restriction sites might be designed by persons of ordinary skill which might be simpler for some particular TxCS/structural gene combination than the generalized DNA cassette strategy utilized herein; however, DNA cassettes are a better approach when one is trying to achieve flexibility in the choice and matching of many diverse TxCSs and structural genes.

Example 1

This Example provides disclosure, analysis, and discussion of the pRi $T_L$-DNA sequencing results.

1.1 Summary of results pRi $T_L$-DNA was sequenced and eighteen open reading frames (ORFs), two of which (7 and 18) were clearly prokaryotic in nature, were found. Eleven ORFs had canonical eukaryotic promoter and polyadenylation elements (ORFs 1, 2, 3, 6, 8, 11, 12, 13, 14, 15 and 16). These ORFs were distributed within an about 19.4 kilobase pair (kbp) segment of pRi $T_L$-DNA integrated into the genome of *C. arvensis* clone 7. DNA encoding ORFs 8, 11, 12, 13, and 15 was observed to be transcribed in tobacco.

1.2 Sequence of pRi $T_L$-DNA

A physical map of the pRi $T_L$-DNA region is shown in FIG. 1 along with pRi subclones and the nucleotide sequencing strategy used. Nine-tenths of the sequence obtained was determined from both DNA strands, the remaining tenth being sequenced more than once from the same DNA strand. A nucleotide sequence of 21,126 base pairs (bp) was obtained, which included a 19.4 kbp pRi $T_L$-DNA region identified in the genome of *C. arvensis* clone 7, and is presented in FIG. 2, 5'-to-3' corresponding to left-to-right as mapped in FIG. 1. DNA was sequenced from the 5'-end of BamHI fragment 32 to about 2216 bp into EcoRI fragment 3b (3'-end) (see FIG. 1). The cleavage sites for over seventy restriction enzymes were determined; cleavage positions for enzymes with less than nineteen sites are listed in Table 1.

1.3 $T_L$-DNA border repeats

Genomic hybridization and DNA sequence analyses of the $T_L$-DNA region integrated into the genome of *C. arvensis* clone 7 showed the exact location of a left plant/T-DNA junction and an approximate position for a right pRi $T_L$-DNA/plant junction (F. Leach (1983) Ph.D. Thesis, Universite de Paris-Sud, Centre d'Orsay, France). The left plant DNA/T-DNA junction was between position 570 and 571, as defined in FIG. 2. The left 25 bp T-DNA border repeat sequence was located between positions 520 and 544. The right boundary of $T_L$-DNA of RiA4-transformed *C. arvensis* could vary over a 8 kbp region. The complete 21,126 bp of pRi $T_L$-DNA region was scanned for the presence of a 25 bp consensus sequence derived by comparison with published sequences,

Twenty-seven nucleotide sequences matching this consensus at 15 or more bases were identified. Included among these sequences were the 25 bp nucleotide sequences starting (5') at positions 520 (matching at 23 of 25 bases) and 19,966 (17 of 25) (see FIGS. 2A–2N). These two positions were near the T-DNA/plant junctions of a transformed *Nicotiana glauca* tissue (F. F. White et al. (1983) Nature 301:348–350) and *C. arvensis* clone 7, as determined by comparison of genomic restriction maps of transformed plant DNA and pRiA4 DNA. Other matches were found at positions 154, 576, 725, 3244, 63163 6365, 7209, 7379, 8697, 10339, 10436, 11079, 11232, 12313, 13832, 14235, 14510, 15145, 16285, 17071, 17483, 18121, 18273, 18368, and 18797. The eleven previously published 25 bp border repeat sequences were as little as 64% homologous to each other, thus indicating that many of these pRi border sequences could be functional. Genomic hybridization analysis of the pRi $T_L$-DNA region in tobacco (D. Tepfer (1984) Cell 37:959–967) showed a much smaller $T_L$-DNA with the left junction probably involving a border sequence at either position 6316 or 6365.

1.4 Identification of open reading frames

Analysis of the nucleotide sequence presented in FIG. 2 revealed the presence of sixteen ORFs starting with an ATG initiation codon and extending over 300 nucleotides. The locations, sizes, and molecular weights of the putative translational polypeptides of these ORFs are listed in Table 3. Two additional ORFs (9 and 10) were shorter than 300 nucleotides but were included in Table 3 because they satisfied other criteria (see below). The size of the ORFs ranged from 255 nucleotides (ORF 9) up to 2280 nucleotides (ORF 8), encoding polypeptides ranging in size from 9600 to 85,000 daltons, respectively. However, the actual size of an RNA transcript encoding an ORF could be considerably larger than that listed in Table 3 because 5' and 3' noncoding regions and 3'-polyadenylic acid tails were not included.

Though to date no introns have been found in any of the fourteen sequenced pTi T-DNA genes, (R. F. Barker et al. (1983) Plant Mol. Biol. 2:335–350), J. Gielen et al. (1984) EMBO J. 3:835–846), introns are present in some plant nuclear genes; pRi $T_L$-DNA genes could have introns. Transcript mapping (Example 1.9) did not generally indicate spliced mRNA. However, analysis of mRNA encoded between positions 6500 and 9000 detected two transcripts, a 2300 base transcript as predicted for ORF 8 and an unpredicted 650 base transcript. The nucleotide sequence of the only other ORF in this region, ORF 9, suggested a transcript of about 450 bases, about half the size as found. The coding region of ORF 8 was scanned for sequences which matched consensus donor

the "*" indicating the splice site) and

intron splice sequences and conformed to the G-T/A-G rule (R. Breathnach et al. (1978) Proc. Natl. Acad. Sci. USA 75:4853–4857) and a plant consensus sequence (J. L. Slightom et al. (1983) Proc. Natl. Acad. Sci. USA 80:1897–1901). Splicing between an acceptor at position 8943 and a donor at positions 7283, 7327, 7374, 7701, or 7894 would result in a second transcript having a translation initiation codon-polyadenylation site distance of 724, 758, 943, 1270, or 1325 bp, respectively, which is in the size range observed. Proper processing of an intron-containing genes in T-DNA has been observed (e.g. N. Murai et al. (1983) Science 222:476–482).

No homology greater than random was found to exist in coding or noncoding sequences between pRi $T_L$-DNA and octopine pTi T-DNA (Barker et al., supra), consistent with the lack of cross-hybridization between pRi $T_L$-DNA and octopine pTi T-DNA observed by G. A. Huffman et al. (1984) J. Bacteriol. 157:269–276, and L. Jouanin (1984) Plasmid 12:91–102.

1.5 Translational initiation codons

Eukaryotic translation is preferentially initiated at the first AUG of an mRNA; and A or G at position -3 and G at position +4 may facilitate recognition of functional AUG codons. This

consensus is referred to as the ribosome binding site (M. Kozak (1981) Nucl. Acids Res. 9:5233–5252; M. Kozak (1983) Cell 34:971–978). The number of amino acids and calculated molecular weights for the putative pRi $T_L$-DNA protein products (Table 3) were derived by assigning the first in-phase AUG codon as the initiator codon. The art has not ruled out use of secondary AUG codons as translation initiation codons (M. Kozak (1983) Microbiol. Rev. 47:1–45).

Initiator codon DNA sequences are listed in Table 3 below the consensus eukaryotic ribosome binding site. Eight of the eighteen ORFs had first AUG codons which conform with this consensus sequence (ORFs 1, 7, 8, 10, 11, 12, 14, and 18). Of the ten remaining ORFs, four had downstream, in-phase AUG codons which conformed with the consensus sequence: ORF 2, 287 bp downstream; ORF 3, 160 bp; ORF 6, 344 bp; ORF 13, 203 bp; and ORF 17, 105 bp (see FIG. 2). The remaining six ORFs (2, 4, 5, 9, 15, and 16) did not have any AUG codons which conform to the consensus sequence followed by 300 bp in-phase ORFs. The presence of a consensus ribosome binding AUG codon is not necessary for translation initiation of T-DNA mRNAS; four abundantly transcribed octopine pTi $T_L$-DNA genes are initiated at AUG codons which do not conform to the consensus sequences.

Several pTi T-DNA ORFs are actively transcribed in *E. coli* minicells (G. Schröder et al. (1983) EMBO J. 2:403–409). Translational initiation in *E. coli* and most prokaryotes generally start at an AUG codon that is proceeded by a G-rich ribosome binding site (J. Shine and L. Dalgarno (1974) Proc. Natl. Acad. Sci. USA 71:1342–1346). Sequences which may function as prokaryotic ribosome binding sites were observed ahead of the pRi $T_L$-DNA ORF 4, 5, 7, 9, and 18 initiation codons.

1.6 Codon usage

Most pRi $T_L$-DNA ORFs were observed to fit pTi $T_L$-DNA codon preference patterns, thereby indicating that they are functional after integration into a plant genome, notable exceptions being ORFs 7 and 18.

1.7 Locations of transcription controlling sequences

Comparisons of nucleotide sequences from the 5'-flanking regions of many eukaryotic genes have revealed consensus locations and sequences of several DNA elements which may be important in regulating RNA polymerase II-mediated transcription (S. L. McKnight and R. Kingsbury (1982) Science 217:316–324). These characteristic eukaryotic promoter elements are the "TATA-element", located 25–30 bp upstream (5') from the start of transcription, and the "CCAAT-element", located 40–50 nucleotides upstream from the TATA-element (C. Benoist et al. (1980) Nucl. Acids. Res. 8:127–142; A. Efstratiades et al. (1980) Cell 21:653–668). Similar promoter elements have been found in the 5'-flanking regions of many plant and pTi-T-DNA genes; pTi15955 T-DNA (Barker et al., supra) and pTiAch5 $T_L$-DNA (Gielen et al., supra) have sequences resembling these TATA and CCAAT promoter elements located in the 5'-flanking regions of eight $T_L$-DNA and six $T_R$-DNA ORFs (i.e. have "eukaryotic-looking" promoters). All eight eukaryotic-looking pTi $T_L$-DNA ORFs are transcribed and at least five of six eukaryotic-looking pTi $T_R$-DNA ORFs are known to be transcribed.

The presence of TATA and CCAAT promoter elements in 5'-flanking regions of pRi $T_L$-DNA ORFs indicated that a particular ORF was part of a functional gene. Most pRi $T_L$-DNA ORFs (16 of 18) were flanked by sequences (Table 3) that closely resembled these eukaryotic promoter elements. The amount of sequence identity between the promoter elements and the consensus sequences was very high; ORFs 2 and 12 had promoter elements which matched the consensus sequences while the promoter elements from the other thirteen ORFs did not vary by more than three mismatches. These results were consistent with the degree of homology found for promoter elements from pTi T-DNA ORFs (Barker et al., supra; Gielen et al., supra). pRi $T_L$-DNA open reading frames 1, 4, 8, 10, 13, 14, and 17 were flanked by multiple promoter elements. ORFs 7 and 18 were not flanked by 'sequences resembling eukaryotic promoter elements and were not expected to be transcribed in plant tissues. ORFs 4, 5, 7, and 9 overlapped ORFs 5, 6, and 8 on the opposite strand (FIG. 1, Table 2); the larger ORFs (5, 6, and 8) were more likely to be transcribed because DNA encoding overlapping, antiparallel ORFs in pTi T-DNA was found to be transcribed from either one strand or the other (Gielen et al., supra).

Comparison of polyadenylation sites present in the 3'-noncoding regions of plant genes indicates a preference for the hexanucleotide, AATAAA (J. Messing et al. (1983) in *Genetic Engineering of Plants*, ed.: A. Hollaender, pp. 211–227), however, variations have been observed for plant genes, e.g. AATAAG and GATAAA. Many pTi T-DNA ORFs are also followed by AATAAA sequences. The remaining pTi T-DNA ORFs are followed by polyadenylation sites which vary only slightly, e.g. AATAAT, TATAAA, or AATGAA; AATAAT is known to function for the ocs gene (H. DeGreve et al. (1982) J. Mol. Appl. Genet. 499–511).

Presumptive pRi $T_L$-DNA polyadenylation sites and their locations are listed in Table 3. Ten ORFs (2, 4, 6, 8, 9, 11, 12, 13, 14, and 15) had the consensus hexanucleotide, AATAAA, near their 3'-ends, whereas only two (ORFs 7 and 18) did not contain any related sequence (Table 3, FIGS. 2A–2N). The remaining ORFs (1, 3, 10, and 16) had polyadenylation sites closely related to those described above. ORFs 8, 10, 12, 13, and 14 were followed by multiple polyadenylation signals. Multiple polyadenylation sites have also been observed in several pTi T-DNA genes (P. Dhaese et a . (1983) EMBO J. 2:419–426; Gielen et al., supra).

1.8 ORF locations with respect to base composition

The G+C content of the large Agrobacterium plasmids is about 59% (S. Sheikholeslam et al. (1979) Phytopathol. 69:54–58). In contrast, pRi $T_L$-DNA had very A+T-rich regions flanking the eukaryotic ORFs while coding regions had G+C contents in the range of 50%. Plant genes can also have A+T-rich flanking sequences.

1.9 Detection of transcripts

The $T_L$-DNA left junction with plant DNA found in an *A. rhizogenes* transformed tobacco tissue, clone 9, was between the position 6361 HindIII site and the position 7585 EcoRI site, while the right border was to the right of the position 19,918 KpnI site (see Example 1.3). Hybridization of nick-translated pRi $T_L$-DNA probes to membrane filter-bound replicas of the gels ("Northern blots") clearly showed transcripts carrying ORFs 8 and 13. An observed transcript of about 950 nucleotides which hybridized with pRi $T_L$-DNA between EcoRI sites at positions 9077 and 13,445 was assigned to ORF 11. An observed transcript of about 1400 nucleotides which hybridized with sequences spanning the position 17,059 EcoRI site was assigned to ORF 15. An observed transcript of about 800 nucleotides which hybridized with pRi $T_L$-DNA between the positions 9077 and 13,445 EcoRI sites was assigned to ORF 12.

The relative abundances of pRi $T_L$-DNA transcripts in clone 9-derived plants were observed to be a function of organ (leaves vs. roots) and phenotype (T vs. T'; see Tepfer (1984) supra). With the exception of the transcript corresponding to ORF 12, pRi $T_L$-DNA transcripts were more prevalent in roots than in leaves, with a particularly striking case being the mRNA assigned to ORF 15. Expression of the transcript assigned to ORF 12 was leaf-specific and was correlated with the T' phenotype.

RNA from *C. arvensis* tissue transformed by pRi $T_L$-DNA which included sequences encoding ORFs 1–6 also hybridized with pRi $T_L$-DNA.

1.10 Conclusions

The data discussed above (Examples 1.2, 1.4–1.8) indicated that of the ORFs flanked by eukaryotic transcription controlling sequences (ORFs 1, 2, 3, 4, 5, 6, 8, 9, 10, 11, 12, 13, 14, 15, 16, 17), ORFs 1, 2, 3, 6, 8, 11, 12, 13, 14, 15, and 16 were most likely to be transcribed. In tobacco tissue transformed by DNA encoding ORFs 8–18, transcription of DNA region encoding ORFs 8, 11, 12, 13, and 15 has been detected (Example 1.9).

Example 2

This Example discloses materials and methods used to obtain the results disclosed in Example 1.

2.1 Materials

Restriction endonucleases AvaI, BamHI, BglII, EcoRI, HindIII, KpnI, PstI, PvuII, SalI, StuI, XbaI, and XhoI were obtained from Promega-Biotec. Enzymes AccI, ClaI, DraI, MstI, MstII, NarI, NcoI, XmnI, and XorII were obtained from New England Biolabs. Polynucleotide kinase was from P-L Biochemicals and bovine alkaline phosphatase was from Boehringer-Mannheim. [$\gamma$-$^{32}$P] ATP (2000–3000 Ci/mmole) was obtained from New England Nuclear. Chemicals used for DNA sequencing were obtained from the vendors recommended by A. M. Maxam and W. Gilbert (1980) Meth. Enzymol. 65:499–560. X-ray film on rolls (20 cm×25 m) XAR-351 was obtained from Kodak. DuPont Quanta III intensifying screens (35 cm×1 m) were cut in half to fit sequencing gels (17.5 cm×1 m). DNA sequencing gel stands, designed for gels measuring 20 cm×104 cm, and safety cabinets were from Fotodyne Inc., New Berlin, Wis. Water jacket thermostating plates were constructed using ¼ inch thick plate glass glued together by 100% silicone rubber.

2.2 DNA isolation

Procedures for the isolation and mapping of plasmid and cosmid subclones of the closely-related Ri plasmids pRiA4 and pRiHRI have been published: A4 subclones: EcoRI e36 (EcoRI 3a), BamHI 8a, e16 (contains Ri EcoRI fragments 15, 36, and 37a) by F. Leach (1983) Ph.D. Thesis, Universite de Paris-Sud, Centre d'Orsay; and pRiHRI subclones: pLJ40 (i.e. cosmid 40) and EcoRI 3b by L. Jouanin (1984) Plasmid 12:81–102. Plasmid DNAs were prepared as described by H. C. Birnboim and J. Doly (1979) Nucl. Acids Res. 7:1513–1523, followed by two CsCl, ethidium bromide gradient bandings.

2.3 DNA sequencing

DNA sequences were determined using the chemical method, essentially as described by Maxam and Gilbert, supra. Generally, 10–20 µg of plasmid DNA was digested with the appropriate restriction enzyme, followed by removal of the 5' terminal phosphate with 2–3 units of calf intestinal alkaline phosphatase. Reactions were done in 100 mM Tris pH 8.4, 55° C. for 30 min. Both restriction enzyme and phosphatase were removed by two phenol and one chloroform extractions. DNA samples were then precipitated with ethanol, desalted with 70% ethanol, dried, and then resuspended in 15 µl denaturation buffer (50 mM Tris-HCl (pH 9.5), 5 mM spermidine, and 0.5 mM EDTA) and 15 µl H$_2$O. End-labeling with [γ–$^{32}$P]ATP and isolation of end-labeled fragments were as described by Maxam and Gilbert, supra. Care was taken to avoid sequencing errors resulting from the presence of hydrazine-unreactive 5-methycytosine bases, found after growth in E. coli at the second cytosine base of EcoRII or BstNI restriction enzyme sites (J. L. Slightom et al. (1980) Cell 21:627–638).

Conditions for chemical reactions, at 20° C., were as follows: 1 µl dimethyl sulfate for G, 30 sec.; 30 µl of formic acid 95% for A, 2.5 min.; 30 µl of hydrazine 95% for C+T and C, 2.5 min. DNA samples were electrophoresed 14 hours, at 2500 V at constant voltage on gels 20 cm wide, 104 cm long and 0.2 mm thick. Constant gel temperatures (50° C.) were maintained using a water-jacketed plate on one side of the gel sandwich. The opposite plate of the sandwich was treated with γ-methacryloxypropyltrimethoxy silane (Sigma 6514) as described by H. Garoff and W. Ansorge (1980) Analyt. Biochem. 115:450–457, to bind the acrylamide chemically to the glass. Gel pouring, loading, and autoradiography have been described by R. F. Barker et al. (1983) Plant Mol. Biol. 2:335–350, and J. L. Slightom et al. (1983) Proc. Natl. Acad. Sci. USA 80:1897–1901.

Computer programs for DNA sequence analysis were supplied by the University of Wisconsin Genetics Computer Group.

Example 3

This Example teaches the manipulation of pRi T$_L$-DNA TxCSs preparatory to insertion of a foreign structural gene.

3.1 Removal of NdeI sites from an M13-based vector

These Examples extensively use oligonucleotide-directed, site-specific mutagenesis of DNA (see Example 5.2). Although individuals skilled in the art may choose to use double-stranded DNA methods for such mutagenesis, as exemplified herein single-stranded methods are used. In general, single-stranded methods utilize M13-based vectors having inserted E. coli lac gene sequences. Wild-type M13 contains three NdeI sites while the lac sequences contain no NdeI site; BamHI sites are absent from both M13 and lac. Removal of these NdeI sites, described below, by site-specific mutagenesis may prove essential when replacing a T-DNA structural gene with a heterologous foreign structural gene (Example 6.1). M13-based vectors include mWB2341 and related vectors (W. M. Barnes et al. (1983) Meth. Enzymol. 101:98–122; W. M. Barnes and M. Bevan (1983) Nucl. Acids Res. 11:349–368), and the M13mp-series of vectors (e.g. see J. Norrander et al. (1983) Gene 26:101–106, J. Messing and J. Vieira (1982) Gene 19:269–276). mWB2341 and related vectors are linearized by digestion with EcoRI and HindIII and the resultant sticky-ends are converted to blunt-ends by incubation with the Klenow fragment of E. coli DNA polymerase I. Most of the M13mp-series vectors can be linearized by at least one blunt-end-forming restriction endonuclease (e.g. SmaI or HincII). In the alternative, particular single-stranded DNA vectors may be preferred for some operations; other vectors may be substituted for those referred to above with minor modification of procedures described herein, as will be understood by those of ordinary skill in the art. Also in the alternative, double-stranded DNA vectors might be substituted (see references cited in Example 5.2).

Single-stranded DNA (ssDNA) of the viral form of an M13-based vector is isolated and subjected to oligonucleotide-directed site-specific mutagenesis, described in detail in Examples 3.3 and 5, after hybridization to 5'CAATAGAAAATTCATA<u>G</u>GGTTTACC3', 5'CCT-GTTTAGTATCATA<u>G</u>CGTTATAC3', and 5'CATGTCAAT-CAT<u>TT</u>GTACCCCGGTTG3', thereby removing three NdeI sites which will later prove to be inconvenient without changing the translational properties of the encoded proteins. A mutated M13-based vector lacking three NdeI sites is identified and designated m13(Nde).

3.2 Subcloning pRi T$_L$-DNA into an M13-based vector

DNA of a plasmid listed in Table 4, column 1 (e.g. pLJ40 for manipulations of the ORFs 11, 12, and 13 promoters and polyadenylation sites) (see Example 2.2 for the sources of these plasmids) is isolated and digested to completion with the restriction enzyme(s) listed in Table 4, column 2 (e.g. SmaI and MstII for ORFs 11, 12, and 13). DNAs of e36 and pLJ40 are respectively harbored by the deposited strains NRRL B-15958 and NRRL B-15957. (Alternatively, pRiA4 DNA or pRiHRI DNA may be isolated and digested with the enzyme(s) listed in Table 4, column 2.) 5' or 3'-protruding-ends are then converted to blunt-ends by incubation with the Klenow fragment of E. coli DNA polymerase I or T4 DNA polymerase, respectively, and all four deoxynucleotide triphosphates. The resulting mixture of DNA fragments separated by agarose gel electrophoresis and a fragment whose size is listed in Table 4, column 3 (e.g. 5.2 kbp for ORFs 11, 12, and 13) is eluted from the gel.

Covalently-closed-circular DNA (cccDNA) of the replicative form (RF) of the M13-based vector m13(Nde) is isolated, converted to a linear, blunt-ended DNA, and has its 5'-phosphates removed by incubation with phosphatase. The resulting linearized vector is purified by gel electrophoresis and is mixed with and ligated to the T-DNA fragment isolated above. After transformation of the resulting mixture into E. coli, viral DNAs and RFs are isolated from transformants and screened by restriction and hybridization analysis for the presence of inserts which when in single-stranded viral form, are complementary to the sequence as presented in FIG. 1 and which carry the complete DNA sequence of ORFs listed in Table 4, column 4. The virus which infects the selected colony is designated as listed in Table 4, column 5 (e.g. mR4 for ORFs 11, 12, and 13).

3.3 Removal of endogenous NdeI and BamHI sites from pRi T$_L$-DNA

A vector designated as listed in Table 5, column 1 (e.g. mR4' for manipulations of the ORFs 11, 12, and 13 promoters and polyadenylation sites) is prepared from the vector listed in the corresponding line of Table 5, column 2 (e.g. mR4 for ORFs 11, 12, and 13) by primer extension after hybridization to the oligonucleotides listed in Table 5, column 3 (e.g. 5'GATTAGATAGTCAGATGAGCATGTGC3', 5'GCAAATCGGAGCCCCTCGAATAGG3', 5'GCAATTTGGAGCCATTGTGATGTGAG3', and 5° CGGTTACGCGGAGCCTATGCGGAGCGCC3' for ORFs 11, 12, and 13). This operation removes indigenous BamHI sites and NdeI sites, the sites designated in Table 5, column 4 being at pRi T$_L$-DNA positions listed in column 5 (e.g. for ORFs 11, 12, and 13, an NdeI site at position 10,305 and BamHI sites at positions 11,198, 11,278, and 12,816), which may be present which may prove inconvenient in later manipulations. (Note that there are no BamHI or NdeI sites in mR5.) The sites may be removed one at a time by hybridization of a particular oligonucleotide to the ssDNA viral form of the vector listed in Table 5, column 2 (e.g. mR4 for ORFs 11, 12, and 13), incubation of the primer/viral DNA complex with the Klenow fragment of E. coli DNA polymerase I, all four deoxynucleotide triphosphates, and DNA ligase, enrichment of resulting cccDNA molecules, transformation into E. coli selection of transformants, and isolation of RF followed by restriction enzyme analysis to identify a clone missing the undesired restriction sites. These steps are repeated for each site which is to be removed. Alternatively, the vector listed in Table 5, column 2 (e.g. mR4 for ORFs 11, 12, and 13) may be simultaneously hybridized to all of the oligonucleotides listed in Table 5, column 3 and then carried through the mutagenesis procedure thereby attempting, the procedure not being 100% efficient, to eliminate all of the sites in a single operation.

3.4 Placement of novel NdeI and BamHI sites in pRi T$_L$-DNA

A vector designated as listed in Table 6, column 1 (e.g. mORF 11 for manipulations of the ORF 11 promoter and polyadenylation site) is prepared from the vector listed in the corresponding line of Table 5, column 2 (e.g. mR4' for ORF 11) by primer extention after hybridization to the oligonucleotides listed in Table 6, column 3 (e.g. 5'GCTGCGAAGGGATCCCTTTGTCGCC3', 5'CGCAAGCTACAACATCATATGGGGCGG3', 5'GGGATCCATATGTGATGTGAGTTGG3', 5'GCCTAAGAAGGAATGGTGGATC CATGTACGTGC3' for ORF 11) as described above and in Example 5. This has the effect of introducing NdeI sites (5' . . . CATATG . . . 3') at the translational start site (ATG) and near the translational stop site (TAA, TGA, or TAG), and of introducing BamHI sites (5' . . . GGATCC . . . 3') in the sequences flanking the T-DNA gene, usually approximately 0.3 kbp from the transcriptional start and polyadenylation sites. The first and fourth oligonucleotide of each quartet listed in Table 6, column 3 introduces BamHI sites while the second and thirds introduce NdeI sites. These sites are located in the corresponding pRi T$_L$-DNA at the approximate position listed in Table 6, column 4. For example, for manipulation of ORF 11, (SEQUENCE ID NO. 11) 5'GCTGCGAAGGGATCCCTTTGTCGCC3' and 5'GCCTAA-GAAGGAATGGTGGATCCATGTACGTGC3' introduce BamHI sites and position 9,974 and 12,001, respectively, while 5'CGCAAGCTACAACATCATATGGGGCGG3' and 5'GGGATCCATATGTGATGTGAGTTGG3' introduce NdeI sites at positions 10,679 and 11,286, respectively. The size and locations of the TxCS-carrying DNA segments used in these Examples may be calculated from the positions listed in Table 6, column 4 and the orientations defined in Table 2 and FIG. 1. Positions listed in Table 6, column 4, of pairs of NdeI and BamHI sites define promoter-bearing (P) and polyadenylation site-bearing (A) DNA segments as indicated by "P"s and "A"s, respectively, in column 5, the segments having approximate sizes as indicated in column 6. For example, the ORF 11 promoter is on an approximately 715 bp DNA segment located between artificial NdeI and BamHI sites at approximate positions 11,286 and 12,001, respectively, while the ORF 11 polyadenylation sites is on an approximately 705 bp DNA segment located between artificial BamHI and NdeI sites at approximate positions 9,974 and 10,679, respectively. Note that mORF12-13 and mORF16-17 provide examples of combinations of a promoter and a polyadenylation site from two different T-DNA genes.

Example 4

This Example teaches the manipulation of four exemplary foreign structural genes preparatory for insertion into a pRi T$_L$-DNA TxCS. The genes are for the proteins phaseolin (a nutritionally important seed storage protein from *Phaseolus vulgaris*), *P. vulgaris* lectin (a nutritionally important protein found in seeds and other plant tissues which may be involved in symbiotic nitrogen fixation and making seeds unpalatable to herbivores), thaumatin (a protein which tastes sweet to primates, naturally found in *Thaumatococcus daniellii*), and crystal protein (a protein produced by *Bacillus thuringiensis* which is used commercially to control larval pests of a large number of lepidopteran insect species). The crystal protein structural gene used here, though lacking its 3' end, encodes a protein toxic to insect larvae. Phaseolin, lectin, and thaumatin are eukaryotic genes; crystal protein is prokaryotic. Phaseolin contains introns; lectin and crystal protein do not. The lectin gene itself contains no introns and could be obtained on a 5.7 kbp HindIII fragment from a genomic clone (L. M. Hoffman (1984) J. Mol. Appl. Genet. 2:447–453) which is part of a plasmid harbored by the deposited strain NRRL B-15821 (see also Example 6.4). However, in this Example the lectin structural gene is obtained from a cDNA clone (L. M. Hoffman et al. (1982) Nucl. Acids Res. 10:7819–7828), as is the thaumatin gene.

4.1 Subcloning structural genes into M13

The genes listed in Table 7, column 1 are carried by the plasmids listed in Table 7, column 2, which may be isolated from the deposited stains listed in Table 7, column 3 (e.g. the crystal protein structural gene is carried by p123/58-10 which is harbored within NRRL B-15612). DNA of a plasmid listed in Table 7, column 2 is digested to completion with the restriction enzyme(s) listed in the corresponding row of Table 6, column 4 and protruding ends are removed by incubation with the enzyme listed in Table 6, column 5 (e.g. for manipulation of the crystal protein structural gene, p123/58-10 DNA is digested with HindIII and the resulting sticky-ends are removed by incubation with the Klenow fragment of E. coli DNA polymerase I). A DNA fragment whose size is listed in Table 7, column 6 (e.g. 6.6 kbp for the crystal protein) is isolated by elution from an agarose gel after electrophoretic separation. The resulting fragment is mixed with and ligated to dephosphorylated, blunt-ended, linearized m13(Nde), prepared as described in Example 3.1, and is transformed into *E. coli*. Viral DNAs and RFs are isolated from transformants and screened by restriction and hybridization analyses for the presence of inserts which are complementary to the sequence when in single-stranded viral form as present in the mRNA. The vector which infects the selected colony is designated as listed in Table 7, column 7 (e.g. mBtCP for the crystal protein).

4.2 Placement of NdeI sites flanking three structural genes

DNA of a vector listed in Table 8, column 1 is used to prepare a vector designated as listed in Table 8, column 2 by primer extension after hybridization to the oligonucleotides listed in Table 8, column 3 (e.g. for crystal protein, mBtCP is used to make mBtCP' by extending the primers 5'GGAG-GTAACATATGGATAACAATCCG3' and 5'GCGGCAGAT TAACGTGTTCATATGCATTCGAG3') as described in Examples 3.3 and 5. This has the effect of introducing NdeI sites at the translational start site and near the translational stop site; there are no BamHI or NdeI sites present within the structural gene which might otherwise be removed. In the case of the *B. thuringiensis* crystal protein gene, a translational stop codon (TAA) is additionally introduced. The structural genes listed in Table 7, column 1 may be isolated as a DNA fragment whose size is listed in Table 8, column 4 after digesting DNA of a vector listed in the corresponding line of Table 8, column 2 to completion with NdeI (e.g. the crystal protein structural gene is isolated from mBtCP' on a 2.8 kbp NdeI fragment).

4.3 Mutagenesis of thaumatin

Thaumatin cDNA-containing vectors have been disclosed by C. T. Verrips et al., Eur. Pat. applications 54,330 and 54,331, and L. Edens et al. (1982) Gene 18:1–12. Thaumatin is originally synthesized as preprothaumatin, the prefix "pre" representing the presence of a "signal peptide" having the function of causing the export of thaumatin from the cytoplasm into the endoplasmic reticulum of the cell in which it is being synthesized, and the prefix "pro" representing that the protein is not in mature form. A thaumatin cDNA structural gene is present as the complement to thaumatin mRNA in M13-101-B (Eur. Pat. application 54,331). The viral form of this vector is used as a source of a thaumatin structural gene after site-specific mutagenesis directed by two of the following oligonucleotides: (a) 5'GGCATCATACATCATATGGCCGCCACC3', (b) 5'CCTCACGCTCTCCCGCGCATATGGCCACCTTCGAGATCGTCAACCGC3', (c) 5'CGAGTAAGAGGATGAAGACGGACATATGAGGATACGC3', or (d) 5'GGGTCACTTTCTGCCCTACTGCCTAACATATCAAGACGACTAAGAGG3'. When mutated by oligonucleotides (a) and (c), which bind to the 5'- and 3'-ends of the structural gene, respectively, a preprothaumatin sequence is extracted from the resultant vector by NdeI digestion. When mutated by oligonucleotides (b) and (d), which bind to the 5'- and 3'-ends, respectively, a mature thaumatin sequence is similarly extracted. Use of the combinations of (a) with (d) and (b) with (c) yields fragments encoding what might be termed prethaumatin and prothaumatin, respectively. All of these sequences are obtained on fragments having a size of approximately 0.7 kbp having no internal NdeI or BamHI sites which may be isolated as usual by gel electrophoresis.

4.4 Other possible manipulations

Phaseolin and lectin, as initially translated have signal peptides at their amino-termini, as is the case with thaumatin. If desired, these signal peptides may be eliminated by placing the 5'-NdeI site between the codons forming the junction between the signal peptide and the mature protein. When under control of a T-DNA in a plant cell nucleus, such a structural gene will cause the synthesis of a phaseolin or lectin protein which is not exported from the cell's cytoplasm. Sequences useful for designing oligonucleotides for manipulating for phaseolin and lectin structural genes are respectively reported by J. L. Slightom et al. (1983) Proc. Natl. Acad. Sci. USA 80:1897–1901, and Hoffman et al. (1982) supra.

Example 5

This Example describes techniques for the synthesis and use of synthetic oligonucleotides. Other useful references can be found in the list of works cited in the section introductory to these Examples.

5.1 Oligonucleotide synthesis

Techniques for chemical synthesis of DNA utilize a number of techniques well known to those skilled in the art of DNA synthesis. Modification of nucleosides is described by H. Schaller et al. (1963) J. Amer. Chem. Soc. 85:3821–3827, and H. Buchi and H. G. Khorana (1972) J. Mol. Biol. 72:251–288. Preparation of deoxynucleoside phosphoramidites is described by S. L. Beaucage and M. H. Caruthers (1981) Tetrahedron Lett. 22:1859–1862. Preparation of solid phase resin is described by S. P. Adams et al. (1983) J. Amer. Chem. Soc. 105:561–663. Hybridization procedures useful during the formation of double-stranded molecules are described by J. J. Rossi et al. (1982) J. Biol. Chem. 257:9226–9229.

5.2 Oligonucleotide-directed site-specific mutagenesis

General methods of directed mutagenesis have been reviewed by D. Shortle et al. (1981) Ann. Rev. Genet. 15:265–294. Of special utility in manipulation of genes is oligonucleotide-directed site-specific mutagenesis, reviewed recently by C. S. Craik (1985) Biotechniques 3:12–19; M. J. Zoller and M. Smith (1983) Meth. Enzymol. 100:468–500; M. Smith and S. Gillam (1981) in *Genetic Engineering; Principals and Methods*, Vol. 3, eds.: J. K. Setlow and A. Hollaender; and M. Smith (1982) Trends in Biochem. 7:440–442. This technique permits the change of one or more base pairs in a DNA sequence or the introduction of small insertions or deletions. Recent examples of oligonucleotide-directed mutagenesis include W. Kramer et al. (1984) Nucl. Acids Res. 12:9441–9456; Zoller and Smith (1983) supra; M. J. Zoller and M. Smith (1982) Nucleic Acids Res. 10:6487–6500; G. Dalbadie-McFarland et al. (1982) Proc. Natl. Acad. Sci. USA 79:6409–6413; G. F. M. Simons et al. (1982) Nucleic Acids Res. 10:821–832; and C. A. Hutchison III et al. (1978) J. Biol. Chem. 253:6551–6560. Oligonucleotide-directed mutation using double-stranded DNA vectors is also possible (R. B. Wallace et al. (1980) Science 209:1396–1400; G. P. Vlasuk et al. (1983) J. Biol. Chem. 258:7141–7148; E. D. Lewis et al. (1983) Proc. Natl. Acad. Sci. USA 80:7065–7069; Y. Morinaga et al. (1984) Biotechnol. 2:636–639). See Example 3.1 for useful M13-based vectors.

Example 6

This Example teaches use of the pRi $T_L$-DNA TxCSs and the foreign structural genes manipulated in Example 3 and 4, respectively. Specific Examples of plant transformation vectors, plant transformation, and plant regeneration are given below in Examples 6.4–6.7.

6.1 Assembly of TxCS/structural gene combinations

A plasmid listed in Table 6, column 1 (e.g. mORF 11) is digested with NdeI and dephosphorylated with phosphatase, and the opened vector may be separated from the T-DNA structural gene found nested within the TxCS. A plasmid listed in Table 8, column 2 is digested with NdeI and the corresponding structural gene listed in Table 7, column 1 is isolated as a fragment whose size is listed in Table 8, column 4 by agarose gel electrophoresis followed by elution from the gel (e.g. crystal protein structural gene is isolated from mBtCP' on a 2.8 kbp NdeI fragment). Additionally, a thaumatin-encoding fragment may be isolated as described in Example 4.3. Any desired combination of an opened TxCS vector and an isolated foreign structural gene may now be mixed with each other and ligated together. For example, crystal protein structural gene may be placed between an ORF 11 promoter and an ORF 11 polyadenylation site, thereby replacing the structural gene of ORF 11 with that of the crystal protein, by ligating the 2.8 kbp NdeI fragment of mBtCP' into NdeI-digested mORF 11 DNA. The ligation mixtures are individually transformed into *E. coli* and RFs are isolated from the resultant transformants and characterized by restriction analysis. A colony is chosen for each transformation which lacks the endogenous pRi $T_L$-DNA structural gene and has a single copy of the heterologous foreign structural gene inserted within the TxCS, the structural gene and the TxCS being in such orientation with respect to each other that the gene is expressible under control of the TxCS when within a plant cell.

6.2 Assembly of plant transformation vectors

A TxCS/heterologous foreign structural gene combination may be removed from the M13-based vector constructed in Example 6.1 by digestion with BamHI followed by agarose gel electrophoresis and elution. The size of the BamHI-fragment bearing the promoter/structural gen/polyadenylation site may be calculated by adding the size of the structural gene-bearing fragment, as listed in Table 8, column 4, to the sizes of the promoter and polyadenylation site-bearing segments, as listed in Table 6, column 6. For example, an ORF 11 TxCS/crystal protein structural gene combination, as exemplified herein, may be obtained on a 4.2 kbp BamHI fragment (2.8 kbp+715 bp+705 bp). A TxCS/gene combination may be inserted directly into a 5'GATC . . . 3' sticky-ended site, which may be generated by BamHI, BclI, BglII, MboI, or Sau3AI. Alternatively, the combination may be inserted into any desired restriction site by conversion of sticky-ends into blunt-ends followed by blunt-end ligation or by use of appropriate oligonucleotide linkers.

An alternative to assembly of a pRi $T_L$-DNA TxCS/structural gene combination followed by insertion of that combination into a plant transformation vector is the insertion of a pRi TxCS into a plant transformation vector followed by insertion of the structural gene into the TxCS/transformation vector combination. It is advantageous that the plant transformation vector not contain NdeI sites if the particular manipulation strategy exemplified herein is to be used. Otherwise TxCS/vector combination may be linearized by partial NdeI digestion, as will be understood in the art.

6.3 Vector choice, transformation and plant regeneration

The plant transformation vector into which the TxCS/gene combination is to be inserted may be a TIP-based system such as a TIP plasmid, a shuttle vector for introduction of novel DNAs into TIP plasmids, or a sub-TIP plasmid, e.g. mini-Ti or micro-Ti. Alternatively, a vector based upon a DNA virus, minichromosome, transposon, and homologous or nonhomologous recombination into plant chromosomes may be utilized. Any mode of delivery into the plant cell which is to be initially transformed may be used which is appropriate to the particular plant transformation vector into which the TxCS/structural gene combination is inserted. These forms of delivery include transfer from a Agrobacterium cell, fusion with vector-containing liposomes or bacterial spheroplasts, direct uptake of nucleic acid, encapsidation in viral coat protein followed by an infection-like process, or microinjection.

The initially transformed plant cells are propagated and used to produce plant tissue and whole plants by any means known to the art which is appropriate for the plant transformation vector and delivery mode being used. Methods appropriate for TIP-based transformation systems include those described by M.-D. Chilton et al. (1982) Nature 295:432–434, for carrots, K. A. Barton et al. (1983) Cell 32:1033–1043, for tobacco. Selection of transformed cells may be done with the drugs and selectable markers as described in the Background. The exact drug, concentration, plant tissue, plant species and cultivar must be carefully matched and chosen for ability to regenerate and efficient selection. Screening of transformed tissues for tissues expressing the foreign structural gene may be done using immunoassays known to the art. Southern, northern, and dot blots, all methods well known to those skilled in the art of molecular biology, may be used to detect incorporated or expressed nucleic acids. Screening for opine production is also often useful.

6.4 Preparation of a disarmed T-DNA vector

*E. coli* C600 (pRK-203-Kan-103-Lec), which is on deposit as NRRL B-15821, is a pRK290 derivative containing T-DNA sequences of pTi15955 from between EcoRI sites at positions 4,494 and 12,823, as defined by R. F. Barker et al. (1983) Plant Mol. Biol. 2:335–350, except for a deletion of sequences between position 5,512 HindIII site and position 9,062 BamHI site. Inserted into the deletion, i.e. substituting for the deleted T-DNA, is a Tn5-derived kanamycin resistance (Kan) gene and a *Phaseolus vulgaris* seed lectin gene (see Example 4, Hoffman (1984) supra.). The lectin gene may be deleted from pRK-203-Kan-103-Lec by digestion with HindIII followed by religation; the resultant vector is designated pRK-203-Kan-103. BamHI-digested, dephosphorylated pRK-203-Kan-103 is mixed with and ligated to a BamHI fragment bearing the pRi $T_L$-DNA TxCS/heterologous foreign structural gene combination assembled in Example 6.2; the resultant vector is designated pRK-203-Ri-Kan-103. pRK-203-Ri-Kan-103 is introduced in *A. tumefaciens* ATCC15955 using methods well known in the art, and a double-homologous recombinant, designated RS-Ri-Kan, is identified. RS-Ri-Kan does not harbor pRK-203-Ri-Kan-103, but contains a mutated pTi15955 having a T-DNA substitution between the positions 5,512 HindIII site and 9,062 and BamHI site of a TxCS/structural gene combination and a kan gene for pTi T-DNA. This substitution deletes some tmr and tms sequences, thereby disarming the T-DNA. RS-Ri-Kan T-DNA transforms inoculated plant tissue without conferring the phenotype of hormone-independent growth. Tobacco tissues transformed by RS-Ri-Kan may be regenerated into normal plants using protocols well known in the art for regeneration of untransformed tissue.

6.5 Construction of a micro-Ti plasmid p102, a pBR322 clone of the pTi15955 T-DNA fragment between HindIII sites at positions 602 and 3,390 (as defined by R. F. Barker et al., supra carries the left border of $T_L$ and promoter sequences associated with ORF 1. p233 is a pBR322 clone of the pTi15955 T-DNA BamHI/EcoRI fragment spanning positions 9,062 and 16,202. The T-DNA of p233 includes a SmaI/BclI fragment spanning positions 11,207 and 14,711, having ocs, a 3'-deleted tml, and the right border of $T_L$. p233 was linearized with SmaI, mixed with and ligated to a commercially available blunt-end BglII linker, trimmed with BglII, relegated to itself, and transformed into E. coli GM33 (a dam host that does not methylate DNA in a manner incompatible with the action of BclI, M. G. Marinus and N. R. Morris (1974) J. Mol. Biol. 85:309–322). A colony was identified which harbored a plasmid, designated p233G, having a BglII site in the location formerly occupied by the position 11,207 SmaI site. p233DNA was digested with BglII and BclI and a 3.5 kbp fragment was isolated by agarose gel electrophoresis followed by elution. The 3.5 kbp BglII/BclI fragment was mixed with and ligated to BglII-digested, phosphatase-treated p102 DNA. The ligation mixture was transformed into E. coli K802 (W. B. Wood (1966) J. Mol. Biol. 16:118). Plasmid DNAs from ampicillin-resistant transformants were characterized by restriction analysis and a colony was identified, designated pAK-4, having the BglII/BclI fragment of p233G inserted into the BglII site of p102 and oriented so that the ocs gene was located between the left and right $T_L$ borders. One BglII site, also between the borders, was regenerated, and a BglII/BclI suture, not susceptible to the action of either enzyme, was generate to the right of the right border. pAK-4 may be represented as follows:

... pBR322 ... HindIII ... left border ... BglII ... ocs ... right border ... (BglII/BclI) ... HindIII ... pBR322 ...

The T-DNA of pAK-4 may be removed on a 6 kbp HindIII fragment. HindIII-digested pAK-4 DNA was mixed with and ligated to HindIII-linearized, phosphatase-treated pSUP106 DNA. pSUP106, a 10 kbp wide host-range plasmid capable of maintenance in both E. coli and Agrobacterium (R. Simon et al. (1983) in Molecular Genetics of the Bacteria-Plant Interaction, ed.: A. Pühler, pp. 98–106), is harbored by E. coli CSH52 (pSUP106) which is on deposit as NRRL B-15486. The reaction mixture was transformed into K802 and plasmid DNAs from chloramphenicol-resistant transformants were characterized by restriction analysis. A colony was identified harboring a plasmid, designated pAN6, having the Agrobacterium DNA of pAK-4 inserted into the HindIII site of pSUP106 oriented so that BglII/BclI suture was proximal to the pSUP106 EcoRI site. pAN6 is a micro-Ti plasmid having within its two T-DNA borders a functional ocs gene and a BglII site that is unique to the plasmid. The BglII site is flanked by an incomplete tml gene and the pTi ORF 1 promoter, both of which are transcribed towards the BglII site.

BamHI-digested, dephosphorylated pAN6 is mixed with and ligated to a BamHI fragment bearing the pRi $T_L$-DNA TxCS/heterologous foreign structural gene combination assembled in Example 6.2; the resultant vector is designated pAN6-Ri. pAN6-Ri may be introduced into an Agrobacterium strain having a helper plasmid, e.g. LBA4404 (G. Ooms et al. (1981) Gene 14:33–50), using methods well known in the art.

6.6 Inoculation of tobacco stems

Stems of sterile Nicotiana tabacum var. Xanthi are cut into segments approximately 1 cm long. These segments are placed basal end up in Petri dishes containing Murashige and Skoog medium (MS medium: 1.65 g/l $NH_4NO_3$, 1.9 g/l $KNO_3$, 440 mg/l $CaCl_2 \cdot 2H_2O$, 370 mg/l $MgSO_4 \cdot 7H_2O$, 170 mg/l $KH_2PO_4$, 0.83 mg/l KI, 6.2 mg/l $H_3BO_3$, 22.3 mg/l $MnSO_4 \cdot 4H_2O$, 8.6 mg/l $ZnSO_4 \cdot 7H_2O$, 0.25 mg/l $Na_2MoO_4 \cdot 2H_2O$, 0.025 mg/l $CuSO_4 \cdot 5H_2O$, 0.025 mg/l $CoCl_2 \cdot 6H_2O$, 37.23 mg/l $Na_2EDTA$, 27.85 mg/l $FeSO_4 \cdot 7H_2O$, 1 g/l inositol, 50 mg/l nicotinic acid, 50 mg/l pyroxidine HCl. 50 mg/l thiamine-HCl, 30 g/l sucrose, and 8 g/l agar, pH 5.8) without hormonal supplement, a medium well known in the art. The basal (upper) ends are then inoculated with Agrobacterium cells by puncturing the cut surface of the stem with a syringe needle. After two weeks of incubation at 28° C. with 16 hr light and 8 hr dark, calli develop at the upper surface of all stem segments. The callus regions are then transferred to MS medium containing 2.0 mg/l NAA (1-naphthalene acetic acid), 0.3 mg/l kinetin and 0.5 mg/ml carbinicillin. After two weeks on this medium, the tissues are free of bacteria and can be assayed for the presence of opines, a methodology well known in the art.

Once free of inciting bacteria, the transformed plant tissues are grown on MS medium with hormones at 25° C. with 16 hr light and 8 hr dark. These tissues are cloned using a suspension method described by A. N. Binns and F. Meins (1979) Planta 145:365–369. Briefly, tissues are placed in liquid MS medium supplemented with 2.0 mg/l NAA and 0.1 mg/l kinetin, and shaken at 135 rpm at 28° C. for 10–14 days. The resultant suspensions are filtered successively through 0.543 and 0.213 mm mesh sieves, concentrated, and plated at a final density of $8 \times 10^3$ cells/ml in MS medium supplemented with 2.0 mg/l NAA and 0.3 mg/l kinetin. After these grow to approximately 100 mg, colonies are split into two pieces. One piece is placed on complete MS medium and the other is screened for the presence of opines. Approximately 0–50% of the colonies are found to be opine-positive, depending on the particular parental uncloned callus piece from which the colonies were descended. Uncloned pieces having higher concentrations of opine tended to yield a higher percentage of opine-positive clones.

7 Regeneration of recombinant plants

Tissues from various opine-positive clones are transferred onto MS medium supplemented with 0.3 mg/l kinetin and cultured at 28° C. with 16 hr light and 8 hr dark. Shoots initiated are subsequently rooted by placing them in MS medium without hormones. Rooted plantlets are transferred to soil and placed at high humidity in a greenhouse. After 7–10 days, the plants are then grown with normal greenhouse conditions. Regenerated plants derived from opine-positive clones contain opines. The presence of opines indicates thereby that these normal looking plants are transformed by T-DNA.

TABLE 1

Restriction Enzyme Sites in pRi $T_1$-DNA Region

| Enzyme | No. Sites | Locations | | | |
|---|---|---|---|---|---|
| Bst E II | 1 | 3 993 | | | |
| Sna I | 1 | 6 459 | | | |
| Apa I | 2 | 3 390 | 17 851 | | |
| Mst II | 2 | 4 806 | 15 021 | | |
| Sma I | 2 | 3 075 | 9 863 | | |
| Xba I | 2 | 676 | 4 999 | | |
| Kpn I | 3 | 3 364 | 14 133 | 19 918 | |
| Mlu I | 3 | 17 606 | 20 793 | 20 856 | |
| Nco I | 3 | 2 262 | 10 133 | 21 021 | |
| Sst II | 3 | 3 431 | 14 691 | 17 037 | |
| Xho I | 3 | 9 242 | 11 003 | 20 700 | |
| Bam HI | 4 | 1 343 | 11 198 | 11 278 | 12 816 |
| Hpa I | 4 | 8 375 | 12 459 | 13 700 | 18 818 |
| Nde I | 4 | 3 519 | 3 861 | 4 822 | 10 308 |
| Nru I | 4 | 5 281 | 10 968 | 11 617 | 18 901 |
| Sal I | 4 | 4 515 | 6 047 | 12 655 | 15 821 |

TABLE 1-continued

Restriction Enzyme Sites in pRi T$_L$-DNA Region

| Enzyme | No. Sites | Locations | | | | | |
|---|---|---|---|---|---|---|---|
| Ava III | 5 | 13 684 | 14 382 | 15 480 | 16 415 | 18 262 | |
| BssH II | 5 | 5 727 | 6 847 | 190 761 | 20 260 | 20 660 | |
| BstX I | 5 | 2 269 | 4 226 | 9 912 | 16 016 | 18 309 | |
| Cla I | 5 | 35 | 753 | 11 421 | 12 598 | 21 110 | |
| Nar I | 5 | 465 | 4 114 | 11 356 | 16 441 | 20 385 | |
| Nsi I | 5 | 13 688 | 14 386 | 15 484 | 16 419 | 18 266 | |
| Sca I | 5 | 1 794 | 4 546 | 10 166 | 11 500 | 13 858 | |
| Tth III I | 5 | 3 413 | 3 816 | 8 217 | 8 769 | 11 369 | |
| Xma III | 5 | 5 814 | 7 970 | 8 502 | 10 613 | 20 347 | |
| Aat II | 6 | 974 | 5 615 | 6 054 | 7 521 | 9 272 | 19 089 |
| Asu II | 6 | 4 792 | 10 026 | 12 954 | 16 897 | 19 418 | 19 436 |
| Hind III | 6 | 5 602 | 6 361 | 9 814 | 11 587 | 15 827 | 17 404 |
| Mst I | 6 | 4 004 | 8 091 | 11 427 | 16 088 | 19 690 | 20 408 |
| Pst I | 6 | 2 244 | 4 892 | 7 003 | 10 486 | 10 533 | 17 780 |
| Xor II | 6 | 230 | 2 659 | 4 480 | 5 694 | 8 509 | 16 962 |
| Bcl I | 7 | 992 | 1 364 | 6 710 | 10 564 | 18 673 | 19 403 |
|  |  | 19 827 | | | | | |
| Bgl II | 7 | 4 197 | 5 525 | 7 879 | 11 239 | 13 097 | 15 517 |
|  |  | 15 760 | | | | | |
| EcoR I | 7 | 7 585 | 9 077 | 13 445 | 15 358 | 17 059 | 18 766 |
|  |  | 18 911 | | | | | |
| Acc I | 8 | 333 | 4 515 | 6 048 | 6 460 | 9 514 | 12 656 |
|  |  | 15 822 | 19 089 | | | | |
| Bal I | 8 | 497 | 3 568 | 5 488 | 9 233 | 9 339 | 9 916 |
|  |  | 12 001 | 17 544 | | | | |
| Sph I | 8 | 582 | 11 476 | 15 013 | 15 057 | 15 486 | 17 175 |
|  |  | 19 027 | 20 404 | | | | |
| Xmm I | 8 | 1 759 | 2 725 | 4 498 | 4 546 | 10 103 | 12 206 |
|  |  | 17 338 | 17 917 | | | | |
| EcoR V | 9 | 5 134 | 6 738 | 7 775 | 10 098 | 10 626 | 13 173 |
|  |  | 14 048 | 16 080 | 17 491 | | | |
| Sst I | 9 | 1 967 | 4 152 | 10 879 | 11 068 | 12 395 | 14 105 |
|  |  | 17 016 | 19 214 | 19 866 | | | |
| Stu I | 9 | 5 590 | 6 696 | 7 512 | 11 442 | 12 066 | 15 967 |
|  |  | 16 656 | 20 186 | 20 467 | | | |
| Bgl I | 10 | 1 571 | 3 125 | 5 872 | 5 956 | 6 832 | 9 775 |
|  |  | 10 912 | 14 290 | 16 606 | 21 065 | | |
| Ava I | 11 | 3 073 | 3 765 | 5 268 | 7 012 | 9 242 | 9 861 |
|  |  | 10 573 | 10 629 | 11 003 | 14 402 | 20 700 | |
| Aha III | 12 | 2 486 | 11 334 | 12 233 | 13 427 | 13 530 | 13 666 |
|  |  | 15 577 | 15 599 | 16 168 | 18 135 | 18 573 | 20 070 |
| Nae I | 13 | 316 | 446 | 1 664 | 3 931 | 3 962 | 5 733 |
|  |  | 7 616 | 9 0771 | 15 000 | 16 622 | 18 474 | 20 380 |
|  |  | 20 652 | | | | | |
| Pvu II | 13 | 250 | 1 235 | 1 859 | 2 395 | 2 752 | 7 888 |
|  |  | 8 451 | 12 042 | 13 715 | 15 590 | 15 620 | 16 056 |
|  |  | 18 688 | | | | | |

| | | | | | | |
|---|---|---|---|---|---|---|
| Ban II | 19 | Hph I | 37 | Hpa II | 72 | |
| HgiA I | 19 | Rsa I | 38 | Cfo I | 80 | |
| Ban I | 20 | HinF I | 41 | Hinp I | 80 | |
| Hinc II | 21 | Hga I | 42 | Ala I | 87 | |
| Xho II | 22 | Fok I | 48 | Sau 3a | 87 | |
| Hae II | 23 | Dde I | 55 | Hae III | 99 | |
| Nci I | 23 | Mbo II | 63 | Taq I | 113 | |
| Aha II | 24 | Sau 96 | 66 | Fnu 4A | 132 | |
| Ava II | 26 | Fnu II | 6& | Mnl I | 171 | |
| BstN I | 35 | Bbv I | 69 | | | |

TABLE 2

Open-Reading Frames in pRi T$_L$-DNA

| ORF | Sequence ID NO. | Sequence location After first ATG in-frame | Before terminator | Ribosome binding sites $\begin{array}{c}A\\B\end{array}$ XX ATG G | Coding sequence base pairs | Amino acids | Calculated molecular weight (daltons) of ORF-encoded protein |
|---|---|---|---|---|---|---|---|
| 1. | 1 | 2262 | 937 | GCCATGG | 1326 | 442 | 47,400 |
| 2. | 2 | 3458 | 2649 | GATATGT | 810 | 270 | 29,400 |
| 3. | 3 | 3726 | 4799 | ATCATGC | 1074 | 358 | 38,200 |
| 4. | 4 | 4400 | 4041 | GGGATGC | 360 | 120 | 13,200 |
| 5. | 5 | 4918 | 4607 | GGGATGC | 312 | 104 | 12,000 |
| 6. | 6 | 5143 | 6216 | CGTATGC | 1074 | 358 | 40,300 |
| 7. | 7 | 5643 | 5071 | GGCATGG | 573 | 191 | 21,700 |
| 8. | 8 | 6609 | 8888 | GTGATGG | 2280 | 760 | 85,000 |
| 9. | 9 | 6830 | 6576 | GCCATGA | 255 | 85 | 9,600 |
| 10. | 10 | 9748 | 10044 | AGAATGG | 297 | 99 | 11,400 |
| 11. | 11 | 11282 | 10509 | ACAATGG | 774 | 258 | 29,500 |
| 12. | 12 | 12466 | 13002 | AACATGG | 537 | 179 | 20,100 |
| 13. | 13 | 13723 | 14319 | TGAATGG | 597 | 199 | 22,100 |
| 14. | 14 | 15659 | 16210 | AGCATGG | 552 | 184 | 20,300 |
| 15. | 15 | 17545 | 16517 | CAGATGG | 1029 | 343 | 37,400 |
| 16. | 16 | 18189 | 17737 | AAAATGT | 453 | 151 | 17,400 |
| 17. | 17 | 18743 | 18177 | GAGATGA | 567 | 189 | 21,700 |
| 18. | 18 | 19390 | 19031 | AACATGG | 360 | 120 | 13,400 |

Coordinates represent the A of the AUG initiation codon or the last nucleotide before the termination codon.

TABLE 3

Eukaryotic Transcription Controlling Sequences

| ORF | Sequence ID NO | Sequence and position of promoter elements, positions from first ATG | Sequence and position of polyadenylation sites, positions from terminator | Distance (bp) from first Met to best polyadenylation site |
|---|---|---|---|---|
| | | (CCAAT) | (TATAA) | (AATAAA) | |
| 1. | 1 | −211  −100 | −143  −92  −65 | +38  +100 | 1364 |
| | | CAAT; CAATA | TATA; ATAA; TAATAA | AATAAT; AATATA | |
| 2. | 2 | −81 | −60 | +116 | 926 |
| | | CCAAT | ATAT | AATAAA | 1211 |
| 3. | 3 | −102 | −80 | +137 | |
| | | CAACT | TATA | AATGAA | 740 |
| 4. | 4 | −107 | −82  −46 | +380 | |
| | | CCAAA | ATAAA; AATA | AATAAA | 431 |
| 5. | 5 | −131 | −68 | +119 | |
| | | CCAAAT | ATAA | GATAAA | 1368 |
| 6. | 6 | −146 | −98 | +97  +260  +294 | |
| | | CAAAAT | ATAATA | AATAAT; AGTAAA; AATAAA | |
| 7. | 7 | — | — | — | 573 |
| 8. | 8 | −133  −129 | −92  −72 | +96  +236 | 2376 |
| | | CCTACA; CAAAGT | TAATAA; TATAA | AATAAA; AATAAA | |
| 9. | 9 | −76 | −59 | +187 | 442 |
| | | CAATT | TATAA | AATAAA | |
| 10. | 10 | −221  −91  −64 | −144  −25 | +75  +114 | 414 |
| | | CATAT; CAATA; CAATT | TATATA; TAATA | AATAAG; AATATA | |
| 11. | 11 | −116 | −54 | +350 | 1124 |
| | | CCAAA | TATT | AATAAA | |
| 12. | 12 | −81 | −56 | +83  −141 | 620 |
| | | CCAAT | TATAAA | AATAAA; AATAAA | |
| 13. | 13 | −155 | −87  −51 | +111  +262 | 708 |
| | | CAAAT | ATAAT; TAAATA | AATAAA; AATAAA | |
| 14. | 14 | −174  −116  −95 | −140  −72  −50 | +60  +128  +231 | 612 |
| | | CCAAT; CAAA; CAAAG | AATA; TAAATA; AATA | AATAAA; AATAAA; AATAAA | |
| 15. | 15 | −91 | −65 | +149 | 1178 |
| | | CCAAAA | TATAAA | AATAAA | |
| 16. | 16 | −193 | −126 | +87  +120 | 545 |
| | | CAAAA | TATA | AATTAA: TATAAA | |
| 17. | 17 | −69  −50 | −60  −37 | +92  +164 | 670 |
| | | CAATC; CAAAT | ATAT; ATAAT | TATAAA; AATGAA | |
| 18. | 18 | — | — | — | 360 |

Element positions are negative or positive when respectively 5' or 3' to an ORF.

TABLE 4

Construction of pRi T$_L$-DNA ORF-carrying vectors based on M13

| | 1[a] | 2[b] | 3[b] | 4[b] | 5[c] |
|---|---|---|---|---|---|
| to use ORF 1: | e36 | SmaI | 3.8 kbp | ORF 1 | mR1 |
| to use ORFs 2–9: | pLJ40 or BamH 8a | NcoI | 7.9 kbp | ORFs 2–9 | mR2 |
| to use ORF 10: | pLJ40 or BamH 8a | BglII and BamHI | 3.3 kbp | ORF 10 | mR3 |
| to use ORFs 11–13: | pLJ40 or e16 | SmaI and MstII | 5.2 kbp | ORFs 11–13 | mR4 |
| to use ORFs 14–17: | pLJ40 | KpnI | 5.8 kbp | ORFs 14–17 | mR5 |

[a]Plasmids listed in column 1 are used as sources of pRi T$_L$-DNA sequences.
[b]After restriction enzymes listed in column 2 are used to cut the plasmids listed in column 1, DNA fragments having sizes listed in column 3 are isolated which carry the ORF(s) listed in column 4.
[c]The resultant M13-based vectors designated in column 5 carry the ORFs designated in column 4.

TABLE 5

Removal of endogenous NdeI and BamHI sites from pRi T$_L$-DNA from pRi T$_L$-DNA

| | 1[a] | 2[a] | 3[b] | | 4[b] | 5[b] |
|---|---|---|---|---|---|---|
| to use ORF 1: | mR1' | mR1 | 5' CTGATGACTACAGGAGCCTCGGACAAGC | 3' | BamHI | 1,343 |
| to use ORFs 2–9: | mR2' | mR2 | GCAACGCAACAGATGTAAGGATGAG | | NdeI | 3,518 |
| | | | GGTCTTAGCGGCAGATGTAATGTTGTTGC | | BamHI | 3,860 |
| | | | GGTCGTCAAGGCAGATGTTCTCGGAC | | BamHI | 4,821 |

TABLE 5-continued

Removal of endogenous NdeI and BamHI sites from pRi $T_L$-DNA from pRi $T_L$-DNA

| | 1[a] | 2[a] | 3[b] | | 4[b] | 5[b] |
|---|---|---|---|---|---|---|
| to use ORF 10: | mR3' | mR3 | GATTAGATAGTCAGATGAGCATGTGC | | NdeI | 10,305 |
| to use ORFs 11–13: | mR4' | mR4 | GATTAGATAGTCAGATGAGCATGTGC | | NdeI | 10,305 |
| | | | GCAAATCGGAGCCCCTCGAATAGG | | BamHI | 11,198 |
| | | | GCAATTTGGGAGCCATTGTGATGTGAG | | BamHI | 11,278 |
| | | | CGGTTACGCGGAGCCTATGCGGAGCGCC | | BamHI | 12,816 |

[a]Modified vectors having designations listed in column 1 are made from the vectors listed in column 2.
[b]Oligonucleotides listed in column 3 are used as primers in site-specific mutagensis of vectors listed in column 2, thereby removing restriction sites specific to the enzymes listed in column 4 which are found in the pRi $T_L$-DNA sequence near the positions listed in column 5. Underlined letters in column 3 indicate positions of introduced mutations.

15

TABLE 6

Placement of NdeI and BamHI sites flanking pRi $T_L$-DNA TxCS elements

| | 1[a] | 2[a] | 3[b] | | 4[b] | 5[c] | 6[c] |
|---|---|---|---|---|---|---|---|
| use ORF 1: | mORF1 | mR1' | 5' CTAGAGACCCGTGGATCCGTATAGTCAGCACC 3'<br>GGCTCTGGTGCTCATATGACGTCGAGATGAGG | | 692<br>967 | A | 275 bp |
| | | | CCTATCCTTACCCATATGCAATGGGGTTTTGC<br>GTAAAACAGGAAGGGATCCGGAAAACAGTGC | | 2,265<br>2,611 | P | 346 bp |
| to use ORF 2: | mORF2 | mR2' | GATAGGGTGGGATCCCGTTATTAACTGTTCTCC<br>CGGCCATTACAATACATATGFGCAAGAAG | | 2,324<br>2,579 | A | 255 bp |
| | | | GAGACATATGCAAAGGTGTTTGTGGG<br>GTTGCAGCAATGGATCCCACAAAGGTG | | 3,474<br>3,885 | P | 411 bp |
| to use ORF 3: | mORF3 | mR2' | CCCTTGCAGGGGATCCTGGTCAAATTGG<br>CCTCGCTATCATATGCCCGCCAACGACGCG | | 3,281<br>3,723 | P | 442 bp |
| | | | GGTCGTCAAGGCATATGTTCTCGGAC<br>CCGAGTTGGGATCCCTTTCGGTCTTCG | | 4,821<br>5,106 | A | 285 bp |
| to use ORF 4: | mORF4 | mR2' | CGCAACATATGTAAGGATCCGTTGACTTATTGG<br>GCCACCCCGACATATGCCAGTGCGATG | | 3,531<br>4,025 | A | 494 bp |
| | | | CCGCCACCGATTTTACCCATATGGGCCCTGTCGAGCG<br>CCAAGAAAGATGGCCTTCGGATCCCTGCCTTCTCCCCC | | 4,405<br>4,757 | P | 352 bp |
| to use ORF 5: | mORF5 | mR2' | CAGTGACCGCACCGGATCCGAAAAGTCATTGG<br>CTGTTCCCTTCCATATGAGTGATGC | | 4,277<br>4,689 | A | 412 bp |
| | | | CGTTTCCGTGAACCGCATATGTGAAGAGTTCAATG<br>GGAGGCAACCGGTGGATCCAAAACCTGTGTCTGG | | 4,923<br>5,302 | P | 379 bp |
| to use ORF 6: | mORF6 | mR2' | CAAACGCTCGGATCCCTGTTCCCTTCC<br>CGTGCAACGATATCATATGCGTACAGG | | 4,675<br>5,138 | P | 463 bp |
| | | | CAATCCACTAGCATATGAACAGTAATAAG<br>GCTGCGTGATGGATCCTCCATATCAGC | | 6,221<br>6,613 | A | 392 bp |
| to use ORF 8: | mORF8 | mR2' | CGTTCATCTGGAGAGCGGATCCAGACG<br>CCTGAGTAGCTGCCATATGGATCTTCCATATCAGCG | | 6,156<br>6,604 | P | 448 bp |
| | | | GTTATAGTCATATGTACTATTGCG<br>GAGAAGAGTATTAACTGGATCCACGCAACTCG | | 8,917<br>9,233 | A | 316 bp |
| to use ORF 9: | mORF9 | mR2' | CGTTCATCTGGAGAGCGGATCCAGACG<br>GGATCTTCCATATGAGCGCCCACG | | 6,156<br>6,621 | A | 465 bp |
| | | | GCACCTTGCCTTCATATGGCCCCCGAATAGG<br>CCATGATGAACTGGATCCCAGCAAACTGC | | 6,833<br>7,239 | P | 406 bp |

TABLE 6-continued

Placement of NdeI and BamHI sites flanking pRi T$_L$-DNA TxCS elements

| 1[a] | 2[a] | 3[b] | | 4[b] | 5[c] | 6[c] |
|---|---|---|---|---|---|---|
| to use ORF 10: | mORF10 | mR3' | CTTTATTAATTCTTTGG<u>AT</u>CCCACTGGCCATTAATTG<br>CCTATTTCATGTTTC<u>ATAT</u>GGAATTAGCC | 9,332<br>9,743 | P | 411 bp |
| | | | CGGGATTAATACGC<u>ATAT</u>GGCTGGCGG<br>CAGCAGCAGGATCC<u>AC</u>ACAGAAGAA | 10,054<br>10,349 | A | 295 bp |
| to use ORF 11: | mORF11 | mR4' | GCTGCGAAGGG<u>AT</u>CCCTTTGTCGCC<br>CGCAAGCTACAACATC<u>ATAT</u>GGGGCGG | 9,974<br>10,679 | A | 705 bp |
| | | | GGG<u>AT</u>CCATATGTGATGTGAGTTGG<br>GCCTAAGAAGGAATGGTGG<u>AT</u>CCATGTACGTGC | 11,286<br>12,001 | P | 715 bp |
| to use ORF 12: | mORF12 | mR4' | GCCTAAGAAGGAATGGTGG<u>AT</u>CCATGTACGC<br>CCTACTTTGTTAAC<u>ATAT</u>GGCTGAAGACGACC | 12,001<br>12,463 | P | 462 bp |
| | | | GACATTCGACCTC<u>ATAT</u>GCCAGCACCC<br>CTTCTGAAAAGAAG<u>G</u>ATCCGACATGTTTTC | 12,930<br>13,351 | A | 421 bp |
| to use ORF 13: | mORF13 | mR4' | CTTCTGAAAAGAAGG<u>AT</u>CCGACATGTTTC<br>CCTAAAGTGGCAGCC<u>ATAT</u>GGCTCGTTATTGCAGTGG | 13,351<br>13,718 | P | 367 bp |
| | | | GCTTATGACGCCAT<u>a t</u> GGCAATCGGC<br>CGTTTATTGGGAGG<u>AT</u>CCGCGGGCCG | 14,290<br>14,687 | A | 397 bp |
| to use ORF 14: | mORF14 | mR5 | GCCTTCAAAAATCAGG<u>AT</u>CCACTAGG<br>GCGAAAGTAAGC<u>ATAT</u>GGCAGATGAGTTGG | 15,242<br>15,656 | P | 414 bp |
| | | | GTGATATGTTTTTTAC<u>ATAT</u>GAAGGAG<br>CCAAGCGAGTT<u>G</u>GATCCTACCAAATTCG | 16,170<br>16,491 | A | 321 bp |
| to use ORF 15: | mORF15 | mR5 | CGTTTGAACCCGG<u>AT</u>CCGCGCGGTATTG<br>CGGCAACGTC<u>ATAT</u>GCTTGCTAGCCC | 16,252<br>16,590 | A | 338 bp |
| | | | GTTGTTTGGCC<u>ATAT</u>GCCTTGTAGG<br>CGCAGAGGTAGTCGG<u>AT</u>CCCAAGGCCCGC | 17,549<br>17,888 | P | 339 bp |
| to use ORF 16: | mORF16 | mR5 | GCTTTGACATGG<u>AT</u>CCGGCTTTTCCTGC<br>CCGGTCAGAAAC<u>ATAT</u>GGATGAGTTGTGC | 17,416<br>17,741 | A | 325 bp |
| | | | CTGTGATCTCCTTC<u>ATAT</u>GAAAGACGGGCTTGTTTG<br>CATTGATCTGGCTTCGG<u>AT</u>C<u>C</u>CTGCAATAGGAG | 18,748<br>19,002 | P | 254 bp |
| to use ORF 17: | mORF17 | mR5 | GGTAGTCGG<u>At c</u> CAAGGCCCGCAAC<br>GGTACATTTTTCAC<u>ATAT</u>GCTGTCACCC | 17,887<br>18,201 | A | 314 bp |
| | | | GTCTGTGATCTCCTTC<u>ATAT</u>GAAAGACGGGCTTGTTTG<br>CGGATTAGAATGG<u>AT</u>C<u>C</u>TTTTCACACC | 18,748<br>19,172 | P | 424 bp |
| to use the ORF 12 promoter with the ORF 13 polyadenylation site: | mORF12–13 | mR4' | GCCTAAGAAGGAATGGTGG<u>AT</u>CCATGTACGC<br>CCTACTTTGTTAAC<u>ATAT</u>GGCTGAAGACGACC | 12,001<br>12,463 | P | 462 bp |
| | | | GCTTATGACGCC<u>ATAT</u>GGCAATCGGC<br>CGTTTATTGGGAGG<u>AT</u>CCGCGGGCCG | 14,290<br>14,687 | A | 397 bp |
| to use the ORF 16 promoter with the ORF 17 polyadenylation site: | mORF16–17 | mR5 | GCTTTGACATGG<u>AT</u>CCGGCTTTTCCTGC<br>CCGGTCAGAAAC<u>ATAT</u>GGATGAGTTGTGC | 17,416<br>17,741 | A | 325 bp |
| | | | GTCTGTGATCTCTCCTTC<u>ATAT</u>GAAAGACGGGCTTGTTTG<br>CGGATTAGAATGG<u>AT</u>C<u>C</u>TTTTCACACC | 18,748<br>19,172 | P | 424 bp |

[a]Modified vectors having designations listed in column 1 are made from the vectors listed in column 2.
[b]Oligonucleotides listed in column 3 are used as primers in site-specific mutagenesis of vectors listed in column 2, thereby placing NdeI and BamHI sites flanking each ORF at a position equivalent to the pRi T$_L$-DNA position listed in column 4. The first and fourth oligonucleotide of each quartet introduce BamHI sites, while the second and third introduce NdeI sites. Underlined and lower case letters in column 3 indicate positions of introduced mutations.
[c]Pairs of oligonucleotides marked in column 5 with "P"s define promoter-bearing segments as exemplified herein, while paris marked with "A" define polyadenylation site-bearing segments, the segments having approximate sizes indicated in column 6.

TABLE 7

Construction of vectors carrying structural genes

| 1[a] | 2[a] | 3[a] | 4[b] | 5[b] | 6[c] | 7[c] |
|---|---|---|---|---|---|---|
| to use phaseolin: | p8.8 | NRRL B-15393 | BamHI and BglII | Klenow fragment of E. coli DNA polymerase I | 3.8 kbp | mPhas |
| to use lectin: | pPVL134 | ATCC 39181 | PstI | bacteriophage T4 DNA polymerase | 0.95 kbp | mLec |
| to use crystal protein: | p123/58-10 | NRRL B-15612 | HindIII | Klenow fragment of E. coli DNA polymerase I | 6.6 kbp | mBtCP |

[a]Structural genes encoding the proteins listed in column 1 are carried by plasmids listed in column 2 which are harbored by the deposited strains listed in column 3.
[b]DNAs of plasmids listed in column 2 are digested with the restriction endonuclease(s) listed in column 4 and incubated with the enzymes listed in column 5 to convert sticky-ends to blunt-ends.
[c]DNA fragments of the sizes listed in column 6 are isolated and combined with an M13-based vector described in Example 3.1 to form the vectors listed in column 7.

TABLE 8

Placement of NdeI sites flanking structural genes

| 1[a] | 2[a] | 3[b] | | 4[c] |
|---|---|---|---|---|
| to use phaseolin: | mPhas | mPhas' | 5' CTACTCTAC<u>A</u>TATGATGAGAGCAAGGG 3'<br>GTAGGTGTAAGAGCTC<u>AT</u>ATGGAGAGCATGG | 2.1 kbp |
| to use lectin: | mLec | mLec' | GCATGAATGC<u>A</u>TATGATCATGGCTTCCTCC<br>CCTGCTAATAATGTTCAT<u>A</u>TGTCACAC | 0.8 kbp |
| to use crystal protein: | mBtCP | mBtCP' | GGAGGTAAC<u>A</u>TATGGATAACAATCCG<br>GCGGCAGAT<u>T</u>AACGTGTTCATAT<u>G</u>CATTCGAG | 2.8 kbp |

[a]The vectors listed in column 1 are used to make the modified vectors listed in column 2.
[b]Oligonucleotides listed in column 3 are used as primers in site-specific muta-genesis of vectors listed in colunn 1, thereby placing NdeI sites flanking each structural gene. Underlined letters indicate positions of introduced mutations.
[c]Structural genes carried by vectors listed in column 2 may be isolated on NdeI fragments having sizes listed in column 4.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1326 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..1326)
        ( D ) OTHER INFORMATION: /label=ORF1
            / note= "Sequence ORF1 corresponds to bases 937 through 2262 of Seq. ID No. 19. It is read 5'to 3'from the complementary strand."

( x i ) SEQUENCE DESCRIPTION: SEQ ID NO:1:

| | | | | | |
|---|---|---|---|---|---|
| TGGTTGGCTC | AAATTTTGGC | TCTGGTGCTC | GATGACGTCG | AGATGAGGAC | AGTAGTGATC | 60
| AACTTGGCGG | TCGATACCTT | GGTTACGCCA | CTCCCAGAGT | GCCATGTCGT | CCTCCGAGCG | 120
| GTCTGAGATA | ACCCAGTCGG | CAATTGCTGC | TGCATTGCCG | GGCGTTCCCC | AACCACGACG | 180
| AATATGCTTT | CGTTCATCTA | ACTCGCGTCG | CACTGCCCTC | CCAGTCATGA | AGTCAAAGCC | 240
| AAATTCTACC | CTCTCTCCAT | TTCCCAGCTC | AGTCGAGAAA | TCGTAACACC | TCGTGGCAGC | 300
| TGACAGTTTC | AGAAGGGGC | GTATCCCTCG | AACTCCAGGG | TCCTCTTTCA | CATAGTTAGC | 360
| AAGGCGTACT | GCTGCATAAT | CTGCGTTGAA | GGCTCTGATG | ACTACAGGAT | CCTCGGACAA | 420
| GCCCAATTGA | TCAGGGCGAA | CCCTCGCGCT | CATAATATGA | ATTGCGACGA | CCCTTGCTTC | 480
| CTGTCGGAGC | ATCGAATCAA | TCCAAGCCTT | CCCTGCGGCA | TAGAGGTCAT | CGACTGCGAT | 540
| GTCATCAAGA | TCGAGTAGCT | TTGCCAACCT | AGGAAGTTCT | TGAGGAAAAA | TCACCGGCAT | 600
| GACAGCAACC | GTCTCTCGCC | AGTCAGTTGC | CGGACTGGCT | TCCCTAACGC | CATCCACGAA | 660
| TGCCTCACCG | CTTGCGTATT | TGAATGTGTA | AAAGAGAAGG | ACCACTCTTT | GGCGGTACTT | 720
| CGGACGCCGG | CTTAGCCACG | CGGCAATAAT | GTGGGCCTCA | AACTCACGAC | CATCCAAAAA | 780
| TATAGTCGCG | CCTGGATTGA | CCTCGCTGGC | CTTGTCGAGA | AGAGGTTCCA | AAAAGGGAAC | 840
| GGTGTCTTTC | GTAATAGTAC | TTAAATCTGT | GAGTTCGCCA | TGCGAAACCT | CTCGAACGAT | 900
| TATCGGCGTA | TCCCTGACAT | CAGCTGAATG | AAATTCTCGG | ACGAGTTTGT | CGGGCAAAGT | 960
| GGAGACCCGC | CACGTGTTGA | AGTCGTGGGA | AACGATGGGC | ACATCGTCGC | CGGTGAGTGC | 1020
| GGCATCGAGC | TCAGAGAGGT | TCCGCCTGCC | AACCTCACCG | AGAGCAGCTA | ACAACGAAGT | 1080
| TTCGGTGCAT | TCCTGTATCC | CTTTACCCAG | ATTATACATG | CCCCGGTGTT | CGATAACTTG | 1140
| AAGAGGCAGT | GGCTCCTCAA | GATGTTCAAG | GAGGTGGGGT | ACAGAGTGCC | GGGCGAGGAC | 1200
| CTCATCCACC | GTGACACCAA | CCGGGAGATC | CCATTCGAGT | TTCCACTGGG | GCCAGCATGT | 1260
| GCCCGCGACG | GCGAAAGGTT | TGCGCTGGCA | AAGAACCCGG | CTGCTGCAGG | TGGACCTATC | 1320
| CTTACC | | | | | | 1326

( 2 ) INFORMATION FOR SEQ ID NO:2:

( i ) SEQUENCE CHARACTERISTICS:
        ( A ) LENGTH: 810 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..810)
        ( D ) OTHER INFORMATION: /label=ORF2
            / note= "Sequence ORF2 corresponds to bases 2649
            through 3458 of Seq. ID No. 19. It is read 5'to
            3'from the complementary strand."

( x i ) SEQUENCE DESCRIPTION: SEQ ID NO:2:

| | | | | | |
|---|---|---|---|---|---|
| CTGACTGCGA | TCGGGAAGAA | GCTCGCCAAG | TTCACCGAGA | ATAGCAGAGA | GCGCATCCTC | 60

```
ATCGGGTACT  ACGAACACAT  TCGTCCCAGA  GGGCTTTGTT  TCAGCTGCGC  CAACCCAGAA      120

AGCAAGGCCA  TTTTCCAAGT  TGCCGATGGC  GGTCAGCATG  TTTTGATTGT  TGCTGCCGTT      180

TCCACAAGCG  ATGTGAAGGC  CGATCCCGTG  AGAGAGGCCC  TTGACGAAGG  TGAAATAGCC      240

TTTGGATTTT  CCAACTGTTT  CAACGGGCAC  TAGATATTGA  CCCTCTGGCG  CGGCAACCAC      300

CTTGAATTTG  CGAGATGACT  GGTTGCCGAT  GAGCGAAGAA  AGCATTTCTC  CGGCTTCTTT      360

GTAAGATTTG  TGAGATTCCC  ACATTTGACA  GCCGTAGAAA  TGCCCCATCG  GAATGTTGCG      420

GATTCCCGGG  ATGCCACCAA  ATTTGTTCTC  CATAGCCGCG  TGAACGGCTT  GCCAGTTGGG      480

CAGGGAGAAA  GAATCGAAGC  GATCATCTTT  GTAGATCGTG  ACCATTCCAT  CATTTCCCTG      540

GAATCCGATA  TTTTCAATGG  CGCTGAAAAC  TGACCTTGCG  ATTTCTTCGC  ATTCCCGTGC      600

GGATGTGAGC  AATTGATAAT  GGCCCTTGCA  GGCGATCCTG  GTCAAATTGG  CGATGATGTT      660

GATGGCAGGA  TTAATATCCC  AACACTGGTG  ATTTCGATCT  TGCTTAAAGG  TGGTACCATC      720

GCCGTCGAAG  GCGAGCAGGG  CCCGGAGAGA  TGAATCGGCA  AGACTGCGTC  GGACCCGCTC      780

CGCGGCGTCG  GGAATGAGGC  TGATAAGAGA                                          810
```

( 2 ) INFORMATION FOR SEQ ID NO:3:

( i ) SEQUENCE CHARACTERISTICS:
        ( A ) LENGTH: 1074 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: 1..1074
        ( D ) OTHER INFORMATION: /label=ORF3
            / note= "Sequence ORF3 corresponds to bases 3726
            through 4799 of Sequence ID No. 19."

( x i ) SEQUENCE DESCRIPTION: SEQ ID NO:3:

```
CCCGCCAACG  ACGCGACATG  CGCTGCCGCG  ATTGCCTTCC  CCGAGGGCAA  CTGGAAGGAA       60

GAACTTGATG  CGCTCCGCAC  CTTGTGTGAC  CCCGTCGAGG  TGGTTAAGGT  CGCAGTCGGC      120

AGAGGTCTTA  GCGGCATATG  TAATGTTGTT  GCAGCAATGA  ATCCACAAA   GGTGAGGGGC      180

CTCGGCGATG  TCATCGGGCA  GATGCCGGCT  CTTAATCACC  GTATTGCTGC  CGCCGCCGGC      240

GAAACTCCGG  TGCGAGACCT  TGGAATAGGT  TACCAGTGCG  CAATCTGCCA  CCCCGACATA      300

GCCAGTGCGA  TGTTAGCCAC  TTCTGAGGGG  ATCAGCCACG  TTCTCCGTGA  AAGGATTGAG      360

AAAGAAGTTG  ACCGGGACAT  TGGAGAAGGC  GCCACCGTCT  GCATTTTCGT  TCAGCCGAGA      420

ATGAGCTCCA  AGGGCTCTCC  AGTTTCTGTC  CATTTCACCC  TCCAGTTTGC  GAGATCTGGA      480

ACTCTTGTCG  ATGCCAGAAT  GATGGAGAGT  TACAATTTCA  TGAAAGGCAA  TGGCACAGTG      540

ACCGCACCGG  ATTTGAAAAG  TCATTGGAAG  AAGCACGGTA  TTGACAGGCC  AGGCCCACGT      600

CCGCCCACGT  CCAAGTTTGA  ACTCCTCTTC  GCCGCTGTCC  CCGACAACAG  TAAACTTGCC      660

GCCACCGATT  TTACCCATCT  CGGCCCTGTC  GAGCGTGATA  AGGAACTACT  CGGCAGCACG      720

GTATTCGGGA  TTGCCGCTAA  GAAACCTGGT  ACGATCGTTT  ATCCGTGCGA  AAAGGTTCTC      780
```

| | | | | | | |
|---|---|---|---|---|---|---|
| TGTTTGGAGG | TCGACGTACA | CGCGCATCGC | GCCCTAGAAG | TACTTCACCG | CCTTGGGGAA | 840 |
| CAGGCTTATA | GCAATGGCCG | TGGCACTAGC | TTCGGTCTTC | ACACCGGTCC | GTCCTCTTGC | 900 |
| CTTAATCTTT | CCGCCGCCGC | GCTCGCTACA | TTTTCAAAC | GCTCGGATCT | CTGTTCCCTT | 960 |
| CCATTGAGTG | ATGCTTTTGT | CCTTTCTGC | GACCCGCCAC | CGCCTACAGC | GCCAAGAAAG | 1020 |
| ATGGCCTTCC | GATCACTGCC | TTCTCCCCCA | CGAGCACCAA | TCAGTTCGAA | CTCG | 1074 |

( 2 ) INFORMATION FOR SEQ ID NO:4:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: DNA (genomic)

( v ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..360)
        ( D ) OTHER INFORMATION: /label=ORF4
            / note= "Sequence ORF4 corresponds to bases 4041
            through 4400 of Seq. ID No. 19. It is read 5'to
            3'from the complementary strand."

( x i ) SEQUENCE DESCRIPTION: SEQ ID NO:4:

| | | | | | | |
|---|---|---|---|---|---|---|
| GCCACTTCTG | AGGGGATCAG | CCACGTTCTC | CGTGAAAGGA | TTGAGAAAGA | AGTTGACCGG | 60 |
| GACATTGGAG | AAGGCGCCAC | CGTCTGCATT | TTCGTTCAGC | CGAGAATGAG | CTCCAAGGGC | 120 |
| TCTCCAGTTT | CTGTCCATTT | CACCCTCCAG | TTTGCGAGAT | CTGGAACTCT | TGTCGATGCC | 180 |
| AGAATGATGG | AGAGTTACAA | TTTCATGAAA | GGCAATGGCA | CAGTGACCGC | ACCGGATTTG | 240 |
| AAAAGTCATT | GGAAGAAGCA | CGGTATTGAC | AGGCCAGGCC | CACGTCCGCC | CACGTCCAAG | 300 |
| TTTGAACTCC | TCTTCGCCGC | TGTCCCCGAC | AACAGTAAAC | TTGCCGCCAC | CGATTTTACC | 360 |

( 2 ) INFORMATION FOR SEQ ID NO:5:

( i ) SEQUENCE CHARACTERISTICS:
        ( A ) LENGTH: 312 base pairs
        ( B ) TYPE: nucleic acid
        ( C ) STRANDEDNESS: double
        ( D ) TOPOLOGY: linear ( i i ) MOLECULE TYPE: DNA (genomic)

( v ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..312)
        ( D ) OTHER INFORMATION: /label=ORF5
            / note= "Sequence ORF5 corresponds to bases 4607
            through 4918 of Seq. ID No. 19. It is read 5'to
            3'from the complementary strand."

( x i ) SEQUENCE DESCRIPTION: SEQ ID NO:5:

```
CACCGGTCCG  TCCTCTTGCC  TTAATCTTTC  CGCCGCCGCG  CTCGCTACAT  TTTTCAAACG    60

CTCGGATCTC  TGTTCCCTTC  CATTGAGTGA  TGCTTTTGTC  CTTTTCTGCG  ACCCGCCACC   120

GCCTACAGCG  CCAAGAAAGA  TGGCCTTCCG  ATCACTGCCT  TCTCCCCCAC  GAGCACCAAT   180

CAGTTCGAAC  TCGTAGAGCC  TCAGGTCGTC  AAGGCATATG  TTCTCGGACT  TTTCGACGCG   240

CCGACGATGG  TTACGCCCCG  CGACAAAACG  CGAGCCAGCT  TCTGCAGCCA  ATATGTACGT   300

TTCCGTGAAC  CG                                                          312
```

(2) INFORMATION FOR SEQ ID NO:6:

(i) SEQUENCE CHARACTERISTICS:
        (A) LENGTH: 1074 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Agrobacterium rhizogenes
        (B) STRAIN: Strain A4

(vii) IMMEDIATE SOURCE:
        (A) LIBRARY: Convolvulus arvensis plant cells
        (B) CLONE: Clone 7

(ix) FEATURE:
        (A) NAME/KEY: misc_feature
        (B) LOCATION: 1..1074
        (D) OTHER INFORMATION: /label=ORF6
            / note= "Sequence ORF6 corresponds to bases 5143
            through 6216 of Seq. ID No. 19."

(xi) SEQUENCE DESCRIPTION: SEQ ID NO:6:

```
CGTACAGGTA  TCACATTTAA  CGTTGCTGCG  GCGGACCGAG  CCCGCTTGGA  AGCGATTGTT    60

GCAGCTCCAA  CTTCTGCTCA  GAAGCACGTG  TGGCGAGCGA  AGATCATCTT  GATGAGCAGT   120

GATGGCTCGG  GAACGGTCGC  GATCATGGAG  GCAACCGGTA  AATCCAAAAC  CTGTGTCTGG   180

CGCTGGCAGG  AGCGCTTCAT  GACTGAGGGC  GTCGATGGCC  TTTTGCACGA  CAAGAGCAGA   240

CCGCCCGGCA  TTGCGCCGCT  TGATGGCGAA  CTCGTTGAGC  GTGTCGTCGC  ACTGACGCTT   300

GAGACGCCTC  AACAGGAAGC  AACGCACTGG  ACTGTTCGTG  CGATGGCCAA  GGCCGTTGGG   360

ATTGCAGCCT  CTTCGGTTGT  GAAGATCTGG  CACGAGCATG  GTCTTGCGCC  GCATCGCTGG   420

CGCTCTTTCA  AACTGTCGAA  CGACAAGGCC  TTTGCCGAGA  AGCTTCACGA  CGTCGTTGGC   480

CTCTACGTCT  CGCCACCGGC  CCATGCCATT  GTCCTGTCCG  TCGATGAGAA  GAGCCAGATC   540

CAGGCACTCG  ATCGGACGCA  ACCGGGACTC  CCCTTGAAGA  AAGGGCGCGC  CGGCACAATG   600

ACCCACGATT  ACAAGCGCCA  CGGCACCACC  ACCCTATTTG  CCGCCCTCAA  CATCCTCGAC   660

GGCTCGGTGA  TCGGCCGAAA  CATGCAGCGT  CACCGGCATC  AGGAGTTCAT  CCGTTTTCTC   720

AACGCCATCG  AGGCGGAACT  GCCAAAGGAC  AAGGCCGTCC  ACGTCATTCT  CGACAATTAC   780

GCGACCCATA  AGCAGCCGAA  GGTCCGCGCC  TGGCTGGCAA  GGCATCCGCG  CTGGACCTTC   840

CACTTCGTCC  CAACATCATG  TTCATGGCTG  AACGCCGTCG  AGGGATTCTT  CGCTAAATTG   900

ACACGTCGAC  GTCTGAAGCA  CGGTGTCTTT  CATTCCGTCG  TTGACCTCCA  GGCCACCATC   960

AACCGCTTCG  TCAGAGAGCA  TAATCAGGAA  CCAAAGCCGT  TCATCTGGAG  AGCAGATCCA  1020

GACGAGATCA  TTGCAGCCGT  CAAACGTGGG  CACCAAGCGT  TGGAATCAAT  CCAC        1074
```

(2) INFORMATION FOR SEQ ID NO:7:

(i) SEQUENCE CHARACTERISTICS:

(A) LENGTH: 573 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Agrobacterium rhizogenes
(B) STRAIN: Strain A4

(vii) IMMEDIATE SOURCE:
(A) LIBRARY: Convolvulus arvensis plant cells
(B) CLONE: Clone 7

(ix) FEATURE:
(A) NAME/KEY: misc_feature
(B) LOCATION: complement (1..573)
(D) OTHER INFORMATION: /label=ORF7
/ note= "Sequence ORF7 corresponds to bases 5071 through 5643 of Seq. ID No. 19. It is read 5' to 3' from the complementary strand."

(xi) SEQUENCE DESCRIPTION: SEQ ID NO:7:

| | | | | | | |
|---|---|---|---|---|---|---|
| GTGGATTGAT | TGAAACAAAG | GAGTCCGAGT | TGGGATTCCC | TTTCGGTCTT | CGTCGTGCAA | 60 |
| CGATATCGTA | TGCGTACAGG | TATCACATTT | AACGTTGCTG | CGGCGGACCG | AGCCCGCTTG | 120 |
| GAAGCGATTG | TTGCAGCTCC | AACTTCTGCT | CAGAAGCACG | TGTGGCGAGC | GAAGATCATC | 180 |
| TTGATGAGCA | GTGATGGCTC | GGGAACGGTC | GCGATCATGG | AGGCAACCGG | TAAATCCAAA | 240 |
| ACCTGTGTCT | GGCGCTGGCA | GGAGCGCTTC | ATGACTGAGG | GCGTCGATGG | CCTTTTGCAC | 300 |
| GACAAGAGCA | GACCGCCCGG | CATTGCGCCG | CTTGATGGCG | AACTCGTTGA | GCGTGTCGTC | 360 |
| GCACTGACGC | TTGAGACGCC | TCAACAGGAA | GCAACGCACT | GGACTGTTCG | TGCGATGGCC | 420 |
| AAGGCCGTTG | GGATTGCAGC | CTCTTCGGTT | GTGAAGATCT | GGCACGAGCA | TGGTCTTGCG | 480 |
| CCGCATCGCT | GGCGCTCTTT | CAAACTGTCG | AACGACAAGG | CCTTTGCCGA | GAAGCTTCAC | 540 |
| GACGTCGTTG | GCCTCTACGT | CTCGCCACCG | GCC | | | 573 |

(2) INFORMATION FOR SEQ ID NO:8:

(i) SEQUENCE CHARACTERISTICS:
(A) LENGTH: 2279 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Agrobacterium rhizogenes
(B) STRAIN: Strain A4

(vii) IMMEDIATE SOURCE:
(A) LIBRARY: Convolvulus arvensis plant cells
(B) CLONE: Clone 7

(ix) FEATURE:
(A) NAME/KEY: misc_feature
(B) LOCATION: 1..2279
(D) OTHER INFORMATION: /label=ORF8
/ note= "Sequence ORF8 corresponds to bases 6609 through 8888 of Seq. ID No. 19."

(xi) SEQUENCE DESCRIPTION: SEQ ID NO:8:

| | | | | | | |
|---|---|---|---|---|---|---|
| GATCTTCCAT | ATCAGCGCCC | ACGTTTCACC | CCGTTTGCCG | TCACCCATCC | ACGTAGTGGA | 60 |
| GTCAACCTGA | ACCGTGCAAT | TTCTCAGGCC | TTTGTCTGCT | ATGATCAGTT | CTGCGAACGG | 120 |
| CTCTTGCGAT | ATCAGCAAAG | CTGGACGGAT | TGGGTGTTCG | ACCACGGATT | TGCAGAAGCC | 180 |
| ATTGAAGACG | TGGCGCTGGT | GTTCCAGGTT | GCACCTTGCC | TTCATGGCCC | CCGAATAGGC | 240 |

| | | | | | |
|---|---|---|---|---|---|
|GCGCTCGAAG|TGTTGATACC|TCGTCGCACC|CAGGTCTTCA|TTTATATGTC|GAACAACCAA|300|
|TTGCAGCGCT|TTGTTGCACA|CCAGTGCATT|GCTCAACTTG|GCGACGCCGT|GCTTGCTTGC|360|
|ATGATCCCGC|CCTACGCGAG|TGACCTCTCG|CTGCAGGAAA|TGGCTCGGGC|GCACAACAGA|420|
|TTTTGCCCAG|GCAGTTACAC|GAGGTCCGCA|GACGTACAGT|GCTTTATCGC|CATCCAACTC|480|
|AGCAGCCGAT|TCGTTGAGGA|GGGCACATGT|AACGTGCACG|GGCGAAATGG|CTTAAAAGA|540|
|ACCTGCCGCT|TCTTTCGTCG|CCCTGCTGAG|TTCTTCAGCC|GTTATGACAT|CGTTGCCATT|600|
|GGGCCGGTGC|TCTTCCATGA|TGAACTGGAT|TGCCCAGCAA|ACTGCAATGA|GCCTCTTTCC|660|
|TGCTTTGACC|TGCGGTACGA|CTATCAGGTT|TTCCTCCAGG|AGTGCGATGC|CCATGATGGT|720|
|GTGGGGCATT|ATCCGGAAGG|CGCACCACTA|CCTAGTGTTG|CCATCGTAGG|AGGCGGGCTG|780|
|TCTGGCCTTG|TTGCTGCCAC|AGAACTACTT|GGCGCTGGCG|TCAAGGAAAT|CACTCTTTTC|840|
|GATACCGTTG|ATGAGATCCG|TAGTTTTGGG|GCATCGCCGA|TGCCAAACGG|CGACGCTCAC|900|
|CAGGCCTTGA|CGTCGTTCGG|TGTCATGCCT|TTCTCCGCCA|ACCAACTTTG|CCTGTCATAC|960|
|TATCTGGATA|AGTTTAGAAT|TCCGTCCAGC|CTTCGTTTTC|CTTGTGCCGG|CAACGACCAC|1020|
|ACAGCACTAT|ATTTCCGCCA|GAAACGCTAC|GCATGGCACG|CGGGGCAAGC|TCCGCCGGGG|1080|
|ATATTTCAGC|GGGTACATGT|CGGATGGAAG|ACACTACTCT|ACCAAGGGTG|TGAACGGAAT|1140|
|GGCAGGAGAC|TGATGGCTCC|GATGGATATC|TCTTTCATGT|TGAAAGAGCG|TCGTCGTGAT|1200|
|GAAGCCTCAG|AAGCACGGCA|GCTTTGGCTC|CGAGAGTTCG|GAAAATTCAC|TTTCCATGCC|1260|
|GTTTTGGTCG|AGATCTTCAG|CTGTGGTAAT|TCGAGTCCTG|GTGGCAAGGC|ATGGCAAACA|1320|
|CCCCATGATT|TCGAGGCTTT|CGGGATACTG|AGGTTGGGAT|ACGGCCGAGT|TCGTCCTAT|1380|
|TACAACGTGT|TGTTTTCAAC|GATCCTGGAC|TGGATTATCA|ATGGCTACGA|GGAGGACCAG|1440|
|CATCTTTCTA|TTGGTGGGGT|TCAACTTTTG|CAGGCTCTGA|TGCGCATTGA|AATATTCCAG|1500|
|AAAAGCCATG|CGAAAGCACG|ACTCTGTTTT|GATCCCGTGC|GTGGAATAGC|CAAGGAGGGC|1560|
|GGGAGATTGA|AGGTATGCTT|GAAACACGGT|CATTCGCGTG|TTTTTGACCA|GGTCATCATT|1620|
|GGCGGCAGTG|CTGAGGCCGC|TACAGTTGAT|AACAGACTGG|CCGGGGATGA|GACTTCCTTC|1680|
|AGCTACAATA|TCGAACCCGC|CGTCGGAAAC|TCGTCTGCCG|CTGTCAATTC|AGCACTCTTC|1740|
|ATGGTCACGA|AGCAAAAGTT|TTGGGTTAAC|TCCGGCATCC|CAGCAGTGAT|ATGGACCGAT|1800|
|GGGCTTGTCC|GTGAGCTGTG|TTGCATTGAC|ATCGAATCGC|CAGCTGGAGA|GGGCCTTGTC|1860|
|GTTTTTCACT|ATGCTTTGGA|TGACTATCTA|TCCCGGCCGA|TCGAGCATCA|TGACAAGAAG|1920|
|GGACGGTGCT|TGGAATTGGT|CAGGGAGCTT|GCTGCTGCCT|TTCCTGAACT|GGCTTGTCAC|1980|
|CTGGTCCCAG|TCAACGAAGA|CTACGAACGA|TATGTCTTCG|ACGACCACCT|AACGGATGGT|2040|
|TTTAAGGGAG|CTTTGTGGAG|GGAAAATTCT|CTGGAAAAAG|GTCAGTATAT|CCAGGATCTG|2100|
|CCTGGGAATA|ATTTTCCTAT|TGGGGATCAC|GGGGGAGCCT|ATCTGATTGA|CCGTGACGAC|2160|
|TGCGTCACCG|GAGCCTCGTT|CGAGGAGCAG|GTGAAGGCGG|GCATCAAAGC|GGCCTGCGCC|2220|
|GTCATCCGCA|GCACCGGCGG|GACGCTCTCT|TCACTCCAAC|CGGTGGACTG|GAATAAAAA|2279|

( 2 ) INFORMATION FOR SEQ ID NO:9:

( i ) SEQUENCE CHARACTERISTICS:
        ( A ) LENGTH: 255 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
  ( A ) ORGANISM: Agrobacterium rhizogenes
  ( B ) STRAIN: Strain A4

( v i i ) IMMEDIATE SOURCE:
  ( A ) LIBRARY: Convolvulus arvensis plant cells
  ( B ) CLONE: Clone 7

( i x ) FEATURE:
  ( A ) NAME/KEY: misc_feature
  ( B ) LOCATION: complement (1..255)
  ( D ) OTHER INFORMATION: /label=ORF9
        / note= "Sequence ORF9 corresponds with bases 6576
        through 6830 of Seq. ID No. 19. It is read 5'to
        3'from the complementary strand."

( x i ) SEQUENCE DESCRIPTION: SEQ ID NO:9:

| | | | | | | |
|---|---|---|---|---|---|---|
| TTCTCCAAG | CAATCCTGAG | TAGCTGCGTG | ATGGATCTTC | CATATCAGCG | CCCACGTTTC | 60 |
| ACCCCGTTTG | CCGTCACCCA | TCCACGTAGT | GGAGTCAACC | TGAACCGTGC | AATTTCTCAG | 120 |
| GCCTTTGTCT | GCTATGATCA | GTTCTGCGAA | CGGCTCTTGC | GATATCAGCA | AAGCTGGACG | 180 |
| GATTGGGTGT | TCGACCACGG | ATTTGCAGAA | GCCATTGAAG | ACGTGGCGCT | GGTGTTCCAG | 240 |
| GTTGCACCTT | GCCTT | | | | | 255 |

( 2 ) INFORMATION FOR SEQ ID NO:10:

( i ) SEQUENCE CHARACTERISTICS:
    ( A ) LENGTH: 297 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Agrobacterium rhizogenes
    ( B ) STRAIN: Strain A4

( v i i ) IMMEDIATE SOURCE:
    ( A ) LIBRARY: Convolvulus arvensis plant cells
    ( B ) CLONE: Clone 7

( i x ) FEATURE:
    ( A ) NAME/KEY: misc_feature
    ( B ) LOCATION: 1..297
    ( D ) OTHER INFORMATION: /label=ORF10
          / note= "This sequence, designated ORF10,
          corresponds to bases 9748 through 10044 of
          Sequence ID No. 19. "

( x i ) SEQUENCE DESCRIPTION: SEQ ID NO:10:

| | | | | | | |
|---|---|---|---|---|---|---|
| GAATTAGCCG | GACTAAACGT | CGCCGGCATG | GCCCAGACCT | TCGGAGTATT | ATCGCTCGTC | 60 |
| TGTTCTAAGC | TTGTTAGGCG | TGCAAAGGCC | AAGAGGAAGG | CCAAACGGGT | ATCCCCGGGC | 120 |
| GAACGCGACC | ATCTTGCTGA | GCCAGCCAAT | CTGAGCACCA | CTCCTTTGGC | CATGACTTCC | 180 |
| CAAGCCCGAC | CGGGACGTTC | AACGACCCGC | GAGTTGCTGC | GAAGGGACCC | TTTGTCGCCG | 240 |
| GACGTGAAAA | TTCAGACCTA | CGGGATTAAT | ACGCATTTCG | AAACAAACCT | ACGGGAT | 297 |

( 2 ) INFORMATION FOR SEQ ID NO:11:

( i ) SEQUENCE CHARACTERISTICS:
    ( A ) LENGTH: 774 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Agrobacterium rhizogenes (B) STRAIN: Strain A4

(vii) IMMEDIATE SOURCE:
 (A) LIBRARY: Convolvulus arvensis plant cells
 (B) CLONE: Clone 7

(ix) FEATURE:
 (A) NAME/KEY: misc_feature
 (B) LOCATION: complement (1..774)
 (D) OTHER INFORMATION: /label=ORF11
  / note= "Sequence ORF11 corresponds to bases 10509
  through 11282 of Seq. ID No. 19. It is read 5'to
  3'on the complementary strand."

(xi) SEQUENCE DESCRIPTION: SEQ ID NO:11:

| | | | | | | |
|---|---|---|---|---|---|---|
| GGCTTCTTTC | TTCAGGTTTA | CTGCAGCAGG | CTTCATGACG | CCCTCCTCGC | CTTCCTGATC | 60 |
| AGGCCCCGAG | AGTCGCAGGG | TTAGGTCTGG | CTCCGGTGAG | GAGGCGGCCG | GACGTGATAT | 120 |
| CCCGAGGGCA | TTTTTGGTGA | ATTGTGTGGT | GCCGCAAGCT | ACAACATCAT | AGGGGCGGTT | 180 |
| TTCAGTCCCT | CGCCGCAGAA | AGAAGGTGCA | AGCTACCTCT | CTCCCGTAAA | CGTTGGTCAC | 240 |
| TTTTAACTCC | AGCAAGTGAA | TGAACAAGGA | ACTTGCGAAA | ATGGCGATGA | AGCATTCTAA | 300 |
| ATCAGGTTCC | TCCGTGCGGC | TGTGCGGCCA | AGCAAGGTTG | TGAACACGGA | GCATCTCCTG | 360 |
| GAGGGCGAGC | TCGCTCCGAT | ATGGTTGAAT | CGTTGTCGCC | AGCACGGCCT | CCATTCCAAA | 420 |
| TGTAATGGAT | TGTTCCTTCA | GCACTTTCTG | CATCTTCTCG | CGAGAAAGAT | AGACAAATAC | 480 |
| ATGTTGGTCG | TTTTCTCGAG | CCAGATCCGG | CTGACTAACA | AACATAGGAG | GATGATAGCA | 540 |
| GACTTTGTTC | TTCAAGAGCT | CAGCTAGTTG | TTTAAGTATA | TATATCGGTG | GAGAGTTTTC | 600 |
| CTTCAAATCT | AGCACTGCAA | GAGCCCATCG | TTTCTGGAAA | TGCAGGAGGG | GTTTGCTATA | 660 |
| GTCACGGCTA | TAGATTGCAA | AAGCAAATCG | GATCCCCTCG | AATAGGTTTA | TCTGGCTCCA | 720 |
| TGCTGGAGTG | AGATCTACTG | GTTGAAATCG | TGGAAGGAAT | AGCAATTTGG | GATC | 774 |

(2) INFORMATION FOR SEQ ID NO:12:

(i) SEQUENCE CHARACTERISTICS:
  (A) LENGTH: 537 base pairs
  (B) TYPE: nucleic acid
  (C) STRANDEDNESS: double
  (D) TOPOLOGY: linear (ii) MOLECULE TYPE: DNA (genomic)

(v) ORIGINAL SOURCE:
  (A) ORGANISM: Agrobacterium rhizogenes
  (B) STRAIN: Strain A4

(vii) IMMEDIATE SOURCE:
  (A) LIBRARY: Convolvulus arvensis plant cells
  (B) CLONE: Clone 7

(ix) FEATURE:
  (A) NAME/KEY: misc_feature
  (B) LOCATION: 1..537
  (D) OTHER INFORMATION: /label=ORF12
   / note= "Sequence ORF12 corresponds to bases 12466
   through 13002 of Seq. ID No. 19. "

(xi) SEQUENCE DESCRIPTION: SEQ ID NO:12:

| | | | | | | |
|---|---|---|---|---|---|---|
| GCTGAAGACG | ACCTGTGTTC | TCTCTTTTTC | AAGCTCAAAG | TGGAGGATGT | GACAAGCAGC | 60 |
| GATGAGCTAG | CTAGACACAT | GAAGAACGCC | TCAAATGAGC | GTAAACCCTT | GATCGAGCCG | 120 |
| GGTGAGAATC | AATCGATGGA | TATTGACGAA | GAAGGAGGGT | CGGTGGGCCA | CGGGCTGCTG | 180 |
| TACCTCTACG | TCGACTGCCC | GACGATGATG | CTCTGCTTCT | ATGGAGGGTC | CTTGCCTTAC | 240 |
| AATTGGATGC | AAGGCGCACT | CCTCACCAAC | CTTCCCCCGT | ACCAGCATGA | TGTGACTCTC | 300 |

| | | | | | |
|---|---|---|---|---|---|
| GATGAGGTCA | ATAGAGGGCT | CAGGCAAGCA | TCAGGTTTTT | TCGGTTACGC | GGATCCTATG | 360 |
| CGGAGCGCCT | ACTTCGCTGC | ATTTTCTTTC | CCTGGGCGTG | TCATCAAGCT | GAATGAGCAG | 420 |
| ATGGAGCTAA | CTTCGACAAA | GGGAAAGTGT | CTGACATTCG | ACCTCTATGC | CAGCACCCAG | 480 |
| CTTAGGTTCG | AACCTGGTGA | GTTGGTGAGG | CATGGCGAGT | GCAAGTTTGC | AATCGGC | 537 |

( 2 ) INFORMATION FOR SEQ ID NO:13:

( i ) SEQUENCE CHARACTERISTICS:
        ( A ) LENGTH: 597 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Stain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: 1..597
        ( D ) OTHER INFORMATION: /label=ORF13
            / note= "Sequence ORF13 corresponds to bases 13723
            through 14319 of Seq. ID No. 19."

( x i ) SEQUENCE DESCRIPTION: SEQ ID NO:13:

| | | | | | |
|---|---|---|---|---|---|
| GCTCGTTATT | GCAGTGGTGG | CTCTCAACGG | CTTCATGTCG | ATGATTTTCG | TTGGATCAAG | 60 |
| GAGCCCACTC | GACTGAAGGC | TCAGCTTATT | AATGTGGTGG | AGACCTACAA | GGCTGCACAA | 120 |
| ACAGAGACGT | TAAAGTACTA | TATATCATCT | GCAACTGAGC | GTGTGGCTCA | TGTGGAGGCA | 180 |
| GCCGAGGTCA | ACAATGCGGA | AATGGAGCTG | CATCCTGCTG | GGTTGAAGTA | CCCTCTGTCC | 240 |
| TTCGTCTTTA | CCTCCCTGGC | CGTGGCTACA | GCCTGCAAGG | AGAACAAGCA | TCTCTTGTGC | 300 |
| GAGGAGCATT | TGGAGGGGGA | CTTGATATCG | TGCGTCGTTC | CTCCCTATCA | GACAAATGTC | 360 |
| TCACTCGCTG | CTTTAAGGGA | GCTCCACAAT | TCCATTTCGG | GAGGAGGGTA | CCAGGAACAA | 420 |
| GCAGACATGG | ATTATTTTGT | GGCGATCATC | CCAAATGATA | ATTTCGACTA | TCAGAGCTGC | 480 |
| GAAATCGACA | CACGAAGTTG | CGGTAAAGGA | CTTTGCAAGA | TTTATAGTAG | GGAACTGGGA | 540 |
| GGGCAGCCTC | TAGCTTATGA | CGCCATACTG | GCAATCGGCA | AGGTGCTGCT | GCTGGAA | 597 |

( 2 ) INFORMATION FOR SEQ ID NO:14:

( i ) SEQUENCE CHARACTERISTICS:
        ( A ) LENGTH: 552 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: 1..552
        ( D ) OTHER INFORMATION: /label=ORF14
            / note= "Sequence ORF14 corresponds to bases 15659 through 16210 of Seq. ID No. 19."

( x i ) SEQUENCE DESCRIPTION: SEQ ID NO:14:

| | | | | | | |
|---|---|---|---|---|---|---|
| GCAGATGAGT | TGGAGCGTCA | ATTGGAAGCC | ATTTCTCTCA | TTACAGTCCT | GGGTCCGGAT | 60 |
| GTGAAGGCTG | AGCTTGAGGC | GGAGCTACGA | GACTACTGCG | AAGATCTCGA | CTTCTGGAAA | 120 |
| AGCCACGGTT | TACCGGTGGC | GGATCTCGAT | CAGACTGTGA | CTGTCGACAA | GCTTCTATAC | 180 |
| ATGTATATGG | ATCGGGCAAC | AGCAGACCTG | TGTGTGAAGA | ATCGCTGCCT | CGTTTGCAAC | 240 |
| AGTGGCAATT | CAGCCGCAAA | AGTAACCTCG | CTTCCACCAT | ACCTTGCAGG | CGTGACAAGC | 300 |
| GCCGAGGCCT | ATGAGAAACT | CAACTCCATT | GTTGATGGGA | GTGTCGCCCC | CCAATCTCGT | 360 |
| GGGCCTCCCT | GCTATTTTGT | GGCGTTCCTG | CCCAGCAGCT | GTTTCGAGAA | AACCAGTGAG | 420 |
| ATATCGGTGC | GCACAGTGGA | CGGCGAGTGT | GGCCCCTTCG | ATGTCTTTAC | CCGGCAGCGT | 480 |
| CAGCCACAGG | ATCAGAGTGA | TATGTTTTTT | AAATATGAAG | GAGTTGTATG | TGCTGGAAAG | 540 |
| AGTGTATTTA | TG | | | | | 552 |

( 2 ) INFORMATION FOR SEQ ID NO:15:

( i ) SEQUENCE CHARACTERISTICS:
        ( A ) LENGTH: 1029 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..1029)
        ( D ) OTHER INFORMATION: /label=ORF15
            / note= "Sequence ORF15 corresponds to bases 16517
            through 17545 of Seq. ID No. 19. It is read 5'to
            3'on the complementary strand."

( x i ) SEQUENCE DESCRIPTION: SEQ ID NO:15:

| | | | | | | |
|---|---|---|---|---|---|---|
| ATGCCCGTGT | TCCATCGGGC | CAGCGAGTTT | ATTCAAAAGA | GTTTCGTACA | CGTGGGCGGC | 60 |
| GACGGCAACG | TCAATGCTTG | CTAGCCCTAC | CGGCGAGAAG | TTGGCCGGCC | CCTTCCATGC | 120 |
| CTTGAGGTCA | TTCATCAAGG | CCTCGTCATC | GAGAATTTCG | GTGTAGTTCT | TGATCCCATC | 180 |
| GCGCTTGCCG | TGTTGGGTCA | GTTTCATACC | GCGCCTAGAA | TAGTAGAGGG | CAACGGCATC | 240 |
| AACGTTGCGG | GCTTCCATCG | CAACAAGGTC | ATCGGCGACA | ATTAGACCAT | CCGCAGATAG | 300 |
| GACATGCTCA | ATGTAATCCG | GCGGCATGTC | ATCAATACCG | AGTGACAAAG | TGACTGCGTT | 360 |
| GGGGGCGATT | TCAGCGGCTT | CGAATACCGG | TTTTCCGTAG | TTGGTCGCCA | TGATGACGAA | 420 |
| TTGAGAATAT | GGCAAAAGGC | TACGATCGCC | GACAGCTTCA | AGGCTAAAGG | TTACGCAATC | 480 |
| ACGTAACTTT | TCGACGAGCT | CGAAATTGGA | TTTCTTACCG | CGGCTGAGCA | CTGCTACCTT | 540 |
| ACGAATTCTC | TTAGCGGCAC | CATAGTTAAG | TGAGAGAATT | ACAGCTTCGG | CAACTTTTCC | 600 |
| AGCCCCAAAC | AAGAAAACGT | CGATGTCCTC | TCTGCCTTGC | AACAGCAGGT | TTACGCATGC | 660 |
| TAGCGAGAAC | CAACCCGTTC | TTCCATTAGA | AATTGCCACG | CCCTCTACCG | ACATAAGGAG | 720 |
| CGTCCCGGAC | ACCTTGTCGC | GCAGGAAAAT | ATCGGAGTGC | TGGAGCGGCT | TTCCGGTAGC | 780 |
| GGCGTTGGTT | GGCGCGAAGT | GGATGTCTTT | GGTGCCGGAA | TATCTTCCGA | AATAGCCAAT | 840 |

| | | | | | | |
|---|---|---|---|---|---|---|
| GAGTGCTCCT | TCAGTCCATC | CAGGAACATT | CTTGTTGAAC | GTTAGGTAAG | CTTTGACATG | 900 |
| TCCGGCTTTT | CCTGCGGCAA | ACACCTCCCA | ATAGGACTTG | AGAGCTTCGT | CAACAAATGC | 960 |
| TGGTGTGATC | TGGATATCGA | GGTTTGATAG | TGCAGATTCA | GTCCAGTGTA | CCTCGCAAAG | 1020 |
| TTGTTTGGC | | | | | | 1029 |

( 2 ) INFORMATION FOR SEQ ID NO:16:

( i ) SEQUENCE CHARACTERISTICS:
        ( A ) LENGTH: 853 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium rhizogenes
        ( B ) STRAIN: Strain A4

( v i i ) IMMEDIATE SOURCE:
        ( A ) LIBRARY: Convolvulus arvensis plant cells
        ( B ) CLONE: Clone 7

( i x ) FEATURE:
        ( A ) NAME/KEY: misc_feature
        ( B ) LOCATION: complement (1..853)
        ( D ) OTHER INFORMATION: /label=ORF16
            / note= "Sequence ORF16 corresponds to bases 17737
            through 18189 of Seq. ID No. 19. It is read 5'to
            3'on the complmentary strand."

( x i ) SEQUENCE DESCRIPTION: SEQ ID NO:16:

| | | | | | | |
|---|---|---|---|---|---|---|
| TATCTTCCGA | AATAGCCAAT | GAGTGCTCCT | TCAGTCCATC | CAGGAACATT | CTTGTTGAAC | 60 |
| GTTAGGTAAG | CTTTGACATG | TCCGGCTTTT | CCTGCGGCAA | ACACCTCCCA | ATAGGACTTG | 120 |
| AGAGCTTCGT | CAACAAATGC | TGGTGTGATC | TGGATATCGA | GGTTTGATAG | TGCAGATTCA | 180 |
| GTCCAGTGTA | CCTCGCAAAG | TTGTTTGGCC | ATCTGCCTTG | TAGGTGCGAA | TTTTCTCTGC | 240 |
| TCAAATTGTT | GAGGTTAGCG | GATTTGTAAA | CGCGTTTATA | TGGGCTGCTT | GGAGGGTACT | 300 |
| TTTGGATTAA | TTTTTTTCTG | CCAGCGCATT | CTGACGCGGC | ACCGCTTTGG | AAAGTGCGCT | 360 |
| GTGGGTCCGC | GTTTTCTACA | ATAATGTGCC | GATCCGGTCA | GAAAGTATAT | GGATGAGTTG | 420 |
| TGCCAGCCTC | ACCAACGTGC | TGCAGGCCCA | TCATGACTAC | TTCAATGTTA | ATGGGGGTAA | 480 |
| TGAATAAATA | GGCGAAATTG | GGTTCACGGT | GGGCCCAGGG | AATATAATAT | TGCCGCAGAG | 540 |
| GTAGTCGGAT | GCCAAGGCCC | GCAACTAATA | GTTCACGAAC | AAATTCATTG | TAGTGGGCGG | 600 |
| CCAACTCCAA | AACCAATTGC | CAGTTATTGT | ATTGCAATAC | ATATATGAGT | ATTCGGATAC | 660 |
| AACTAATTTC | ATTAAATAAT | ATTTTAAGTG | TGGACAGAAT | AGCGCCTAAT | AAATTTGCGA | 720 |
| ATGTTGTCCA | ATTGACGTTT | TTATAGGTAA | CTCGATAAAT | CGTGCTTTTG | TGATATTCTG | 780 |
| ATGCGGACAA | TATACATTTA | AACATAAAGA | TATAAGTTAT | TGAGGCATTT | ATGTATATTA | 840 |
| CAATAGTGGG | GTA | | | | | 853 |

( 2 ) INFORMATION FOR SEQ ID NO:17:

( i ) SEQUENCE CHARACTERISTICS:
        ( A ) LENGTH: 567 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:

(A) ORGANISM: Agrobacterium rhizogenes
(B) STRAIN: Strain A4

(vii) IMMEDIATE SOURCE:
(A) LIBRARY: Convolvulus arvensis plant cells
(B) CLONE: Clone 7

(ix) FEATURE:
(A) NAME/KEY: misc_feature
(B) LOCATION: complement (1..567)
(D) OTHER INFORMATION: /label=ORF17
/ note= "Sequence ORF17 corresponds to bases 18177 through 18743 of Seq. ID No. 19. It is read 5'to 3'on the compementary strand."

(xi) SEQUENCE DESCRIPTION: SEQ ID NO:17:

| | | | | | | |
|---|---|---|---|---|---|---|
| CAATAGTGGG | GTACATTTTT | CACAGATGCT | GTCACCCATG | AAATATTGGC | AAAATACTCT | 60 |
| TAAAATATGC | AAGAAACTAA | AGAGGATGCA | TGGGTTGGGC | TGTAGGTACA | TGGATGCAAA | 120 |
| TGCTGTTTTG | CAATAAGTCA | TATAGTCTCG | TCTGTTGAGT | GAGGCCCATT | CAATCAGCAA | 180 |
| GTAGGACTGA | GGTGCATGAT | CGACATATTT | TTGAACCACA | GTTTTGGCAA | GTTTTTCATA | 240 |
| CAAATGCACG | GCTACGGCCA | AATCGTAGCT | TGCAAGTCCA | ACTGCTGAAA | AGTTAGCCGG | 300 |
| CCCGTTCCAA | GAAATTAGCC | TTTGCATAAG | GACTGGATCG | CGGAGAACTT | CAGAGTAGTT | 360 |
| CCTGATCCCA | TTGTCCCTGC | CGTGTTTTGT | TAGCTTTAAA | TGGCGTCTTG | AATAGTGCAG | 420 |
| CGCCAACGAG | TCGATATTAC | GTGTTTCCAT | CGCATCCATA | TCATCTGCCA | CCACGATGCC | 480 |
| ACTCAGCTTC | AACACGTGAT | CAAAATAGTC | AGCTGGCAAT | TCGTCAATTC | CAAGCGTCAA | 540 |
| TGTAACGGCA | TTGTCTGTGA | TCTCCTT | | | | 567 |

(2) INFORMATION FOR SEQ ID NO:18:

(i) SEQUENCE CHARACTERISTICS:
(A) LENGTH: 360 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Agrobacterium rhizogenes
(B) STRAIN: Strain A4

(vii) IMMEDIATE SOURCE:
(A) LIBRARY: Convolvulus arvensis plant cells
(B) CLONE: Clone 7

(ix) FEATURE:
(A) NAME/KEY: misc_feature
(B) LOCATION: complement (1..360)
(D) OTHER INFORMATION: /label=ORF18
/ note= "Sequence ORF18 corresponds to bases 19031 through 19390 of Seq. ID No. 19. It is read 5'to 3'on the complementary strand."

(xi) SEQUENCE DESCRIPTION: SEQ ID NO:18:

| | | | | | | |
|---|---|---|---|---|---|---|
| GTGCCAGCCA | ACCAGTTCTC | CTCTCCGATA | TAGCCACCCC | ATCAACAGAG | AAGAGACGTC | 60 |
| TACCTGTGAA | ACGATTGCGA | AGCCAACGTC | GATGTGAGAA | GTCGGTTCTT | TGTATCTCGC | 120 |
| GTTTGACGGA | TTAGAATGGA | TGCTTTTCAC | ACCCGAATAG | TCGCCGACGA | AACCCACCAG | 180 |
| AGCTCCCTCC | GTACAGCCCT | CTCGATCAAG | TGGAACGAAG | ACCTTGTTGT | GGCCGAGCCG | 240 |
| CCCTTCAGCA | AAGAGGTGCC | AATAATCTTT | CAAGGCATCC | GCGACGAGTT | CCGGTGTAAT | 300 |
| GTATATTCCA | AAAGCCGATA | GAGATTCCTC | TGTCCAACAT | TGCTCGTGTA | TTTGATCGGC | 360 |

(2) INFORMATION FOR SEQ ID NO:19:

( i ) SEQUENCE CHARACTERISTICS:
    ( A ) LENGTH: 21126 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Agrobacterium rhizogenes
    ( B ) STRAIN: STRAIN A4

( v i i ) IMMEDIATE SOURCE:
    ( A ) LIBRARY: CONVOLVULUS ARVENSIS PLANT CELLS
    ( B ) CLONE: CLONE 7

( i x ) FEATURE:
    ( A ) NAME/KEY: misc_feature
    ( B ) LOCATION: complement (937..2262)
    ( D ) OTHER INFORMATION: /label=ORF1SUBSEQUENCE ( i x ) FEATURE:
    ( A ) NAME/KEY: misc_feature
    ( B ) LOCATION: complement (2649..3458)
    ( D ) OTHER INFORMATION: /label=ORF2SUBSEQUENCE ( i x ) FEATURE:
    ( A ) NAME/KEY: misc_feature
    ( B ) LOCATION: 3726..4799
    ( D ) OTHER INFORMATION: /label=ORF3SUBSEQUENCE ( i x ) FEATURE:
    ( A ) NAME/KEY: misc_feature
    ( B ) LOCATION: complement (4041..4400)
    ( D ) OTHER INFORMATION: /label=ORF4SUBSEQUENCE ( i x ) FEATURE:
    ( A ) NAME/KEY: misc_feature
    ( B ) LOCATION: complement (4607..4918)
    ( D ) OTHER INFORMATION: /label=ORF5SUBSEQUENCE ( i x ) FEATURE:
    ( A ) NAME/KEY: misc_feature
    ( B ) LOCATION: 5143..6216
    ( D ) OTHER INFORMATION: /label=ORF6SUBSEQUENCE ( i x ) FEATURE:
    ( A ) NAME/KEY: misc_feature
    ( B ) LOCATION: complement (5071..5643)
    ( D ) OTHER INFORMATION: /label=ORF7SUBSEQUENCE ( i x ) FEATURE:
    ( A ) NAME/KEY: misc_feature
    ( B ) LOCATION: 6609..8888
    ( D ) OTHER INFORMATION: /label=ORF8SUBSEQUENCE ( i x ) FEATURE:
    ( A ) NAME/KEY: misc_feature
    ( B ) LOCATION: complement (6576..6830)
    ( D ) OTHER INFORMATION: /label=ORF9SUBSEQUENCE ( i x ) FEATURE:
    ( A ) NAME/KEY: misc_feature
    ( B ) LOCATION: 9748..10044
    ( D ) OTHER INFORMATION: /label=ORF10SUBSEQUENC ( i x ) FEATURE:
    ( A ) NAME/KEY: misc_feature
    ( B ) LOCATION: complement (10509..11282)
    ( D ) OTHER INFORMATION: /label=ORF11SUBSEQUENC ( i x ) FEATURE:
    ( A ) NAME/KEY: misc_feature
    ( B ) LOCATION: 12466..13002
    ( D ) OTHER INFORMATION: /label=ORF12SUBSEQUENC ( i x ) FEATURE:

(A) NAME/KEY: misc_feature
(B) LOCATION: 13723..14319
(D) OTHER INFORMATION: /label=ORF13SUBSEQUENC (ix) FEATURE:
(A) NAME/KEY: misc_feature
(B) LOCATION: 15659..16210
(D) OTHER INFORMATION: /label=ORF14SUBSEQUENC (ix) FEATURE:
(A) NAME/KEY: misc_feature
(B) LOCATION: complement (16517..17545)
(D) OTHER INFORMATION: /label=ORF15SUBSEQUENC (ix) FEATURE:
(A) NAME/KEY: misc_feature
(B) LOCATION: complement (17737..18189)
(D) OTHER INFORMATION: /label=ORF16SUBSEQUENC (ix) FEATURE:
(A) NAME/KEY: misc_feature
(B) LOCATION: complement (18177..18743)
(D) OTHER INFORMATION: /label=ORF17SUBSEQUENC (ix) FEATURE:
(A) NAME/KEY: misc_feature
(B) LOCATION: complement (19031..19390)
(D) OTHER INFORMATION: /label=ORF18SUBSEQUENC (xi) SEQUENCE DESCRIPTION: SEQ ID NO:19:

| | | | | | |
|---|---|---|---|---|---|
| GGCCGCAGGA | TTTCGTTCGT | CGTGCGTGAT | GAGATCGATA | AATGTTTATC | GACGAGGACA | 60 |
| AGATCGACGA | TGCGGTTCTT | GCGCTGTTGT | AGTGACGCTC | CACAACGAGT | GTTGCGCCGT | 120 |
| GAAAGGCTTT | GACTGGGCCG | CGACGGACCG | CCTTTGCAGG | AAGGGTTCGG | TCGGCGATCC | 180 |
| CGTCAATAAA | TCGAAGCTAT | TGATCCTGAC | GGATAAAGGT | CTGCGTCGAT | CGGAGGAGCT | 240 |
| ATTCCGACAG | CTGTTTACGC | GCTAGCCATT | GGCCGACGGT | CTTTGCGCCC | TCCATTCCCA | 300 |
| CGGCGTAGTT | AATGCCGGCG | GGACGGGAG | TGTCTACTAT | GTGCAAGCAC | GTCGGCGAAC | 360 |
| CATGCCTTCG | GATTAATGTC | GTTCAGACGG | GCGGTCGTAA | GTTGAATGAG | TATGACTGCC | 420 |
| GCATGGTCAG | CGCCGCGTTG | GGAGCCGGCA | GATGTCCAGT | CGCGGCGCCT | CAAGGCCATC | 480 |
| ACATGTTCAC | TCTGTGGCCA | GAAGGCGTCG | CTCCTTGGGT | GGCAGGATAT | ATTGTGATGT | 540 |
| AAACAGATTA | GATATGGACA | TGCGAAGTCG | TTTTAACGCA | TGCTTTATCG | AATATAAAAT | 600 |
| GTAGATGGGC | TAATGTGGTT | TTACGTCATG | TGAATAAAAG | TTCAGCATTC | GTTTAATAAT | 660 |
| ATTTCAATAT | CGGTGTCTAG | AGACCCGTGG | ATTTGTATAG | TCAGCACCAT | GATATGAATC | 720 |
| TATAAAATAT | TGTATCTCCA | ATTGCAATTC | AATCGATATA | AGAAATTAAT | ACAAGCCGTT | 780 |
| CATATAGTAA | GGTTGCCAAT | GGCATTCAAT | AACGACCGTA | CAGTTGCCGC | TATATTAATC | 840 |
| TACGTGCCAT | TTCTTAAATA | AAGATAGGCG | AATGACTATC | GAAAATAAAA | CAATTATTAA | 900 |
| TGAGTGAAAA | CGTATTGCAC | AAATAAAGAT | TCATTATGGT | TGGCTCAAAT | TTTGGCTCTG | 960 |
| GTGCTCGATG | ACGTCGAGAT | GAGGACAGTA | GTGATCAACT | TGGCGGTCGA | TACCTTGGTT | 1020 |
| ACGCCACTCC | CAGAGTGCCA | TGTCGTCCTC | CGAGCGGTCT | GAGATAACCC | AGTCGGCAAT | 1080 |
| TGCTGCTGCA | TTGCCGGGCG | TTCCCCAACC | ACGACGAATA | TGCTTTCGTT | CATCTAACTC | 1140 |
| GCGTCGCACT | GCCCTCCCAG | TCATGAAGTC | AAAGCCAAAT | TCTACCCTCT | CTCCATTTCC | 1200 |
| CAGCTCAGTC | GAGAAATCGT | AACACCTCGT | GGCAGCTGAC | AGTTTCAGAA | AGGGGCGTAT | 1260 |
| CCCTCGAACT | CCAGGGTCCT | CTTTCACATA | GTTAGCAAGG | CGTACTGCTG | CATAATCTGC | 1320 |
| GTTGAAGGCT | CTGATGACTA | CAGGATCCTC | GGACAAGCCC | AATTGATCAG | GCGAACCCT | 1380 |
| CGCGCTCATA | ATATGAATTG | CGACGACCCT | TGCTTCCTGT | CGGAGCATCG | AATCAATCCA | 1440 |
| AGCCTTCCCT | GCGGCATAGA | GGTCATCGAC | TGCGATGTCA | TCAAGATCGA | GTAGCTTTGC | 1500 |

| | | | | | | |
|---|---|---|---|---|---|---|
| CAACCTAGGA | AGTTCTTGAG | GAAAAATCAC | CGGCATGACA | GCAACCGTCT | CTCGCCAGTC | 1560 |
| AGTTGCCGGA | CTGGCTTCCC | TAACGCCATC | CACGAATGCC | TCACCGCTTG | CGTATTTGAA | 1620 |
| TGTGTAAAAG | AGAAGGACCA | CTCTTTGGCG | GTACTTCGGA | CGCCGGCTTA | GCCACGCGGC | 1680 |
| AATAATGTGG | GCCTCAAACT | CACGACCATC | CAAAATATA | GTCGCGCCTG | GATTGACCTC | 1740 |
| GCTGGCCTTG | TCGAGAAGAG | GTTCCAAAAA | GGGAACGGTG | TCTTTCGTAA | TAGTACTTAA | 1800 |
| ATCTGTGAGT | TCGCCATGCG | AAACCTCTCG | AACGATTATC | GGCGTATCCC | TGACATCAGC | 1860 |
| TGAATGAAAT | TCTCGGACGA | GTTTGTCGGG | CAAAGTGGAG | ACCCGCCACG | TGTTGAAGTC | 1920 |
| GTGGGAAACG | ATGGGCACAT | CGTCGCCGGT | GAGTGCGGCA | TCGAGCTCAG | AGAGGTTCCG | 1980 |
| CCTGCCAACC | TCACCGAGAG | CAGCTAACAA | CGAAGTTTCG | GTGCATTCCT | GTATCCCTTT | 2040 |
| ACCCAGATTA | TACATGCCCC | GGTGTTCGAT | AACTTGAAGA | GGCAGTGGCT | CCTCAAGATG | 2100 |
| TTCAAGGAGG | TGGGGTACAG | AGTGCCGGGC | GAGGACCTCA | TCCACCGTGA | CACCAACCGG | 2160 |
| GAGATCCCAT | TCGAGTTTCC | ACTGGGGCCA | GCATGTGCCC | GCGACGGCGA | AAGGTTTGCG | 2220 |
| CTGGCAAAGA | ACCCGGCTGC | TGCAGGTGGA | CCTATCCTTA | CCCATGGCAA | TGGGGTTTTG | 2280 |
| CTAAAAAGTC | AGGCACTTTA | CTGGGCAATT | GATAGGGTGG | GATTGCGTTA | TTAACTGTTC | 2340 |
| TCCAGCGGGA | ATCTTTATCT | TTATTGAAAT | GCTAAAGCAC | TTAGATAAAA | TACAGCTGTA | 2400 |
| CCGCAATATA | AAATAGTAGG | ATAATGTAAT | ATGTGTATCG | AGAATACGAC | AAGCTAATAT | 2460 |
| AATCTAGCGT | CAAATTGCAA | TAATTTAAAT | CAAAACTACT | GATGAAATAA | TAAAGATGG | 2520 |
| TCAATTTTTA | TTGGTAGGAG | TTGTCGAAAG | ATTCGACGGA | CGGCCATTAC | AATACATAGG | 2580 |
| TGCAAGAAGT | AAAACAGGAA | GGGAAACGGA | AAACAGTGCT | ATAAAAAGC | GACAGATCGC | 2640 |
| GGCGATCACT | GACTGCGATC | GGGAAGAAGC | TCGCCAAGTT | CACCGAGAAT | AGCAGAGAGC | 2700 |
| GCATCCTCAT | CGGGTACTAC | GAACACATTC | GTCCCAGAGG | GCTTTGTTTC | AGCTGCGCCA | 2760 |
| ACCCAGAAAG | CAAGGCCATT | TTCCAAGTTG | CCGATGGCGG | TCAGCATGTT | TTGATTGTTG | 2820 |
| CTGCCGTTTC | CACAAGCGAT | GTGAAGGCCG | ATCCCGTGAG | AGAGGCCCTT | GACGAAGGTG | 2880 |
| AAATAGCCTT | TGGATTTTCC | AACTGTTTCA | ACGGGCACTA | GATATTGACC | CTCTGGCGCG | 2940 |
| GCAACCACCT | TGAATTTGCG | AGATGACTGG | TTGCCGATGA | GCGAAGAAAG | CATTTCTCCG | 3000 |
| GCTTCTTTGT | AAGATTTGTG | AGATTCCCAC | ATTTGACAGC | CGTAGAAATG | CCCCATCGGA | 3060 |
| ATGTTGCGGA | TTCCCGGGAT | GCCACCAAAT | TTGTTCTCCA | TAGCCGCGTG | AACGGCTTGC | 3120 |
| CAGTTGGGCA | GGGAGAAAGA | ATCGAAGCGA | TCATCTTTGT | AGATCGTGAC | CATTCCATCA | 3180 |
| TTTCCCTGGA | ATCCGATATT | TTCAATGGCG | CTGAAAACTG | ACCTTGCGAT | TTCTTCGCAT | 3240 |
| TCCCGTGCGG | ATGTGAGCAA | TTGATAATGG | CCCTTGCAGG | CGATCCTGGT | CAAATTGGCG | 3300 |
| ATGATGTTGA | TGGCAGGATT | AATATCCCAA | CACTGGTGAT | TTCGATCTTG | CTTAAGGTG | 3360 |
| GTACCATCGC | CGTCGAAGGC | GAGCAGGGCC | CGGAGAGATG | AATCGGCAAG | ACTGCGTCGG | 3420 |
| ACCCGCTCCG | CGGCGTCGGG | AATGAGGCTG | ATAAGAGACA | TATCCAAAGG | TGTTTGTGGG | 3480 |
| TAACGGGCTG | CTCAATGAAG | CCTTAAATGC | AACGCAACAT | ATGTAAGGAT | GAGTTGACTT | 3540 |
| ATTGGAGAGA | GAAATAGGAA | TGAGCTGGCC | AGCCATTATC | AACGTGGGGC | CATGCTGACA | 3600 |
| ATGTTTACGT | GAAAGGCTCA | ACTACCTCGA | AGCAGACCTC | TATATTCGTT | GACTTTATTA | 3660 |
| CTGAACAAGA | AGTTGCTTGC | CACTCATTTT | CTTAAATCTT | GCCCTTTCTG | CGCCTCGCTA | 3720 |
| TCATGCCCGC | CAACGACGCG | ACATGCGCTG | CCGCGATTGC | CTTCCCGAG | GCAACTGGA | 3780 |
| AGGAAGAACT | TGATGCGCTC | CGCACCTTGT | GTGACCCCGT | CGAGGTGGTT | AAGGTCGCAG | 3840 |
| TCGGCAGAGG | TCTTAGCGGC | ATATGTAATG | TTGTTGCAGC | AATGAATCCC | ACAAAGGTGA | 3900 |

```
GGGGCCTCGG CGATGTCATC GGGCAGATGC CGGCTCTTAA TCACCGTATT GCTGCCGCCG   3960
CCGGCGAAAC TCCGGTGCGA GACCTTGGAA TAGGTTACCA GTGCGCAATC TGCCACCCCG   4020
ACATAGCCAG TGCGATGTTA GCCACTTCTG AGGGGATCAG CCACGTTCTC CGTGAAAGGA   4080
TTGAGAAAGA AGTTGACCGG GACATTGGAG AAGGCGCCAC CGTCTGCATT TTCGTTCAGC   4140
CGAGAATGAG CTCCAAGGGC TCTCCAGTTT CTGTCCATTT CACCCTCCAG TTTGCGAGAT   4200
CTGGAACTCT TGTCGATGCC AGAATGATGG AGAGTTACAA TTTCATGAAA GGCAATGGCA   4260
CAGTGACCGC ACCGGATTTG AAAAGTCATT GGAAGAAGCA CGGTATTGAC AGGCCAGGCC   4320
CACGTCCGCC CACGTCCAAG TTTGAACTCC TCTTCGCCGC TGTCCCCGAC AACAGTAAAC   4380
TTGCCGCCAC CGATTTTACC CATCTCGGCC CTGTCGAGCG TGATAAGGAA CTACTCGGCA   4440
GCACGGTATT CGGGATTGCC GCTAAGAAAC TGGTACGAT CGTTTATCCG TGCGAAAAGG    4500
TTCTCTGTTT GGAGGTCGAC GTACACGCGC ATCGCGCCCT AGAAGTACTT CACCGCCTTG   4560
GGGAACAGGC TTATAGCAAT GGCCGTGGCA CTAGCTTCGG TCTTCACACC GGTCCGTCCT   4620
CTTGCCTTAA TCTTTCCGCC GCCGCGCTCG CTACATTTTT CAAACGCTCG GATCTCTGTT   4680
CCCTTCCATT GAGTGATGCT TTTGTCCTTT TCTGCGACCC GCCACCGCCT ACAGCGCCAA   4740
GAAAGATGGC CTTCCGATCA CTGCCTTCTC CCCCACGAGC ACCAATCAGT TCGAACTCGT   4800
AGAGCCTCAG GTCGTCAAGG CATATGTTCT CGGACTTTTC GACGCGCCGA CGATGGTTAC   4860
GCCCCGCGAC AAAACGCGAG CCAGCTTCTG CAGCCAATAT GTACGTTTCC GTGAACCGCA   4920
TCCCTGTGAA GAGTTCAATG AAATTGGAGT TTTGATCCTC GATGCTGCTG CTAAAATGCT   4980
CGAACGTTAT GCAAAATTTC TAGAAGATGG TGGAAGAGAT GATGATGAAA TGGCGAACAT   5040
AATAGATGTA TTTGGGTTTT GTCTTAACTA GTGGATTGAT TGAAACAAAG GAGTCCGAGT   5100
TGGGATTCCC TTTCGGTCTT CGTCGTGCAA CGATATCGTA TGCGTACAGG TATCACATTT   5160
AACGTTGCTG CGGCGGACCG AGCCCGCTTG GAAGCGATTG TTGCAGCTCC AACTTCTGCT   5220
CAGAAGCACG TGTGGCGAGC GAAGATCATC TTGATGAGCA GTGATGGCTC GGGAACGGTC   5280
GCGATCATGG AGGCAACCGG TAAATCCAAA ACCTGTGTCT GGCGCTGGCA GGAGCGCTTC   5340
ATGACTGAGG GCGTCGATGG CCTTTTGCAC GACAAGAGCA GACCGCCCGG CATTGCGCCG   5400
CTTGATGGCG AACTCGTTGA GCGTGTCGTC GCACTGACGC TTGAGACGCC TCAACAGGAA   5460
GCAACGCACT GGACTGTTCG TGCGATGGCC AAGGCCGTTG GGATTGCAGC CTCTTCGGTT   5520
GTGAAGATCT GGCACGAGCA TGGTCTTGCG CCGCATCGCT GGCGCTCTTT CAAACTGTCG   5580
AACGACAAGG CCTTTGCCGA GAAGCTTCAC GACGTCGTTG GCCTCTACGT CTCGCCACCG   5640
GCCCATGCCA TTGTCCTGTC CGTCGATGAG AAGAGCCAGA TCCAGGCACT CGATCGGACG   5700
CAACCGGGAC TCCCCTTGAA GAAAGGGCGC GCCGGCACAA TGACCCACGA TTACAAGCGC   5760
CACGGCACCA CCACCCTATT TGCCGCCCTC AACATCCTCG ACGGCTCGGT GATCGGCCGA   5820
AACATGCAGC GTCACCGGCA TCAGGAGTTC ATCCGTTTTC TCAACGCCAT CGAGGCGGAA   5880
CTGCCAAAGG ACAAGGCCGT CCACGTCATT CTCGACAATT ACGCGACCCA TAAGCAGCCG   5940
AAGGTCCGCG CCTGGCTGGC AAGGCATCCG CGCTGGACCT TCCACTTCGT CCCAACATCA   6000
TGTTCATGGC TGAACGCCGT CGAGGGATTC TTCGCTAAAT TGACACGTCG ACGTCTGAAG   6060
CACGGTGTCT TTCATTCCGT CGTTGACCTC CAGGCCACCA TCAACCGCTT CGTCAGAGAG   6120
CATAATCAGG AACCAAAGCC GTTCATCTGG AGAGCAGATC CAGACGAGAT CATTGCAGCC   6180
GTCAAACGTG GGCACCAAGC GTTGGAATCA ATCCACTAGC GTATGAACAG TAATAAGAAA   6240
ATCCCGATTG TGAATAGTCC CAATTTCAAA TGTGTCCGTG TGTAATTTGC GTGTCTTCAG   6300
```

```
TTGAATTTCC TTTAATAATA TCAAATATTC AATTGTGAAA AGTTGTATTG GTTCAGGTTC    6360
AAGCTTTCCG AATTTGTTGA ATTTTATTCC CTGTTTTCAA TTTGTTGACT TGTTTGGGAG    6420
ACACCTTTTT TGTGTTTCGT GAACATGTCA CCCCTTCGGT ATACATTAGC CTACAAAGTA    6480
AATAACGTTG ATAAATGTCA CTCATGTTGT AATAAAATTG AGCTTATTAT GTATAACCAG    6540
ACCCTGTGTT AATCTAATTA CAAAGAAATT CATCATTCTC CCAAGCAATC CTGAGTAGCT    6600
GCGTGATGGA TCTTCCATAT CAGCGCCCAC GTTTCACCCC GTTTGCCGTC ACCCATCCAC    6660
GTAGTGGAGT CAACCTGAAC CGTGCAATTT CTCAGGCCTT TGTCTGCTAT GATCAGTTCT    6720
GCGAACGGCT CTTGCGATAT CAGCAAAGCT GGACGGATTG GGTGTTCGAC CACGGATTTG    6780
CAGAAGCCAT TGAAGACGTG GCGCTGGTGT TCCAGGTTGC ACCTTGCCTT CATGGCCCCC    6840
GAATAGGCGC GCTCGAAGTG TTGATACCTC GTCGCACCCA GGTCTTCATT TATATGTCGA    6900
ACAACCAATT GCAGCGCTTT GTTGCACACC AGTGCATTGC TCAACTTGGC GACGCCGTGC    6960
TTGCTTGCAT GATCCCGCCC TACGCGAGTG ACCTCTCGCT GCAGGAAATG GCTCGGGCGC    7020
ACAACAGATT TTGCCCAGGC AGTTACACGA GGTCCGCAGA CGTACAGTGC TTTATCGCCA    7080
TCCAACTCAG CAGCCGATTC GTTGAGGAGG GCACATGTAA CGTGCACGGG CGAAATGGCT    7140
TAAAAGAAC CTGCCGCTTC TTTCGTCGCC CTGCTGAGTT CTTCAGCCGT TATGACATCG     7200
TTGCCATTGG GCCGGTGCTC TTCCATGATG AACTGGATTG CCCAGCAAAC TGCAATGAGC    7260
CTCTTTCCTG CTTTGACCTG CGGTACGACT ATCAGGTTTT CCTCCAGGAG TGCGATGCCC    7320
ATGATGGTGT GGGGCATTAT CCGGAAGGCG CACCACTACC TAGTGTTGCC ATCGTAGGAG    7380
GCGGGCTGTC TGGCCTTGTT GCTGCCACAG AACTACTTGG CGCTGGCGTC AAGGAAATCA    7440
CTCTTTTCGA TACCGTTGAT GAGATCCGTA GTTTTGGGGC ATCGCCGATG CCAAACGGCG    7500
ACGCTCACCA GGCCTTGACG TCGTTCGGTG TCATGCCTTT CTCCGCCAAC CAACTTTGCC    7560
TGTCATACTA TCTGGATAAG TTTAGAATTC CGTCCAGCCT TCGTTTTCCT TGTGCCGGCA    7620
ACGACCACAC AGCACTATAT TTCCGCCAGA AACGCTACGC ATGGCACGCG GGCAAGCTC     7680
CGCCGGGGAT ATTTCAGCGG GTACATGTCG GATGGAAGAC ACTACTCTAC CAAGGGTGTG    7740
AACGGAATGG CAGGAGACTG ATGGCTCCGA TGGATATCTC TTTCATGTTG AAAGAGCGTC    7800
GTCGTGATGA AGCCTCAGAA GCACGGCAGC TTTGGCTCCG AGAGTTCGGA AAATTCACTT    7860
TCCATGCCGT TTTGGTCGAG ATCTTCAGCT GTGGTAATTC GAGTCCTGGT GGCAAGGCAT    7920
GGCAAACACC CCATGATTTC GAGGCTTTCG GGATACTGAG GTTGGGATAC GGCCGAGTTT    7980
CGTCCTATTA CAACGTGTTG TTTTCAACGA TCCTGGACTG GATTATCAAT GGCTACGAGG    8040
AGGACCAGCA TCTTTCTATT GGTGGGGTTC AACTTTTGCA GGCTCTGATG CGCATTGAAA    8100
TATTCCAGAA AAGCCATGCG AAAGCACGAC TCTGTTTTGA TCCCGTGCGT GGAATAGCCA    8160
AGGAGGGCGG GAGATTGAAG GTATGCTTGA AACACGGTCA TTCGCGTGTT TTTGACCAGG    8220
TCATCATTGG CGGCAGTGCT GAGGCCGCTA CAGTTGATAA CAGACTGGCC GGGGATGAGA    8280
CTTCCTTCAG CTACAATATC GAACCCGCCG TCGGAAACTC GTCTGCCGCT GTCAATTCAG    8340
CACTCTTCAT GGTCACGAAG CAAAAGTTTT GGGTTAACTC CGGCATCCCA GCAGTGATAT    8400
GGACCGATGG GCTTGTCCGT GAGCTGTGTT GCATTGACAT CGAATCGCCA GCTGGAGAGG    8460
GCCTTGTCGT TTTTCACTAT GCTTTGGATG ACTATCTATC CCGGCCGATC GAGCATCATG    8520
ACAAGAAGGG ACGGTGCTTG GAATTGGTCA GGGAGCTTGC TGCTGCCTTT CCTGAACTGG    8580
CTTGTCACCT GGTCCCAGTC AACGAAGACT ACGAACGATA TGTCTTCGAC GACCACCTAA    8640
CGGATGGTTT TAAGGGAGCT TTGTGGAGGG AAAATTCTCT GGAAAAAGGT CAGTATATCC    8700
```

| | | | | | | |
|---|---|---|---|---|---|---|
| AGGATCTGCC | TGGGAATAAT | TTTCCTATTG | GGGATCACGG | GGGAGCCTAT | CTGATTGACC | 8760 |
| GTGACGACTG | CGTCACCGGA | GCCTCGTTCG | AGGAGCAGGT | GAAGGCGGGC | ATCAAAGCGG | 8820 |
| CCTGCGCCGT | CATCCGCAGC | ACCGGCGGGA | CGCTCTCTTC | ACTCCAACCG | GTGGACTGGA | 8880 |
| ATAAAAAATA | GAAATTTCCT | GATTAAGTTA | TAGTCAATGT | ACTATTGCGT | GTTAATCCCG | 8940 |
| TAGGTATGCA | AGCTGCACCG | GCAGCATCAT | AATTTGATGT | TCCATCAATA | AATTAAGGTG | 9000 |
| CCCGTTCATT | GTGTATTACA | TTATGTATGT | TTATCAAAAA | TATAATCGAA | GTCCATTTTA | 9060 |
| AGTCTGATAT | TAATTGGAAT | TCCAAACGAT | TCCTTGATGC | CTATCTTCGC | TATGATTGTA | 9120 |
| TGGTAATAAA | GTCTCCACAT | CTCCCGAAAA | ATGCTTTCGT | GATTTACTTG | TCTCTCACGT | 9180 |
| GCTTTCGCAT | CTTGACAGCC | AAAAGTGGGC | AACTTGAGAA | GAGTATTAAC | TGGCCACGCA | 9240 |
| ACTCGAGATA | TTCCCACTAA | CCCCAATGAC | GTCATTGCAC | TCGTCACGGG | TAGCAGCCCC | 9300 |
| ACTTGCCTTT | GCCACTTTAT | TAATTCTTTG | GCCCACTGGC | CATTAATTGG | CACCTACATA | 9360 |
| TATTAGTGGA | GAAGATAAAG | TGTCACTATC | GTTTCCTGTT | CAATTTTGAA | TTTTGCAAGG | 9420 |
| ATTTCATGTT | GTCAACTACA | CAGCTTGAAA | GGAAATCCGC | AATCAACGGA | GAAACGTCAA | 9480 |
| CATCTCGACA | AAAAAAGAAT | GCTTCATCAT | TGCGTAGACT | GCATATTGAC | CGCTCCTTTC | 9540 |
| GGCGCTGGGC | CTGCTTTTAC | TGTTGCCTAG | CGTTCGGACA | GCCACCAGAG | AATGGGCTAT | 9600 |
| ATAGATCCTT | TCATCAAACC | AAAACATTAC | TAAGATCATG | CTGTAACGCT | TCAATACGGT | 9660 |
| GAGTGTGGTT | GTAGGTTCAA | TTATTACTAT | TTTGAAGCT | GTGTATTTCC | CTTTTTCTAA | 9720 |
| TATGCACCTA | TTTCATGTTT | CAGAATGGAA | TTAGCCGGAC | TAAACGTCGC | CGGCATGGCC | 9780 |
| CAGACCTTCG | GAGTATTATC | GCTCGTCTGT | TCTAAGCTTG | TTAGGCGTGC | AAAGGCCAAG | 9840 |
| AGGAAGGCCA | AACGGGTATC | CCCGGGCGAA | CGCGACCATC | TTGCTGAGCC | AGCCAATCTG | 9900 |
| AGCACCACTC | CTTTGGCCAT | GACTTCCCAA | GCCCGACCGG | GACGTTCAAC | GACCCGCGAG | 9960 |
| TTGCTGCGAA | GGGACCCTTT | GTCGCCGGAC | GTGAAAATTC | AGACCTACGG | GATTAATACG | 10020 |
| CATTTCGAAA | CAAACCTACG | GGATTAATAC | GCACGTGGCT | GGCGGTCTTC | GATTCATTTC | 10080 |
| CACGCCGGAG | ATGATATCGA | ATATGTTCTG | TTAAGTTAAA | ATAAGCTGCG | AGCCATGGCG | 10140 |
| CGATTGTCCT | GTTTTATTAA | TATAGTACTT | TAACGTCTCT | TTAGAGCGTT | TGTGTAATGT | 10200 |
| CGTGAAAATG | TTTTATGTCA | AATGTACTGT | TGAACTATAA | TATTATAAGT | CCAGGTGTGT | 10260 |
| CGTTGTTGTT | GATACTGCAA | TATATGTGTA | GTAGATTAGA | TAGTCATATG | AGCATGTGCT | 10320 |
| GTTTTTGGCA | AAATTCAGCA | GCAGGATCAA | CACAGAAGAA | AATATTTAGT | ACAAGAAAAT | 10380 |
| AGGTCAACAC | ATTACAACGT | ACGCTACAAC | TCCCAAGGTT | CTGTGTCACA | GACTGCGGGA | 10440 |
| GGGTACATAG | AACTTATGAC | AAACTCATAG | ATAAAGGTTG | CCTGCAGGGG | GAGTTCAAGT | 10500 |
| CGGCTTTAGG | CTTCTTTCTT | CAGGTTTACT | GCAGCAGGCT | TCATGACGCC | CTCCTCGCCT | 10560 |
| TCCTGATCAG | GCCCCGAGAG | TCGCAGGGTT | AGGTCTGGCT | CCGGTGAGGA | GGCGGCCGGA | 10620 |
| CGTGATATCC | CGAGGGCATT | TTTGGTGAAT | TGTGTGGTGC | CGCAAGCTAC | AACATCATAG | 10680 |
| GGGCGGTTTT | CAGTCCCTCG | CCGCAGAAAG | AAGGTGCAAG | CTACCTCTCT | CCCGTAAACG | 10740 |
| TTGGTCACTT | TTAACTCCAG | CAAGTGAATG | AACAAGGAAC | TTGCGAAAAT | GGCGATGAAG | 10800 |
| CATTCTAAAT | CAGGTTCCTC | CGTGCGGCTG | TGCGGCCAAG | CAAGGTTGTG | AACACGGAGC | 10860 |
| ATCTCCTGGA | GGGCGAGCTC | GCTCCGATAT | GGTTGAATCG | TTGTCGCCAG | CACGGCCTCC | 10920 |
| ATTCCAAATG | TAATGGATTG | TTCCTTCAGC | ACTTTCTGCA | TCTTCTCGCG | AGAAAGATAG | 10980 |
| ACAAATACAT | GTTGGTCGTT | TTCTCGAGCC | AGATCCGGCT | GACTAACAAA | CATAGGAGGA | 11040 |
| TGATAGCAGA | CTTTGTTCTT | CAAGAGCTCA | GCTAGTTGTT | TAAGTATATA | TATCGGTGGA | 11100 |

```
GAGTTTTCCT  TCAAATCTAG  CACTGCAAGA  GCCCATCGTT  TCTGGAAATG  CAGGAGGGGT   11160
TTGCTATAGT  CACGGCTATA  GATTGCAAAA  GCAAATCGGA  TCCCCTCGAA  TAGGTTTATC   11220
TGGCTCCATG  CTGGAGTGAG  ATCTACTGGT  TGAAATCGTG  GAAGGAATAG  CAATTTGGGA   11280
TCCATTGTGA  TGTGAGTTGG  ATAGTTACGA  AAAAGGCAAG  TGCCAGGGCC  ATTTAAAATA   11340
CGGCGTCGGA  AACTGGCGCC  AATCAGACAC  AGTCTCTGGT  CGGGAAAGCC  AGAGGTAGTT   11400
TGGCAACAAT  CACATCAAGA  TCGATGCGCA  AGACACGGGA  GGCCTTAAAA  TCTGGATCAA   11460
GCGAAAATAC  TGCATGCGTG  ATCGTTCATG  GGTTCATAGT  ACTGGGTTTG  CTTTTCTTG    11520
TCGTGTTGTT  TGGCCTTAGC  GAAAGGATGT  CAAAAAAGGA  TGCCCATAAT  TGGGAGGAGT   11580
GGGGTAAAGC  TTAAAGTTGG  CCCGCTATTG  GATTTCGCGA  AAGCGGCATT  GGCAAACGTG   11640
AAGATTGCTG  CATTCAAGAT  ACTTTTTCTA  TTTTCTGGTT  AAGATGTAAA  GTATTGCCAC   11700
AATCATATTA  ATTACTAACA  TTGTATATGT  AATATAGTGC  GGAAATTATC  TATGCCAAAA   11760
TGATGTATTA  ATAATAGCAA  TAATAATATG  TGTTAATCTT  TTTCAATCGG  GAATACGTTT   11820
AAGCGATTAT  CGTGTTGAAT  AAATTATTCC  AAAAGGAAAT  ACATGGTTTT  GGAGAACCTG   11880
CTATAGATAT  ATGCCAAATT  TACACTAGTT  TAGTGGGTGC  AAAACTATTA  TCTCTGTTTC   11940
TGAGTTTAAT  AAAAAATAAA  TAAGCAGGGC  GAATAGCAGT  TAGCCTAAGA  AGGAATGGTG   12000
GCCATGTACG  TGCTTTTAAG  AGACCCTATA  ATAAATTGCC  AGCTGTGTTG  CTTTGGTGCC   12060
GACAGGCCTA  ACGTGGGGTT  TAGCTTGACA  AAGTAGCGCC  TTTCCGCAGC  ATAAATAAAG   12120
GTAGGCGGGT  GCGTCCCATT  ATTAAAGGAA  AAAGCAAAAG  CTGAGATTCC  ATAGACCACA   12180
AACCACCATT  ATTGGAGGAC  AGAACCTATT  CCCTCACGTG  GGTCGCTAGC  TTTAAACCTA   12240
ATAAGTAAAA  ACAATTAAAA  GCAGGCAGGT  GTCCCTTCTA  TATTCGCACA  ACGAGGCGAC   12300
GTGGAGCATC  GACAGCCGCA  TCCATTAATT  AATAAATTTG  TGGACCTATA  CCTAACTCAA   12360
ATATTTTTAT  TATTTGCTCC  AATACGCTAA  GAGCTCTGGA  TTATAAATAG  TTTGGATGCT   12420
TCGAGTTATG  GGTACAAGCA  ACCTGTTTCC  TACTTTGTTA  ACATGGCTGA  AGACGACCTG   12480
TGTTCTCTCT  TTTTCAAGCT  CAAAGTGGAG  GATGTGACAA  GCAGCGATGA  GCTAGCTAGA   12540
CACATGAAGA  ACGCCTCAAA  TGAGCGTAAA  CCCTTGATCG  AGCCGGGTGA  GAATCAATCG   12600
ATGGATATTG  ACGAAGAAGG  AGGGTCGGTG  GGCCACGGGC  TGCTGTACCT  CTACGTCGAC   12660
TGCCCGACGA  TGATGCTCTG  CTTCTATGGA  GGGTCCTTGC  CTTACAATTG  GATGCAAGGC   12720
GCACTCCTCA  CCAACCTTCC  CCCGTACCAG  CATGATGTGA  CTCTCGATGA  GGTCAATAGA   12780
GGGCTCAGGC  AAGCATCAGG  TTTTTTCGGT  TACGCGGATC  CTATGCGGAG  CGCCTACTTC   12840
GCTGCATTTT  CTTTCCCTGG  GCGTGTCATC  AAGCTGAATG  AGCAGATGGA  GCTAACTTCG   12900
ACAAAGGGAA  AGTGTCTGAC  ATTCGACCTC  TATGCCAGCA  CCCAGCTTAG  GTTCGAACCT   12960
GGTGAGTTGG  TGAGGCATGG  CGAGTGCAAG  TTTGCAATCG  GCTAATGGTT  AGTCGATGGG   13020
CTGACGAGTT  TGATGTCAGG  AGAAGCTGAG  TGTGTCACTT  GTTTCCCTTT  AAGAAGTATT   13080
AATGTAATAA  AAATCAAGAT  CTGGTTTAAT  AACTGGATAC  TTGATTTCAT  CGCGCTTTTT   13140
TTGAATAAAT  GTTTGTTGTC  TTGACTTTAA  GATATCCTTT  GAAATTTGCG  TTATTCGTAT   13200
TTCGCTTTTG  GTTATTTCCA  AAAGACTTTG  CTCAGTAAGA  TCAAACGTTT  GTATTTCTCC   13260
GGGCCACAAT  ATTTGACCTA  TATGCACTGG  CCCACGCGCC  GCAATAGATG  AAAATTGCCA   13320
AAATTAGCTA  TCGGTCTTCT  GAAAAGAAGG  GCCGACATGT  TTTCATAGAC  CATGCAAAGT   13380
CATACTACCT  GAAACTGATA  AATAACGACA  AAGAAAGTAG  CCTATTTAAA  AGTCGCTATA   13440
GCATGAATTC  AACACAAGGA  AACCAAAAGT  CGGAAGGAAG  ACTTTAATCC  CGGATTATTT   13500
```

```
GGACATGATA GGAGCTATGG GGCAACGTGT CATTTTCATG AGTGTTGAAT GATTTTCTGT    13560
AGCAAATAGA AAACGTTTTT TAAAACGATG TGGCCTTGGA GTAATCAGCG GAAGAAATGG    13620
TCATGCTCAG ATAATTTCCG TTGCTGACCT CGCAACCAAC CCCTTTAAAT ACCTCTGCTG    13680
CCCATGCATT TTGCCAAGTT AACCTAAAGT GGCAGCTGAA TGGCTCGTTA TTGCAGTGGT    13740
GGCTCTCAAC GGCTTCATGT CGATGATTTT CGTTGGATCA AGGAGCCCAC TCGACTGAAG    13800
GCTCAGCTTA TTAATGTGGT GGAGACCTAC AAGGCTGCAC AAACAGAGAC GTTAAAGTAC    13860
TATATATCAT CTGCAACTGA GCGTGTGGCT CATGTGGAGG CAGCCGAGGT CAACAATGCG    13920
GAAATGGAGC TGCATCCTGC TGGGTTGAAG TACCCTCTGT CCTTCGTCTT TACCTCCCTG    13980
GCCGTGGCTA CAGCCTGCAA GGAGAACAAG CATCTCTTGT GCGAGGAGCA TTTGGAGGGG    14040
GACTTGATAT CGTGCGTCGT TCCTCCCTAT CAGACAAATG TCTCACTCGC TGCTTTAAGG    14100
GAGCTCCACA ATTCCATTTC GGGAGGAGGG TACCAGGAAC AAGCAGACAT GGATTATTTT    14160
GTGGCGATCA TCCCAAATGA TAATTTCGAC TATCAGAGCT GCGAAATCGA CACACGAAGT    14220
TGCGGTAAAG GACTTTGCAA GATTTATAGT AGGGAACTGG GAGGGCAGCC TCTAGCTTAT    14280
GACGCCATAC TGGCAATCGG CAAGGTGCTG CTGCTGGAAT AGATAGTGGG CCGCTGATCC    14340
GAGTTTGATT TTGTCGTATT ATGTTACGTG AACTTTTTAT CATGCATGTT TCGCTTATGC    14400
TCCCGAGTGT CGGCCATGTT GTTGTGTTAA AATAAAAGGC TGATGTTAAG TCCTATTGTA    14460
AAATACCTTT ATAGATTAAA TATATATAGT ATAACTTCTG TATGCCGTCG ATGAGCGGTT    14520
ATATGATTGT AATCTATACG TTGTTGCAAT CAATCGTATT ACAGTGAGCC GTGCTTAATG    14580
GGGGAAACGT AATAACATTG CGGTGGATAC AGCGTTTATT GGGAGGTCCG CGGGCCGATA    14640
CACTTAAATA ACATAGACAG AATTTGAGAG AGCACGCAGG TTGTAGCCAA GTTGAGCGAC    14700
TTGCCGGTAG CACGGAAGCT AAGCTCAGGT GTTACAAATA GACAGGCGTC GAGGCGACGA    14760
TTGCCGGTAG CACGGAAGCT AAGCTCAGGT GTTACAAATA GACAGGCGTC GAGGCGACGA    14820
GCACGACGAC CTTGCCGGAC ATTGCGGTCG CAGGGGCTC AAAGCGGTTG GCTTGTAACG     14880
GACCTTGTGT TTCTTGTTGT AGCTTTCATC GAGCATAACC ATTGGGACGG TTGCTGAACA    14940
ACGGTAACGC ACTTTTTTCA CGGGAGCGAG GTAGAAGAAC ATATTTCCCC GTCGGCAGCC    15000
GGCGGTGAGC ATGCCAATTC CTAAGGGATC AATGGACTCG TGCGAACGGT GAGCATGCCG    15060
TTCTGACCGT CGGTGCCCAA TCAGCAGGCC ACTCCCAACA TGTTTTCCAA GTCCTTAAAA    15120
CCAGTCTTTA TAGCATTGAT CTCCCAGCAA TCTTTATTGA AGTCGATTTT AATATTCAAA    15180
AGAAGATTTT AGTGGAAAGG GAATATAATC GCGTGGCCGA AGAAGAGCCT TCAAAAATCA    15240
GAATCCACTA GGATAAACAA TAATATCTGA AAAGCATTGA ATTTGGGTTA GGCACGAGAG    15300
GCTGACGCGG ATGCCACTCG ATTGCTAGTG GAAGGATTCC CTTTTTTCTA GCGTATCGAA    15360
TTCACCGTTT CACTATATGT TTTCCTGATT GGTTGATCTG CGGGACCACC ATTGACTGCC    15420
ACTAATATCG AAAGTGGGTC TGCTTCGATT ATGATGCTTT GTGAGAGGTT CTCTTCCCAA    15480
TGCATGCAAG CTGGCAGATT CGGATACTCT CAATAGAGAT CTTATTTCGC GTCTCAAAAA    15540
GTTCCCAGAA ATCAACAAAG GGGAGGGCAG GTCCTTTAAA TACGTTGCAG CTGTCCTTTA    15600
AAATAGAAGA GAATTTACAG CTGGAGGCAC AGACCACTAA ACTGCGAAAG TAAGCATGGC    15660
AGATGAGTTG GAGCGTCAAT TGGAAGCCAT TTCTCTCATT ACAGTCCTGG GTCCGGATGT    15720
GAAGGCTGAG CTTGAGGCGG AGCTACGAGA CTACTGCGAA GATCTCGACT TCTGGAAAAG    15780
CCACGGTTTA CCGGTGGCGG ATCTCGATCA GACTGTGACT GTCGACAAGC TTCTATACAT    15840
GTATATGGAT CGGGCAACAG CAGACCTGTG TGTGAAGAAT CGCTGCCTCG TTTGCAACAG    15900
```

| | | | | | | |
|---|---|---|---|---|---|---|
| TGGCAATTCA | GCCGCAAAAG | TAACCTCGCT | TCCACCATAC | CTTGCAGGCG | TGACAAGCGC | 15960 |
| CGAGGCCTAT | GAGAAACTCA | ACTCCATTGT | TGATGGGAGT | GTCGCCCCCC | AATCTCGTGG | 16020 |
| GCCTCCCTGC | TATTTTGTGG | CGTTCCTGCC | CAGCAGCTGT | TTCGAGAAAA | CCAGTGAGAT | 16080 |
| ATCGGTGCGC | ACAGTGGACG | GCGAGTGTGG | CCCCTTCGAT | GTCTTTACCC | GGCAGCGTCA | 16140 |
| GCCACAGGAT | CAGAGTGATA | TGTTTTTTAA | ATATGAAGGA | GTTGTATGTG | CTGGAAAGAG | 16200 |
| TGTATTTATG | TAAGAATTAT | CTTTTATAGC | CTGTGTTACG | TTTGAACCCG | GTCCGCGCGG | 16260 |
| TATTGTTTTC | AATAAATGGT | ATGTGCGGAG | GATATAATTG | GTCTTTCATT | GGTGTGATTT | 16320 |
| ACGTGTAACG | CGGATAATAA | TAAAGTAAAT | TACAAAAGAG | AAACGCATAA | TTTTATTCCA | 16380 |
| GAATGATTGC | GAGAAACGAT | GAAAATACAT | GAAAATGCAT | ATTGTCGCCA | GGGAAGGATG | 16440 |
| GCGCCGAAAT | AAACGAAACT | GAGCCAATAC | AGTGACTTGC | CAAGCGAGTT | TGATCCTACC | 16500 |
| AAATTCGCGC | AAATTAATGC | CCGTGTTCCA | TCGGGCCAGC | GAGTTTATTC | AAAAGAGTTT | 16560 |
| CGTACACGTG | GGCGGCGACG | GCAACGTCAA | TGCTTGCTAG | CCCTACCGGC | GAGAAGTTGG | 16620 |
| CCGGCCCCTT | CCATGCCTTG | AGGTCATTCA | TCAAGGCCTC | GTCATCGAGA | ATTTCGGTGT | 16680 |
| AGTTCTTGAT | CCCATCGCGC | TTGCCGTGTT | GGGTCAGTTT | CATACCGCGC | CTAGAATAGT | 16740 |
| AGAGGGCAAC | GGCATCAACG | TTGCGGGCTT | CCATCGCAAC | AAGGTCATCG | GCGACAATTA | 16800 |
| GACCATCCGC | AGATAGGACA | TGCTCAATGT | AATCCGGCGG | CATGTCATCA | ATACCGAGTG | 16860 |
| ACAAAGTGAC | TGCGTTGGGG | GCGATTTCAG | CGGCTTCGAA | TACCGGTTTT | CCGTAGTTGG | 16920 |
| TCGCCATGAT | GACGAATTGA | GAATATGGCA | AAAGGCTACG | ATCGCCGACA | GCTTCAAGGC | 16980 |
| TAAAGGTTAC | GCAATCACGT | AACTTTTCGA | CGAGCTCGAA | ATTGGATTTC | TTACCGCGGC | 17040 |
| TGAGCACTGC | TACCTTACGA | ATTCTCTTAG | CGGCACCATA | GTTAAGTGAG | AGAATTACAG | 17100 |
| CTTCGGCAAC | TTTTCCAGCC | CCAAACAAGA | AAACGTCGAT | GTCCTCTCTG | CCTTGCAACA | 17160 |
| GCAGGTTTAC | GCATGCTAGC | GAGAACCAAC | CCGTTCTTCC | ATTAGAAATT | GCCACGCCCT | 17220 |
| CTACCGACAT | AAGGAGCGTC | CCGGACACCT | TGTCGCGCAG | GAAAATATCG | GAGTGCTGGA | 17280 |
| GCGGCTTTCC | GGTAGCGGCG | TTGGTTGGCG | CGAAGTGGAT | GTCTTTGGTG | CCGGAATATC | 17340 |
| TTCCGAAATA | GCCAATGAGT | GCTCCTTCAG | TCCATCCAGG | AACATTCTTG | TTGAACGTTA | 17400 |
| GGTAAGCTTT | GACATGTCCG | GCTTTTCCTG | CGGCAAACAC | CTCCCAATAG | GACTTGAGAG | 17460 |
| CTTCGTCAAC | AAATGCTGGT | GTGATCTGGA | TATCGAGGTT | TGATAGTGCA | GATTCAGTCC | 17520 |
| AGTGTACCTC | GCAAAGTTGT | TTGGCCATCT | GCCTTGTAGG | TGCGAATTTT | CTCTGCTCAA | 17580 |
| ATTGTTGAGG | TTAGCGGATT | TGTAAACGCG | TTTATATGGG | CTGCTTGGAG | GGTACTTTTG | 17640 |
| GATTAATTTT | TTTCTGCCAG | CGCATTCTGA | CGCGGCACCG | CTTTGGAAAG | TGCGCTGTGG | 17700 |
| GTCCGCGTTT | TCTACAATAA | TGTGCCGATC | CGGTCAGAAA | GTATATGGAT | GAGTTGTGCC | 17760 |
| AGCCTCACCA | ACGTGCTGCA | GGCCCATCAT | GACTACTTCA | ATGTTAATGG | GGGTAATGAA | 17820 |
| TAAATAGGCG | AAATTGGGTT | CACGGTGGGC | CCAGGGAATA | TAATATTGCC | GCAGAGGTAG | 17880 |
| TCGGATGCCA | AGGCCCGCAA | CTAATAGTTC | ACGAACAAAT | TCATTGTAGT | GGGCGGCCAA | 17940 |
| CTCCAAAACC | AATTGCCAGT | TATTGTATTG | CAATACATAT | ATGAGTATTC | GGATACAACT | 18000 |
| AATTTCATTA | AATAATATTT | TAAGTGTGGA | CAGAATAGCG | CCTAATAAAT | TTGCGAATGT | 18060 |
| TGTCCAATTG | ACGTTTTTAT | AGGTAACTCG | ATAAATCGTG | CTTTTGTGAT | ATTCTGATGC | 18120 |
| GGACAATATA | CATTAAACA | TAAAGATATA | AGTTATTGAG | GCATTTATGT | ATATTACAAT | 18180 |
| AGTGGGGTAC | ATTTTTCACA | GATGCTGTCA | CCCATGAAAT | ATTGGCAAAA | TACTCTTAAA | 18240 |
| ATATGCAAGA | AACTAAAGAG | GATGCATGGG | TTGGGCTGTA | GGTACATGGA | TGCAAATGCT | 18300 |

```
GTTTTGCAAT AAGTCATATA GTCTCGTCTG TTGAGTGAGG CCCATTCAAT CAGCAAGTAG    18360
GACTGAGGTG CATGATCGAC ATATTTTTGA ACCACAGTTT TGGCAAGTTT TTCATACAAA    18420
TGCACGGCTA CGGCCAAATC GTAGCTTGCA AGTCCAACTG CTGAAAAGTT AGCCGGCCCG    18480
TTCCAAGAAA TTAGCCTTTG CATAAGGACT GGATCGCGGA GAACTTCAGA GTAGTTCCTG    18540
ATCCCATTGT CCCTGCCGTG TTTTGTTAGC TTTAAATGGC GTCTTGAATA GTGCAGCGCC    18600
AACGAGTCGA TATTACGTGT TTCCATCGCA TCCATATCAT CTGCCACCAC GATGCCACTC    18660
AGCTTCAACA CGTGATCAAA ATAGTCAGCT GGCAATTCGT CAATTCCAAG CGTCAATGTA    18720
ACGGCATTGT CTGTGATCTC CTTCATCTCA AGACGGGCT TGTTTGAATT CGTCGCCGTA     18780
ATTATGAACT TGGATTTGCT GAGATATGCT CGATTGTTAA CAGCCTTGAG TGAAATCTTG    18840
ACTTCCGGCT GAAGCCTTTG CACCAACTCA TGGTTTGACT GGTTGCAGCG GCTGAGAATC    18900
GCGATTCGTT GAATTCTTCC AGATGCTCCC GAATTGAGGG CGAGGATGAT GGCCTCGGCA    18960
ACTTTACCTG CTCCGAATAG GAAGACATTG ATCTGGCTTC GGCCCTGCAA TAGGAGATTC    19020
AGGCATGCTA GTGCCAGCCA ACCAGTTCTC CTCTCCGATA TAGCCACCCC ATCAACAGAG    19080
AAGAGACGTC TACCTGTGAA ACGATTGCGA AGCCAACGTC GATGTGAGAA GTCGGTTCTT    19140
TGTATCTCGC GTTTGACGGA TTAGAATGGA TGCTTTTCAC ACCCGAATAG TCGCCGACGA    19200
AACCCACCAG AGCTCCCTCC GTACAGCCCT CTCGATCAAG TGGAACGAAG ACCTTGTTGT    19260
GGCCGAGCCG CCCTTCAGCA AAGAGGTGCC AATAATCTTT CAAGGCATCC GCGACGAGTT    19320
CCGGTGTAAT GTATATTCCA AAAGCCGATA GAGATTCCTC TGTCCAACAT TGCTCGTGTA    19380
TTTGATCGGC CATGTTTGTG TTTGATCAGC CTCCTTTCGA AAATTTCTTG AGTTTCGAAT    19440
AATTCTAAAA TCGAAGGACG ATTAATAGTG CCATACCAAG ACAAGAAGGG TAGGTGGGCC    19500
ATCAATCCAC AAGCCTAGCA CATTTGCTG TCTGCTCATG CAAGGTATCC AATGGAAGCC     19560
TGGATTGGTT AGCCGAACTT GGTGGGTTCA ATTGGAGCGG GCAGGTCACT TTTTGTCTCT    19620
CAAATAACTG AAACTAAGTT TTGTTATTTG GTATGTGTTT GTCTGTTCTG CCGAAGGTGC    19680
CCGAATTTGC GCAAATTCCT TTCTAAAAAG GCTTACATCT AGCAAAGGT GAGCCCTGTG     19740
CATCCCAGCA TTTGGACAAA GCGCGCCAAT TCGGACAGCG ACTGGCTGCG TTGGAGGCTC    19800
GGATCTCAAA GAATAGAAAA GAGTTATGAT CATGTTCAGA ACCGCCAATT TTGTGCGGTA    19860
TGAGCTCTTT GATGAAAGTA ATGGTTTCAA AAAAGCAACA TCGTGGGTGA AAGGTACCTA    19920
CATATCTTCA CAGACAATAA CTACTGTTGC TGTTTGCTGA TTGACTGACA GGATATATGT    19980
TCCTGTCATG TTTGTTCAAT TGTTCAATTG TTCAATTGTT CAATTGTTCA ATTGTTAATG    20040
TATAAGTTCG TGATGAAGGA TGGTTGTTTT AAAAATAGTA TGTTTGACTG AGGTTAAGTC    20100
ACTCACGTTT TGCACATCGA CGGACCGTAA GCATTCTTTC GGTAAGACCG AAGCTCGTCC    20160
CAGATAATAG GCCCGTGGA GGGAGGCCTT GTATGGGCCG ACCGATGGC GTGCTGAGCC      20220
GAGTACGGCG ACGCCTGCGG CGATTGCGCG GGCGGCACTG CGCGCAGGGG CACGGGTTCA    20280
TACGAGGACG AGCGTAAGGG GCATAGAGCT TTCCGCCCGT CGGGTTTCAG CCATATTGCT    20340
TGATTGCGGC CGACTGGAAT GCAGCCAGGT CGTGCTCGCC GGCGGCGCCT GGTCGAGCGG    20400
CATGCTGCGC ACCTCAGTGT TCGGCTTCCT CAGCTCACGG TTACTGTGTC GGCGCTAAGA    20460
ACCGAGGCCT TTGATGGCGG ACCTGGCCTT TTCAATCAAG GGATGCTGAT TTTCCATCCG    20520
TAAGCGTCTC GACGGTGGTT ACACCGTCGG CTTCGGCGCG ACGATGAGAA CCGAAATCGT    20580
CAGCGATAGC TTTCGTTTTC TGTCGGATTA TTTCCTCCTG ATGCGAGAGG AATGGCTTTC    20640
TATCCGGCTG CCGGCGGGTG CGCGCGTCCG GATTGACCCT CCCGTTCGTT GCTACTTGGC    20700
```

| | | | | | | |
|---|---|---|---|---|---|---|
|TCGAGTGACG|AAATAGCACG|CCTGTGCCGC|TGTATCATGT|CCATCGGGCT|CACAGGAGAT|20760|
|TCGCTCGTAG|CGCGTTGGTG|TCACTCACCA|ACACGCGTCG|TCGCACCAAA|TTGGGGAGGA|20820|
|TGGTAGCGGA|ATCCTAAAAT|CCTAAAACCA|TACCGACGCG|TCACGGCGCT|CGTGACCCCT|20880|
|GCGAGCGACG|CGGCACTCTC|TCACCTGATC|CGTGCTGCGG|TTGCTCAATA|CGCAATGAGC|20940|
|ATTGTCACGG|TTCTCAGGGT|AAACGGCAAT|CTCTTCGTCA|TGCGGGCGTG|GATGCTATCA|21000|
|CCGTTAGAAA|GGGCCTGCCC|CCATGGTGGG|TCTCTAAGGT|TCAGTCTGAG|AAGGGGCAGC|21060|
|CAGAGCGGCA|CTGTTTGAAG|AGCAGTCTGA|ACCGCTCAGA|TCGCTCGCAT|CGATGCTTGG|21120|
|GCGGCG| | | | | |21126|

We claim:

1. A DNA molecule comprising a pRi $T_L$-DNA promoter and a heterologous foreign structural gene, the promoter and the structural gene being in such position and orientation with respect to one another that the structural gene is expressible in a plant cell under control of the promoter.

2. A DNA molecule comprising:
(a) a pRi $T_L$-DNA promoter from a gene selected from the group consisting of genes for $T_L$-DNA ORF's 1, 2, 3, 4, 5, 6, 8, 9, 10, 11, 12, 13, 14, 15, 16, and 17, and
(b) a heterologous structural gene wherein said structural gene is not natively under the control of said promoter, the promoter and the structural gene being in such position and orientation with respect to one another that the structural gene is expressible in a plant cell under control of the promoter, wherein the DNA is within a dicotyledonous plant cell, a dicotyledonous plant tissue, a dicotyledonous plant or a dicotyledonous plant seed.

3. A plant, plant cell, plant tissue, or plant seed, each of said plant, cell, tissue, or seed being derived or descended from a genetically modified dicotyledonous plant cell produced by transforming the cell to contain a pRi $T_L$-DNA promoter and a heterologous foreign structural gene, the promoter and the structural gene being in such a position and orientation with respect to one another that the structural gene is expressible in a plant cell under control of the promoter wherein the promoter/structural gene combination is integrated into a plant chromosome, whereby the combination is flanked by plant DNA, said promoter/structural gene combination being present in said plant, plant cell, plant tissue, or plant seed.

4. An isolated nucleic acid molecule designated pRi $T_L$-DNA and having the nucleic acid sequence of Sequence ID No. 19.

* * * * *

UNITED STATES PATENT AND TRADEMARK OFFICE
CERTIFICATE OF CORRECTION

PATENT NO. : 5,824,866
DATED : October 20, 1998
INVENTOR(S) : Jerry L. Slightom, David A. Tepfer It is certified that error appears in the above-identified patent and that said Letters Patent is hereby corrected as shown below:

Column 2, line 44: "Pohler" should read --Pühler--.

Column 3, line 55: "Wostemeyer" should read --Wöstemeyer--.

Column 10, line 36: "pRiHRI" should read --pRiHRI√--.

Column 13, line 57: "15are" should read --15√ are--;

line 58: "15being" should read --15√ being--;

line 59: "12expression" should read --12√ expression--.

Column 15, line 8: "being In the" should read --being in the--.

Column 19, line 66: "(Ne)" should read --(Nde)--.

UNITED STATES PATENT AND TRADEMARK OFFICE
CERTIFICATE OF CORRECTION

PATENT NO. : 5,824,866  Page 2 of 4
DATED : October 20, 1998
INVENTOR(S) : Jerry L. Slightom, David A. Tepfer It is certified that error appears in the above-identified patent and that said Letters Patent is hereby corrected as shown below:

Column 21, line 5: "the'presence" should read --the presence--;

line 23: "63163 6365" should read --6316, 6365--.

Column 24, line 6: "et a ." should read --et al.--.

Column 30, line 26: "105:561-663." should read --105:661-663.--.

Column 31, line 8: "mBtCP'" should read --mBtCP'--;

line 17: "mBtCP'" should read --mBtCP'--.

UNITED STATES PATENT AND TRADEMARK OFFICE
CERTIFICATE OF CORRECTION

PATENT NO. : 5,824,866
DATED : October 20, 1998
INVENTOR(S) : Jerry L. Slightom, David A. Tepfer It is certified that error appears in the above-identified patent and that said Letters Patent is hereby corrected as shown below:

Column 33, line 6: "(a dam host" should read --(a <u>dam</u>-host--;

line 12: "p233DNA" should read --p233G DNA--.

Column 34, line 3: "pyroxidine HCl. 50 mg/l thiamine-HCl" should read

--pyroxidine·HCl. 50 mg/l thiamine·HCl,-- line 35: "7 Regeneration" should read --6.7 Regeneration--.

Column 35, Table 1, line BssHII: "190 761" should read --19 761--;

Table 1, AccI line: "4 515" should read --4 516--.

UNITED STATES PATENT AND TRADEMARK OFFICE
CERTIFICATE OF CORRECTION

PATENT NO. : 5,824,866
DATED : October 20, 1998
INVENTOR(S) : Jerry L. Slightom, David A. Tepfer It is certified that error appears in the above-identified patent and that said Letters Patent is hereby corrected as shown below:

Column 36, line NaeI: "9 0771" should read --9 771--;

line AhaIII: "13 530" should read --13 580--;

line 35: "FnuII 6&" should read --Fnu II 68--.

Column 37, Table 3, line 14: "CCAAT; CAAA" should read --CCAAT; CAAAA--.

Column 38, Table 3, line 16: "AATTAA: TATAAA" should read

--AATTAA; TATAAA--.

Column 39-40, Table 6, 2nd line of ORF2: "ATGFGCA" should read --ATGTGCA--.

Signed and Sealed this

Fourth Day of May, 1999

Q. TODD DICKINSON

*Attest:*

*Attesting Officer*     Acting Commissioner of Patents and Trademarks